United States Patent
Ilg

(10) Patent No.: US 11,542,507 B2
(45) Date of Patent: Jan. 3, 2023

(54) IMMUNOSTIMULATORY COMPOSITIONS

(71) Applicant: Bayer Animal Health GmbH, Leverkusen (DE)

(72) Inventor: Thomas Ilg, Monheim (DE)

(73) Assignee: Bayer Animal Health GmbH, Leverkusen (DE)

( * ) Notice: Subject to any disclaimer, the term of this patent is extended or adjusted under 35 U.S.C. 154(b) by 138 days.

(21) Appl. No.: 16/772,046

(22) PCT Filed: Dec. 7, 2018

(86) PCT No.: PCT/EP2018/083956
§ 371 (c)(1),
(2) Date: Jun. 11, 2020

(87) PCT Pub. No.: WO2019/115385
PCT Pub. Date: Jun. 20, 2019

(65) Prior Publication Data
US 2021/0170020 A1  Jun. 10, 2021

(30) Foreign Application Priority Data

Dec. 15, 2017 (EP) .................................... 17207740
Dec. 15, 2017 (EP) .................................... 17207746
Dec. 15, 2017 (EP) .................................... 17207750

(51) Int. Cl.
| | | |
|---|---|---|
| *C07H 21/04* | (2006.01) | |
| *A61K 9/127* | (2006.01) | |
| *A61K 31/713* | (2006.01) | |
| *C07H 21/02* | (2006.01) | |
| *C12N 15/113* | (2010.01) | |
| *C12N 15/117* | (2010.01) | |
| *A61K 39/39* | (2006.01) | |
| *A61P 37/04* | (2006.01) | |
| *A61K 39/00* | (2006.01) | |

(52) U.S. Cl.
CPC ............ *C12N 15/117* (2013.01); *A61K 39/39* (2013.01); *A61P 37/04* (2018.01); *A61K 2039/55555* (2013.01); *A61K 2039/55561* (2013.01); *A61K 2039/60* (2013.01); *C12N 2310/17* (2013.01); *C12N 2310/315* (2013.01); *C12N 2310/3341* (2013.01); *C12N 2310/3515* (2013.01); *C12N 2320/31* (2013.01)

(58) Field of Classification Search
CPC .............. A61K 38/19; A61K 2300/00; A61K 31/7088; A61K 31/713; C12N 2310/321
See application file for complete search history.

(56) References Cited

U.S. PATENT DOCUMENTS

| | | |
|---|---|---|
| 2013/0295167 A1 | 11/2013 | Abraham et al. |
| 2014/0010865 A1 | 1/2014 | Abraham et al. |
| 2019/0201434 A1 | 7/2019 | Abraham et al. |

FOREIGN PATENT DOCUMENTS

| | | |
|---|---|---|
| WO | 9602555 A1 | 2/1996 |
| WO | 2004016805 A2 | 2/2004 |
| WO | 2012084951 A1 | 6/2012 |
| WO | WO2012084951 * | 6/2012 |
| WO | 2012/089800 A1 | 7/2012 |
| WO | 2014/001422 A2 | 1/2014 |
| WO | 2015/011261 A1 | 1/2015 |

OTHER PUBLICATIONS

PCT International Search Report for PCT/EP2018/083956, dated May 13, 2019.
Gomis, Susantha, et al. "Protection of chickens against *Escherichia coli* infections by DNA containing CpG motifs." Infection and immunity, (2003), vol. 71, No. 2: 857-863.
Suschak et al. Hum Vaccin. Immunother. (2017) 13(12): 2837-2848.

* cited by examiner

*Primary Examiner* — Barry A Chestnut
(74) *Attorney, Agent, or Firm* — McBee Moore & Vanik IP, LLC

(57) ABSTRACT

The present disclosure relates to immunostimulatory compositions that are effective in eliciting immune responses in avian species. More specifically, these immunostimulatory compositions comprise an immunomodulator composition and an immunostimulatory oligonucleotide that when administered stimulate toll-like receptor 21.

47 Claims, 23 Drawing Sheets
Specification includes a Sequence Listing.

SEQUENCE LISTING

<160> NUMBER OF SEQ ID NOS: 269

<210> SEQ ID NO 1
<211> LENGTH: 36
<212> TYPE: DNA
<213> ORGANISM: Artificial Sequence
<220> FEATURE:
<223> OTHER INFORMATION: /note="Description of Artificial Sequence:
      Synthetic oligonucleotide"
<220> FEATURE:
<221> NAME/KEY: misc_feature
<223> OTHER INFORMATION: /note="5'-Cholesteryl modified"

<400> SEQUENCE: 1
tggggttttt tttgcgtttt tgcgtttttg cgtttt                     36

<210> SEQ ID NO 2

<400> SEQUENCE: 2

000

<210> SEQ ID NO 3
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic oligonucleotide"
<220> FEATURE:
<221> NAME/KEY: misc_feature
<222> LOCATION: (1)..(24)
<223> OTHER INFORMATION: /note="Phosphorothioate linkage between
      nucleotides"

<400> SEQUENCE: 3
tcgtcgtttt gtcgttttgt cgtt                                  24

<210> SEQ ID NO 4
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 4
tcgtcgtttt gtcgttttgt cgtt                                  24

<210> SEQ ID NO 5
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 5
tcgtcgtttt gtcgttttgt cgttg                                 25

<210> SEQ ID NO 6
<211> LENGTH: 26
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 6

-continued tcgtcgtttt gtcgttttgt cgttgg          26

<210> SEQ ID NO 7
<211> LENGTH: 27
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 7
tcgtcgtttt gtcgttttgt cgttggg         27

<210> SEQ ID NO 8
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 8
tcgtcgtttt gtcgttttgt cgttgggg        28

<210> SEQ ID NO 9
<211> LENGTH: 29
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 9
tcgtcgtttt gtcgttttgt cgttggggg       29

<210> SEQ ID NO 10
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 10
tcgtcgtttt gtcgttttgt cgttgggggg      30

<210> SEQ ID NO 11
<211> LENGTH: 31
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 11
tcgtcgtttt gtcgttttgt cgttggggggg g   31

<210> SEQ ID NO 12
<211> LENGTH: 32
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 12
tcgtcgtttt gtcgttttgt cgttgggggg gg                32

<210> SEQ ID NO 13
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 13
tcgtcgtttt gtcgttttgt cgtt                         24

<210> SEQ ID NO 14
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 14
gtcgtcgttt tgtcgttttg tcgtt                        25

<210> SEQ ID NO 15
<211> LENGTH: 26
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 15
ggtcgtcgtt ttgtcgtttt gtcgtt                       26

<210> SEQ ID NO 16
<211> LENGTH: 27
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 16
gggtcgtcgt ttgtcgtttt gtcgtt                       27

<210> SEQ ID NO 17
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 17
ggggtcgtcg ttttgtcgtt ttgtcgtt                     28

<210> SEQ ID NO 18
<211> LENGTH: 29
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 18
gggggtcgtc gttttgtcgt tttgtcgtt                    29

```
<210> SEQ ID NO 19
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 19
ggggggtcgt cgttttgtcg ttttgtcgtt                                          30

<210> SEQ ID NO 20
<211> LENGTH: 31
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 20
gggggggtcg tcgttttgtc gttttgtcgt t                                        31

<210> SEQ ID NO 21
<211> LENGTH: 32
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 21
ggggggggtc gtcgttttgt cgttttgtcg tt                                       32

<210> SEQ ID NO 22
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 22
aaaaaatcgt cgttttgtcg ttttgtcgtt                                          30

<210> SEQ ID NO 23
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 23 ccccccctcgt cgttttgtcg ttttgtcgtt                                         30

<210> SEQ ID NO 24
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 24 ttttttcgt cgttttgtcg ttttgtcgtt                                           30
```

-continued

```
<210> SEQ ID NO 25
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"
<220> FEATURE:
<221> NAME/KEY: modified_base
<222> LOCATION: (8)..(8)
<223> OTHER INFORMATION: 5-methyl-cytidine
<220> FEATURE:
<221> NAME/KEY: modified_base
<222> LOCATION: (11)..(11)
<223> OTHER INFORMATION: 5-methyl-cytidine
<220> FEATURE:
<221> NAME/KEY: modified_base
<222> LOCATION: (19)..(19)
<223> OTHER INFORMATION: 5-methyl-cytidine
<220> FEATURE:
<221> NAME/KEY: modified_base
<222> LOCATION: (27)..(27)
<223> OTHER INFORMATION: 5-methyl-cytidine

<400> SEQUENCE: 25 gggggtcgt cgttttgtcg ttttgtcgtt                                     30

<210> SEQ ID NO 26
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 26
cccccctgct gcttttgtgc ttttgtgctt                                    30

<210> SEQ ID NO 27
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 27 ttttttcat cattttgtca ttttgtcatt                                     30

<210> SEQ ID NO 28
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"
<220> FEATURE:
<221> NAME/KEY: misc_feature
<222> LOCATION: (1)..(30)
<223> OTHER INFORMATION: /note="Phosphorothioate linkage between
      nucleotides"

<400> SEQUENCE: 28
tgggggtcgt cgttttgtcg ttttgtcgtt                                    30

<210> SEQ ID NO 29
<211> LENGTH: 29
<212> TYPE: DNA
<213> ORGANISM: Artificial Sequence
<220> FEATURE:
```

<223> OTHER INFORMATION: /note="Description of Artificial Sequence:
      Synthetic oligonucleotide"
<220> FEATURE:
<221> NAME/KEY: misc_feature
<222> LOCATION: (1)..(29)
<223> OTHER INFORMATION: /note="Phosphorothioate linkage between
      nucleotides"

<400> SEQUENCE: 29
tcgtcgtttt gtcgttttgt cgttggggg                                    29

<210> SEQ ID NO 30
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 30 aggggggtcgt cgttttgtcg ttttgtcgtt                                  30

<210> SEQ ID NO 31
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 31
gaggggtcgt cgttttgtcg ttttgtcgtt                                   30

<210> SEQ ID NO 32
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 32
ggagggtcgt cgttttgtcg ttttgtcgtt                                   30

<210> SEQ ID NO 33
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 33
gggaggtcgt cgttttgtcg ttttgtcgtt                                   30

<210> SEQ ID NO 34
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 34
ggggagtcgt cgttttgtcg ttttgtcgtt                                   30

<210> SEQ ID NO 35

```
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 35
gggggatcgt cgttttgtcg ttttgtcgtt                                    30

<210> SEQ ID NO 36
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 36
aaggggtcgt cgttttgtcg ttttgtcgtt                                    30

<210> SEQ ID NO 37
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 37
gaagggtcgt cgttttgtcg ttttgtcgtt                                    30

<210> SEQ ID NO 38
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 38
ggaaggtcgt cgttttgtcg ttttgtcgtt                                    30

<210> SEQ ID NO 39
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 39
gggaagtcgt cgttttgtcg ttttgtcgtt                                    30

<210> SEQ ID NO 40
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 40
ggggaatcgt cgttttgtcg ttttgtcgtt                                    30

<210> SEQ ID NO 41
<211> LENGTH: 30
```

```
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 41 cggggtcgt cgttttgtcg ttttgtcgtt                                          30

<210> SEQ ID NO 42
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 42
gcggggtcgt cgttttgtcg ttttgtcgtt                                         30

<210> SEQ ID NO 43
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 43
ggcgggtcgt cgttttgtcg ttttgtcgtt                                         30

<210> SEQ ID NO 44
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 44
gggcggtcgt cgttttgtcg ttttgtcgtt                                         30

<210> SEQ ID NO 45
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 45
ggggcgtcgt cgttttgtcg ttttgtcgtt                                         30

<210> SEQ ID NO 46
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 46
gggggctcgt cgttttgtcg ttttgtcgtt                                         30

<210> SEQ ID NO 47
<211> LENGTH: 30
<212> TYPE: DNA
```

<213> ORGANISM: Artificial Sequence
<220> FEATURE:
<223> OTHER INFORMATION: /note="Description of Artificial Sequence: Synthetic oligonucleotide"

<400> SEQUENCE: 47
ccggggtcgt cgttttgtcg ttttgtcgtt                                30

<210> SEQ ID NO 48
<211> LENGTH: 30
<212> TYPE: DNA
<213> ORGANISM: Artificial Sequence
<220> FEATURE:
<223> OTHER INFORMATION: /note="Description of Artificial Sequence: Synthetic oligonucleotide"

<400> SEQUENCE: 48
gccgggtcgt cgttttgtcg ttttgtcgtt                                30

<210> SEQ ID NO 49
<211> LENGTH: 30
<212> TYPE: DNA
<213> ORGANISM: Artificial Sequence
<220> FEATURE:
<223> OTHER INFORMATION: /note="Description of Artificial Sequence: Synthetic oligonucleotide"

<400> SEQUENCE: 49
ggccggtcgt cgttttgtcg ttttgtcgtt                                30

<210> SEQ ID NO 50
<211> LENGTH: 30
<212> TYPE: DNA
<213> ORGANISM: Artificial Sequence
<220> FEATURE:
<223> OTHER INFORMATION: /note="Description of Artificial Sequence: Synthetic oligonucleotide"

<400> SEQUENCE: 50
gggccgtcgt cgttttgtcg ttttgtcgtt                                30

<210> SEQ ID NO 51
<211> LENGTH: 30
<212> TYPE: DNA
<213> ORGANISM: Artificial Sequence
<220> FEATURE:
<223> OTHER INFORMATION: /note="Description of Artificial Sequence: Synthetic oligonucleotide"

<400> SEQUENCE: 51
ggggcctcgt cgttttgtcg ttttgtcgtt                                30

<210> SEQ ID NO 52
<211> LENGTH: 30
<212> TYPE: DNA
<213> ORGANISM: Artificial Sequence
<220> FEATURE:
<223> OTHER INFORMATION: /note="Description of Artificial Sequence: Synthetic oligonucleotide"

<400> SEQUENCE: 52
tgggggtcgt cgttttgtcg ttttgtcgtt                                30

<210> SEQ ID NO 53
<211> LENGTH: 30
<212> TYPE: DNA
<213> ORGANISM: Artificial Sequence

```
<220> FEATURE:
<223> OTHER INFORMATION: /note="Description of Artificial Sequence:
      Synthetic oligonucleotide"

<400> SEQUENCE: 53
gtggggtcgt cgttttgtcg ttttgtcgtt                                           30

<210> SEQ ID NO 54
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 54
ggtgggtcgt cgttttgtcg ttttgtcgtt                                           30

<210> SEQ ID NO 55
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 55
gggtggtcgt cgttttgtcg ttttgtcgtt                                           30

<210> SEQ ID NO 56
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 56
ggggtgtcgt cgttttgtcg ttttgtcgtt                                           30

<210> SEQ ID NO 57
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 57
gggggttcgt cgttttgtcg ttttgtcgtt                                           30

<210> SEQ ID NO 58
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 58
ttggggtcgt cgttttgtcg ttttgtcgtt                                           30

<210> SEQ ID NO 59
<211> LENGTH: 30
<212> TYPE: DNA
<213> ORGANISM: Artificial Sequence
<220> FEATURE:
```

```
<223> OTHER INFORMATION: /note="Description of Artificial Sequence:
      Synthetic oligonucleotide"

<400> SEQUENCE: 59
gttgggtcgt cgttttgtcg ttttgtcgtt                                           30

<210> SEQ ID NO 60
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 60
ggttggtcgt cgttttgtcg ttttgtcgtt                                           30

<210> SEQ ID NO 61
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 61
gggttgtcgt cgttttgtcg ttttgtcgtt                                           30

<210> SEQ ID NO 62
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 62
ggggtttcgt cgttttgtcg ttttgtcgtt                                           30

<210> SEQ ID NO 63
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 63
agggtcgtcg ttttgtcgtt ttgtcgtt                                             28

<210> SEQ ID NO 64
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 64
gaggtcgtcg ttttgtcgtt ttgtcgtt                                             28

<210> SEQ ID NO 65
<211> LENGTH: 28
<212> TYPE: DNA
<213> ORGANISM: Artificial Sequence
<220> FEATURE:
<223> OTHER INFORMATION: /note="Description of Artificial Sequence:
```

Synthetic oligonucleotide"

<400> SEQUENCE: 65
ggagtcgtcg ttttgtcgtt ttgtcgtt                                28

<210> SEQ ID NO 66
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 66
gggatcgtcg ttttgtcgtt ttgtcgtt                                28

<210> SEQ ID NO 67
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 67
cgggtcgtcg ttttgtcgtt ttgtcgtt                                28

<210> SEQ ID NO 68
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 68
gcggtcgtcg ttttgtcgtt ttgtcgtt                                28

<210> SEQ ID NO 69
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 69
ggcgtcgtcg ttttgtcgtt ttgtcgtt                                28

<210> SEQ ID NO 70
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 70
gggctcgtcg ttttgtcgtt ttgtcgtt                                28

<210> SEQ ID NO 71
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 71
tgggtcgtcg ttttgtcgtt ttgtcgtt                                    28

<210> SEQ ID NO 72
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 72
gtggtcgtcg ttttgtcgtt ttgtcgtt                                    28

<210> SEQ ID NO 73
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 73
ggtgtcgtcg ttttgtcgtt ttgtcgtt                                    28

<210> SEQ ID NO 74
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 74
gggttcgtcg ttttgtcgtt ttgtcgtt                                    28

<210> SEQ ID NO 75
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 75
tccatgacgt tcctgatgct                                             20

<210> SEQ ID NO 76
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 76
tccatgacgt tcctgatgct ggggg                                       25

<210> SEQ ID NO 77
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic oligonucleotide"

```
<400> SEQUENCE: 77
ggggtccatg acgttcctga tgct                                              24

<210> SEQ ID NO 78
<211> LENGTH: 26
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 78
gggggtccca tgacgttcct gatgct                                            26

<210> SEQ ID NO 79
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 79
tccatgacgt tcctgacgtt                                                   20

<210> SEQ ID NO 80
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 80
tccatgacgt tcctgacgtt ggggg                                             25

<210> SEQ ID NO 81
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 81
ggggtccatg acgttcctga cgtt                                              24

<210> SEQ ID NO 82
<211> LENGTH: 26
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 82 gggggtcca tgacgttcct gacgtt                                             26

<210> SEQ ID NO 83
<211> LENGTH: 23
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 83
```

-continued tcgacgttcg tcgttcgtcg ttc                                      23

<210> SEQ ID NO 84
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 84
tcgacgttcg tcgttcgtcg ttcggggg                                 28

<210> SEQ ID NO 85
<211> LENGTH: 27
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 85
ggggtcgacg ttcgtcgttc gtcgttc                                  27

<210> SEQ ID NO 86
<211> LENGTH: 29
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 86 gggggggtcga cgttcgtcgt tcgtcgttc                               29

<210> SEQ ID NO 87
<211> LENGTH: 26
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 87
tcgcgacgtt cgcccgacgt tcggta                                   26

<210> SEQ ID NO 88
<211> LENGTH: 31
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 88
tcgcgacgtt cgcccgacgt tcggtagggg g                             31

<210> SEQ ID NO 89
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 89
ggggtcgcga cgttcgcccg acgttcggta                                30

<210> SEQ ID NO 90
<211> LENGTH: 32
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 90 gggggtcgc gacgttcgcc cgacgttcgg ta                              32

<210> SEQ ID NO 91
<211> LENGTH: 22
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 91
tcgtcgtttt cggcgcgcgc cg                                        22

<210> SEQ ID NO 92
<211> LENGTH: 26
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 92
ggggtcgtcg ttttcggcgc gcgccg                                    26

<210> SEQ ID NO 93
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 93 gggggtcgt cgttttcggc gcgcgccg                                   28

<210> SEQ ID NO 94
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 94
tcgtcgtcgt tcgaacgacg ttgat                                     25

<210> SEQ ID NO 95
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 95
tcgtcgtcgt tcgaacgacg ttgatggggg                                30

<210> SEQ ID NO 96
<211> LENGTH: 29
<212> TYPE: DNA
<213> ORGANISM: Artificial Sequence
<220> FEATURE:
<223> OTHER INFORMATION: /note="Description of Artificial Sequence: Synthetic oligonucleotide"

<400> SEQUENCE: 96
ggggtcgtcg tcgttcgaac gacgttgat                                29

<210> SEQ ID NO 97
<211> LENGTH: 31
<212> TYPE: DNA
<213> ORGANISM: Artificial Sequence
<220> FEATURE:
<223> OTHER INFORMATION: /note="Description of Artificial Sequence: Synthetic oligonucleotide"

<400> SEQUENCE: 97 gggggggtcgt cgtcgttcga acgacgttga t                            31

<210> SEQ ID NO 98
<211> LENGTH: 22
<212> TYPE: DNA
<213> ORGANISM: Artificial Sequence
<220> FEATURE:
<223> OTHER INFORMATION: /note="Description of Artificial Sequence: Synthetic oligonucleotide"

<400> SEQUENCE: 98
tcgtcgttgt cgttttgtcg tt                                       22

<210> SEQ ID NO 99
<211> LENGTH: 27
<212> TYPE: DNA
<213> ORGANISM: Artificial Sequence
<220> FEATURE:
<223> OTHER INFORMATION: /note="Description of Artificial Sequence: Synthetic oligonucleotide"

<400> SEQUENCE: 99
tcgtcgttgt cgttttgtcg ttggggg                                  27

<210> SEQ ID NO 100
<211> LENGTH: 28
<212> TYPE: DNA
<213> ORGANISM: Artificial Sequence
<220> FEATURE:
<223> OTHER INFORMATION: /note="Description of Artificial Sequence: Synthetic oligonucleotide"

<400> SEQUENCE: 100
ggggggtcgt cgttgtcgtt ttgtcgtt                                 28

<210> SEQ ID NO 101
<211> LENGTH: 19
<212> TYPE: DNA
<213> ORGANISM: Artificial Sequence
<220> FEATURE:
<223> OTHER INFORMATION: /note="Description of Artificial Sequence: Synthetic oligonucleotide"

<400> SEQUENCE: 101
gatctcgctc gctcgctat                                           19

```
<210> SEQ ID NO 102
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 102
gggggggatc tcgctcgctc gctat                                            25

<210> SEQ ID NO 103
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 103
tcgtcgacgt cgttcgttct c                                                21

<210> SEQ ID NO 104
<211> LENGTH: 27
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 104
ggggggtcgt cgacgtcgtt cgttctc                                          27

<210> SEQ ID NO 105
<211> LENGTH: 29
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 105
tccatgacgt tcctgcagtt cctgacgtt                                        29

<210> SEQ ID NO 106
<211> LENGTH: 35
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 106 gggggggtcca tgacgttcct gcagttcctg acgtt                                35

<210> SEQ ID NO 107
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 107
tccacgacgt tttcgacgtt                                                  20
```

```
<210> SEQ ID NO 108
<211> LENGTH: 26
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 108
gggggGtcca cgacgttttc gacgtt                                        26

<210> SEQ ID NO 109
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 109
tttttcgtcg ttttgtcgtt ttgtcgtt                                      28

<210> SEQ ID NO 110
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 110
ttagggtcgt cgttttgtcg ttttgtcgtt                                    30

<210> SEQ ID NO 111
<211> LENGTH: 36
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 111
ttagggttag ggtcgtcgtt ttgtcgtttt gtcgtt                             36

<210> SEQ ID NO 112
<211> LENGTH: 32
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 112
ttttggggtc gtcgttttgt cgttttgtcg tt                                 32

<210> SEQ ID NO 113
<211> LENGTH: 32
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 113 ggggttttc gtcgttttgt cgttttgtcg tt                                  32

<210> SEQ ID NO 114
```

```
<211> LENGTH: 36
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 114
ggggttttgg ggtcgtcgtt ttgtcgtttt gtcgtt                              36

<210> SEQ ID NO 115
<211> LENGTH: 34
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 115
ttagggtttt tcgtcgtttt gtcgttttgt cgtt                                34

<210> SEQ ID NO 116
<211> LENGTH: 40
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 116
ttagggttag ggttttcgt cgttttgtcg ttttgtcgtt                           40

<210> SEQ ID NO 117
<211> LENGTH: 44
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 117
tgtgggtgtg tgtgggtttt tcgtcgtttt gtcgttttgt cgtt                     44

<210> SEQ ID NO 118
<211> LENGTH: 33
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 118
ggaggttttt cgtcgttttg tcgttttgtc gtt                                 33

<210> SEQ ID NO 119
<211> LENGTH: 35
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 119
tggaggcttt ttcgtcgttt tgtcgttttg tcgtt                               35

<210> SEQ ID NO 120
<211> LENGTH: 42
```

-continued

```
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 120
tggaggctgg aggcttttc gtcgttttgt cgttttgtcg tt                          42

<210> SEQ ID NO 121
<211> LENGTH: 46
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 121
gctgcgaggc gggtgggtgg gatcgtcgtt ttgtcgtttt gtcgtt                     46

<210> SEQ ID NO 122
<211> LENGTH: 45
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 122
gctgcgggcg ggtgggtggg atcgtcgttt tgtcgttttg tcgtt                      45

<210> SEQ ID NO 123
<211> LENGTH: 42
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 123
cgaggcgggt gggtgggatc gtcgttttgt cgttttgtcg tt                         42

<210> SEQ ID NO 124
<211> LENGTH: 41
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 124
cgggcgggtg ggtgggatcg tcgttttgtc gttttgtcgt t                          41

<210> SEQ ID NO 125
<211> LENGTH: 42
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 125
gggcgtggtg ggtggggttc gtcgttttgt cgttttgtcg tt                         42

<210> SEQ ID NO 126
<211> LENGTH: 40
<212> TYPE: DNA
```

-continued

```
<213> ORGANISM: Artificial Sequence
<220> FEATURE:
<223> OTHER INFORMATION: /note="Description of Artificial Sequence:
      Synthetic oligonucleotide"

<400> SEQUENCE: 126
ggggtgggag gagggttcgt cgttttgtcg ttttgtcgtt                              40

<210> SEQ ID NO 127
<211> LENGTH: 44
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 127
ggggtcgggc gggccgggtg tcgtcgtttt gtcgttttgt cgtt                         44

<210> SEQ ID NO 128
<211> LENGTH: 48
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 128
ggtggtgggg ggggttggta gggttcgtcg ttttgtcgtt ttgtcgtt                     48

<210> SEQ ID NO 129
<211> LENGTH: 44
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 129
gggttagggt tagggtaggg tcgtcgtttt gtcgttttgt cgtt                         44

<210> SEQ ID NO 130
<211> LENGTH: 41
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 130
tgggggggtg ggtgggttcg tcgttttgtc gttttgtcgt t                            41

<210> SEQ ID NO 131
<211> LENGTH: 40
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 131
gggcgggcgg gcgggctcgt cgttttgtcg ttttgtcgtt                              40

<210> SEQ ID NO 132
<211> LENGTH: 39
<212> TYPE: DNA
<213> ORGANISM: Artificial Sequence
```

<220> FEATURE:
<223> OTHER INFORMATION: /note="Description of Artificial Sequence:
      Synthetic oligonucleotide"

<400> SEQUENCE: 132
ggttggtgtg gttggtcgtc gttttgtcgt tttgtcgtt                    39

<210> SEQ ID NO 133
<211> LENGTH: 42
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 133
ggtggatggc gcagtcggtc gtcgttttgt cgttttgtcg tt               42

<210> SEQ ID NO 134
<211> LENGTH: 44
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 134
tgggggtgga cgggccgggt tcgtcgtttt gtcgttttgt cgtt             44

<210> SEQ ID NO 135
<211> LENGTH: 46
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 135 tgtggggtg gacgggccgg gttcgtcgtt ttgtcgtttt gtcgtt            46

<210> SEQ ID NO 136
<211> LENGTH: 45
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 136
gggttagggt tagggttagg gtcgtcgttt tgtcgttttg tcgtt            45

<210> SEQ ID NO 137
<211> LENGTH: 47
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 137
gggcgcggga ggaagggggc gggtcgtcgt tttgtcgttt tgtcgtt          47

<210> SEQ ID NO 138
<211> LENGTH: 43
<212> TYPE: DNA
<213> ORGANISM: Artificial Sequence
<220> FEATURE:

```
<223> OTHER INFORMATION: /note="Description of Artificial Sequence:
      Synthetic oligonucleotide"

<400> SEQUENCE: 138
agggtgggga gggtggggat cgtcgttttg tcgttttgtc gtt                    43

<210> SEQ ID NO 139
<211> LENGTH: 46
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 139
agggagggcg ctgggaggag ggtcgtcgtt ttgtcgtttt gtcgtt                 46

<210> SEQ ID NO 140
<211> LENGTH: 44
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 140
ggggcgggcc gggggcgggg tcgtcgtttt gtcgttttgt cgtt                   44

<210> SEQ ID NO 141
<211> LENGTH: 34
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 141
ggggttgggg tcgtcgtttt gtcgttttgt cgtt                              34

<210> SEQ ID NO 142
<211> LENGTH: 38
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 142
ggggttgggg tttttcgtcg ttttgtcgtt ttgtcgtt                          38

<210> SEQ ID NO 143
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 143
tggggttcgt cgttttgtcg ttttgtcgtt                                   30

<210> SEQ ID NO 144
<211> LENGTH: 14
<212> TYPE: DNA
<213> ORGANISM: Artificial Sequence
<220> FEATURE:
<223> OTHER INFORMATION: /note="Description of Artificial Sequence:
```

Synthetic oligonucleotide"

<400> SEQUENCE: 144
tttttttacg attt 14

<210> SEQ ID NO 145
<211> LENGTH: 14
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 145
tttttttgcg attt 14

<210> SEQ ID NO 146
<211> LENGTH: 14
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 146
tttttttccg attt 14

<210> SEQ ID NO 147
<211> LENGTH: 14
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 147
ttttttttcg attt 14

<210> SEQ ID NO 148
<211> LENGTH: 14
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 148
tttttttacg gttt 14

<210> SEQ ID NO 149
<211> LENGTH: 14
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 149
tttttttgcg gttt 14

<210> SEQ ID NO 150
<211> LENGTH: 14
<212> TYPE: DNA
<213> ORGANISM: Artificial Sequence
<220> FEATURE:
<223> OTHER INFORMATION: /note="Description of Artificial Sequence:
      Synthetic oligonucleotide"

```
<400> SEQUENCE: 150
tttttttccg gttt                                              14

<210> SEQ ID NO 151
<211> LENGTH: 14
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 151 tttttttttcg gttt                                             14

<210> SEQ ID NO 152
<211> LENGTH: 14
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 152
tttttttacg cttt                                              14

<210> SEQ ID NO 153
<211> LENGTH: 14
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 153
tttttttgcg cttt                                              14

<210> SEQ ID NO 154
<211> LENGTH: 14
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 154
tttttttccg cttt                                              14

<210> SEQ ID NO 155
<211> LENGTH: 14
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 155 tttttttttcg cttt                                             14

<210> SEQ ID NO 156
<211> LENGTH: 14
<212> TYPE: DNA
<213> ORGANISM: Artificial Sequence
<220> FEATURE:
<223> OTHER INFORMATION: /note="Description of Artificial Sequence:
      Synthetic oligonucleotide"
```

```
<400> SEQUENCE: 156 ttttttttacg tttt                                              14

<210> SEQ ID NO 157
<211> LENGTH: 14
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 157
tttttttgcg tttt                                               14

<210> SEQ ID NO 158
<211> LENGTH: 14
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 158
tttttttccg tttt                                               14

<210> SEQ ID NO 159
<211> LENGTH: 14
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 159
ttttttttcg tttt                                               14

<210> SEQ ID NO 160
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 160 gggggggtttt tttacgattt                                        20

<210> SEQ ID NO 161
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 161 gggggggtttt tttgcgattt                                        20

<210> SEQ ID NO 162
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 162
```

-continued gggggggtttt tttccgattt                                              20

<210> SEQ ID NO 163
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 163 gggggggtttt ttttcgattt                                              20

<210> SEQ ID NO 164
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 164 gggggggtttt tttacggttt                                              20

<210> SEQ ID NO 165
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 165 gggggggtttt tttgcggttt                                              20

<210> SEQ ID NO 166
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 166 gggggggtttt tttccggttt                                              20

<210> SEQ ID NO 167
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 167 gggggggtttt ttttcggttt                                              20

<210> SEQ ID NO 168
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 168
ggggggtttt tttacgcttt                                            20

<210> SEQ ID NO 169
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 169
ggggggtttt tttgcgcttt                                            20

<210> SEQ ID NO 170
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 170
ggggggtttt tttccgcttt                                            20

<210> SEQ ID NO 171
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 171
ggggggtttt ttttcgcttt                                            20

<210> SEQ ID NO 172
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 172
ggggggtttt tttacgtttt                                            20

<210> SEQ ID NO 173
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 173
ggggggtttt tttgcgtttt                                            20

<210> SEQ ID NO 174
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 174
ggggggtttt tttccgtttt                                            20

<210> SEQ ID NO 175
<211> LENGTH: 20
<212> TYPE: DNA
<213> ORGANISM: Artificial Sequence
<220> FEATURE:
<223> OTHER INFORMATION: /note="Description of Artificial Sequence:
Synthetic oligonucleotide"

<400> SEQUENCE: 175 gggggtttt ttttcgtttt                                               20

<210> SEQ ID NO 176
<211> LENGTH: 28
<212> TYPE: DNA
<213> ORGANISM: Artificial Sequence
<220> FEATURE:
<223> OTHER INFORMATION: /note="Description of Artificial Sequence:
Synthetic oligonucleotide"

<400> SEQUENCE: 176
ggggttgggg ttttttttt tacgattt                                      28

<210> SEQ ID NO 177
<211> LENGTH: 28
<212> TYPE: DNA
<213> ORGANISM: Artificial Sequence
<220> FEATURE:
<223> OTHER INFORMATION: /note="Description of Artificial Sequence:
Synthetic oligonucleotide"

<400> SEQUENCE: 177
ggggttgggg ttttttttt tgcgattt                                      28

<210> SEQ ID NO 178
<211> LENGTH: 28
<212> TYPE: DNA
<213> ORGANISM: Artificial Sequence
<220> FEATURE:
<223> OTHER INFORMATION: /note="Description of Artificial Sequence:
Synthetic oligonucleotide"

<400> SEQUENCE: 178
ggggttgggg ttttttttt tccgattt                                      28

<210> SEQ ID NO 179
<211> LENGTH: 28
<212> TYPE: DNA
<213> ORGANISM: Artificial Sequence
<220> FEATURE:
<223> OTHER INFORMATION: /note="Description of Artificial Sequence:
Synthetic oligonucleotide"

<400> SEQUENCE: 179
ggggttgggg ttttttttt ttcgattt                                      28

<210> SEQ ID NO 180
<211> LENGTH: 28
<212> TYPE: DNA
<213> ORGANISM: Artificial Sequence
<220> FEATURE:
<223> OTHER INFORMATION: /note="Description of Artificial Sequence:
Synthetic oligonucleotide"

<400> SEQUENCE: 180
ggggttgggg ttttttttt tacggttt                                      28

<210> SEQ ID NO 181
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 181
ggggttgggg ttttttttt tgcggttt                                    28

<210> SEQ ID NO 182
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 182
ggggttgggg ttttttttt tccggttt                                    28

<210> SEQ ID NO 183
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 183
ggggttgggg ttttttttt ttcggttt                                    28

<210> SEQ ID NO 184
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 184
ggggttgggg ttttttttt tacgcttt                                    28

<210> SEQ ID NO 185
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 185
ggggttgggg ttttttttt tgcgcttt                                    28

<210> SEQ ID NO 186
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 186
ggggttgggg ttttttttt tccgcttt                                    28

-continued

```
<210> SEQ ID NO 187
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 187
ggggttgggg ttttttttt ttcgcttt                                           28

<210> SEQ ID NO 188
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 188
ggggttgggg ttttttttt tacgtttt                                           28

<210> SEQ ID NO 189
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 189
ggggttgggg ttttttttt tgcgtttt                                           28

<210> SEQ ID NO 190
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 190
ggggttgggg ttttttttt tccgtttt                                           28

<210> SEQ ID NO 191
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 191
ggggttgggg ttttttttt ttcgtttt                                           28

<210> SEQ ID NO 192
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 192
ggggttgggg ttttttttt tggctttt                                           28

<210> SEQ ID NO 193
```

-continued

```
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 193
ggggttgggg ttttttttttt tgtgtttt                                      28

<210> SEQ ID NO 194
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 194
ggggttgggg ttttttttttt tgcatttt                                      28

<210> SEQ ID NO 195
<211> LENGTH: 27
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 195
ggggttgggg ttttttttttt gcgtttt                                       27

<210> SEQ ID NO 196
<211> LENGTH: 26
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 196
ggggttgggg tttttttttg cgtttt                                         26

<210> SEQ ID NO 197
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 197
ggggttgggg ttttttttgc gtttt                                          25

<210> SEQ ID NO 198
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 198
ggggttgggg tttttttgcg tttt                                           24

<210> SEQ ID NO 199
<211> LENGTH: 23
```

```
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 199
ggggttgggg tttttttgcgt ttt                                              23

<210> SEQ ID NO 200
<211> LENGTH: 22
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 200
ggggttgggg tttttgcgtt tt                                                22

<210> SEQ ID NO 201
<211> LENGTH: 27
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 201
ggggttgggg tttttttttt tgcgttt                                           27

<210> SEQ ID NO 202
<211> LENGTH: 26
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 202
ggggttgggg tttttttttt tgcgtt                                            26

<210> SEQ ID NO 203
<211> LENGTH: 25
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 203
ggggttgggg tttttttttt tgcgt                                             25

<210> SEQ ID NO 204
<211> LENGTH: 35
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 204
ggggttgggg tttttttttt tgcgttttgc gtttt                                  35

<210> SEQ ID NO 205
<211> LENGTH: 43
<212> TYPE: DNA
```

<213> ORGANISM: Artificial Sequence
<220> FEATURE:
<223> OTHER INFORMATION: /note="Description of Artificial Sequence: Synthetic oligonucleotide"

<400> SEQUENCE: 205
ggggttgggg ttttttttt tgcgttttgc gttttgcgt ttt        43

<210> SEQ ID NO 206
<211> LENGTH: 35
<212> TYPE: DNA
<213> ORGANISM: Artificial Sequence
<220> FEATURE:
<223> OTHER INFORMATION: /note="Description of Artificial Sequence: Synthetic oligonucleotide"

<400> SEQUENCE: 206
ggggttgggg ttttttttt tgcgatttgc gattt        35

<210> SEQ ID NO 207
<211> LENGTH: 42
<212> TYPE: DNA
<213> ORGANISM: Artificial Sequence
<220> FEATURE:
<223> OTHER INFORMATION: /note="Description of Artificial Sequence: Synthetic oligonucleotide"

<400> SEQUENCE: 207
ggggttgggg ttttttttt tgcgatttgc gatttgcgat tt        42

<210> SEQ ID NO 208
<211> LENGTH: 35
<212> TYPE: DNA
<213> ORGANISM: Artificial Sequence
<220> FEATURE:
<223> OTHER INFORMATION: /note="Description of Artificial Sequence: Synthetic oligonucleotide"

<400> SEQUENCE: 208
ggggttgggg ttttttttt tacgctttac gcttt        35

<210> SEQ ID NO 209
<211> LENGTH: 42
<212> TYPE: DNA
<213> ORGANISM: Artificial Sequence
<220> FEATURE:
<223> OTHER INFORMATION: /note="Description of Artificial Sequence: Synthetic oligonucleotide"

<400> SEQUENCE: 209
ggggttgggg ttttttttt tacgctttac gctttacgct tt        42

<210> SEQ ID NO 210
<211> LENGTH: 35
<212> TYPE: DNA
<213> ORGANISM: Artificial Sequence
<220> FEATURE:
<223> OTHER INFORMATION: /note="Description of Artificial Sequence: Synthetic oligonucleotide"

<400> SEQUENCE: 210
ggggttgggg ttttttttt ttcgcttttc gcttt        35

<210> SEQ ID NO 211
<211> LENGTH: 42
<212> TYPE: DNA
<213> ORGANISM: Artificial Sequence
<220> FEATURE:
<223> OTHER INFORMATION: /note="Description of Artificial Sequence: Synthetic oligonucleotide"

<400> SEQUENCE: 211
ggggttgggg ttttttttttt ttcgcttttc gctttttcgct tt            42

<210> SEQ ID NO 212
<211> LENGTH: 35
<212> TYPE: DNA
<213> ORGANISM: Artificial Sequence
<220> FEATURE:
<223> OTHER INFORMATION: /note="Description of Artificial Sequence: Synthetic oligonucleotide"

<400> SEQUENCE: 212
ggggttgggg ttttttttttt tccgctttcc gcttt            35

<210> SEQ ID NO 213
<211> LENGTH: 42
<212> TYPE: DNA
<213> ORGANISM: Artificial Sequence
<220> FEATURE:
<223> OTHER INFORMATION: /note="Description of Artificial Sequence: Synthetic oligonucleotide"

<400> SEQUENCE: 213
ggggttgggg ttttttttttt tccgctttcc gctttccgct tt            42

<210> SEQ ID NO 214
<211> LENGTH: 35
<212> TYPE: DNA
<213> ORGANISM: Artificial Sequence
<220> FEATURE:
<223> OTHER INFORMATION: /note="Description of Artificial Sequence: Synthetic oligonucleotide"

<400> SEQUENCE: 214
ggggttgggg ttttttttttt tgcggttttgc ggttt            35

<210> SEQ ID NO 215
<211> LENGTH: 42
<212> TYPE: DNA
<213> ORGANISM: Artificial Sequence
<220> FEATURE:
<223> OTHER INFORMATION: /note="Description of Artificial Sequence: Synthetic oligonucleotide"

<400> SEQUENCE: 215
ggggttgggg ttttttttttt tgcggtttgc ggtttgcggt tt            42

<210> SEQ ID NO 216
<211> LENGTH: 27
<212> TYPE: DNA
<213> ORGANISM: Artificial Sequence
<220> FEATURE:
<223> OTHER INFORMATION: /note="Description of Artificial Sequence: Synthetic oligonucleotide"

<400> SEQUENCE: 216
ggggttgggg ttttttttcg cgcgttt            27

<210> SEQ ID NO 217
<211> LENGTH: 29
<212> TYPE: DNA
<213> ORGANISM: Artificial Sequence
<220> FEATURE:

```
<223> OTHER INFORMATION: /note="Description of Artificial Sequence:
      Synthetic oligonucleotide"

<400> SEQUENCE: 217
ggggttgggg ttttttttcg tcgtcgttt                                29

<210> SEQ ID NO 218
<211> LENGTH: 31
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 218
ggggttgggg ttttttttcg ttcgttcgtt t                             31

<210> SEQ ID NO 219
<211> LENGTH: 33
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 219
ggggttgggg ttttttttcg tttcgtttcg ttt                           33

<210> SEQ ID NO 220
<211> LENGTH: 35
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 220
ggggttgggg ttttttttcg ttttcgtttt cgttt                         35

<210> SEQ ID NO 221
<211> LENGTH: 29
<212> TYPE: DNA
<213> ORGANISM: Artificial Sequence
<220> FEATURE:
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: Abasic site
<220> FEATURE:
<221> NAME/KEY: modified_base
<222> LOCATION: (24)..(24)
<223> OTHER INFORMATION: Abasic site

<400> SEQUENCE: 221
ggggttgggg ttttttttcg ncgncgttt                                29

<210> SEQ ID NO 222
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 222
ggggttgggg ttttttttcg                                          20
```

<210> SEQ ID NO 223
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 223
ggggttgggg ttttttttcg                                              20

<210> SEQ ID NO 224
<211> LENGTH: 34
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 224
ggggttgggg ttggggtttt ttttttttgcg tttt                             34

<210> SEQ ID NO 225
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 225
ggggttgggg ttttttttcg                                              20

<210> SEQ ID NO 226
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 226
ggggttgggg ttttttttcg                                              20

<210> SEQ ID NO 227
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 227
ggggttgggg ttttttttcg                                              20

<210> SEQ ID NO 228
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 228
ggggttgggg ttttttttcg                                              20

-continued

<210> SEQ ID NO 229
<211> LENGTH: 15
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 229
tggggttttt tttcg                                                    15

<210> SEQ ID NO 230
<211> LENGTH: 15
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 230
tggggttttt tttcg                                                    15

<210> SEQ ID NO 231
<211> LENGTH: 15
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 231
tggggttttt tttcg                                                    15

<210> SEQ ID NO 232
<211> LENGTH: 15
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 232
tggggttttt tttcg                                                    15

<210> SEQ ID NO 233
<211> LENGTH: 15
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 233
tggggttttt tttcg                                                    15

<210> SEQ ID NO 234
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 234
ggggttgggg ttttttttcg                                               20

```
<210> SEQ ID NO 235
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 235
ggggttgggg ttttttttcg                                                    20

<210> SEQ ID NO 236
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 236
ggggttgggg ttttttttcg                                                    20

<210> SEQ ID NO 237
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 237
ggggttgggg ttttttttcg                                                    20

<210> SEQ ID NO 238
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 238
ggggttgggg ttttttttcg                                                    20

<210> SEQ ID NO 239
<211> LENGTH: 29
<212> TYPE: DNA
<213> ORGANISM: Artificial Sequence
<220> FEATURE:
<223> OTHER INFORMATION: /note="Description of Artificial Sequence:
      Synthetic oligonucleotide"
<220> FEATURE:
<221> NAME/KEY: modified_base
<222> LOCATION: (21)..(21)
<223> OTHER INFORMATION: Abasic site
<220> FEATURE:
<221> NAME/KEY: modified_base
<222> LOCATION: (24)..(24)
<223> OTHER INFORMATION: Abasic site

<400> SEQUENCE: 239
ggggttgggg ttttttttcg ncgncgttt                                          29

<210> SEQ ID NO 240
<211> LENGTH: 20
<212> TYPE: DNA
<213> ORGANISM: Artificial Sequence
<220> FEATURE:
<223> OTHER INFORMATION: /note="Description of Artificial Sequence:
```

-continued

Synthetic oligonucleotide"

<400> SEQUENCE: 240
ggggttgggg ttttttttcg					20

<210> SEQ ID NO 241
<211> LENGTH: 22
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 241
ggggttgggg ttttttttac gc				22

<210> SEQ ID NO 242
<211> LENGTH: 22
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 242
ggggttgggg ttttttttcc gc				22

<210> SEQ ID NO 243
<211> LENGTH: 22
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 243
ggggttgggg ttttttttac gc				22

<210> SEQ ID NO 244
<211> LENGTH: 22
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 244
ggggttgggg ttttttttcc gc				22

<210> SEQ ID NO 245
<211> LENGTH: 17
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 245
tggggttttt tttacgc					17

<210> SEQ ID NO 246
<211> LENGTH: 17
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 246
tggggttttt tttccgc                                              17

<210> SEQ ID NO 247
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 247
tcgtcgtttt gtcgttttgt cgtt                                      24

<210> SEQ ID NO 248
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 248
tcgtcgtttt gtcgttttgt cgtt                                      24

<210> SEQ ID NO 249
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 249
ggggtcgtcg ttttgtcgtt ttgtcgtt                                  28

<210> SEQ ID NO 250
<211> LENGTH: 28
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 250
ggggtcgtcg ttttgtcgtt ttgtcgtt                                  28

<210> SEQ ID NO 251
<211> LENGTH: 34
<212> TYPE: DNA
<213> ORGANISM: Artificial Sequence
<220> FEATURE:
<223> OTHER INFORMATION: /note="Description of Artificial Sequence:
      Synthetic oligonucleotide"
<220> FEATURE:
<221> NAME/KEY: misc_feature
<223> OTHER INFORMATION: /note="May be 3'-Cholesteryl modified"

<400> SEQUENCE: 251
tggggttttt tcgtcgtttt gtcgttttgt cgtt                           34

<210> SEQ ID NO 252
<211> LENGTH: 36
<212> TYPE: DNA
<213> ORGANISM: Artificial Sequence
<220> FEATURE:

```
<223> OTHER INFORMATION: /note="Description of Artificial Sequence:
      Synthetic oligonucleotide"

<400> SEQUENCE: 252
tggggttttt tttgcgtttt tgcgtttttg cgtttt                                 36

<210> SEQ ID NO 253
<211> LENGTH: 41
<212> TYPE: DNA
<213> ORGANISM: Artificial Sequence
<220> FEATURE:
<223> OTHER INFORMATION: /note="Description of Artificial Sequence:
      Synthetic oligonucleotide"
<220> FEATURE:
<221> NAME/KEY: misc_feature
<223> OTHER INFORMATION: /note="May be 5'-Cholesteryl modified"

<400> SEQUENCE: 253
ggggttgggg tttttttgc gttttgcgt tttgcgttt t                              41

<210> SEQ ID NO 254
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"
<220> FEATURE:
<221> NAME/KEY: misc_feature
<223> OTHER INFORMATION: /note="May be 5'-Cholesteryl modified"

<400> SEQUENCE: 254
tttttttgcg tttttgcgtt tttgcgtttt                                        30

<210> SEQ ID NO 255
<211> LENGTH: 41
<212> TYPE: DNA
<213> ORGANISM: Artificial Sequence
<220> FEATURE:
<223> OTHER INFORMATION: /note="Description of Artificial Sequence:
      Synthetic oligonucleotide"
<220> FEATURE:
<221> NAME/KEY: misc_feature
<223> OTHER INFORMATION: /note="May be 5'-Cholesteryl modified"

<400> SEQUENCE: 255
ggggttgggg ttttttttcc gcttttccgc ttttccgctt t                           41

<210> SEQ ID NO 256
<211> LENGTH: 30
<212> TYPE: DNA
<213> ORGANISM: Artificial Sequence
<220> FEATURE:
<223> OTHER INFORMATION: /note="Description of Artificial Sequence:
      Synthetic oligonucleotide"
<220> FEATURE:
<221> NAME/KEY: misc_feature
<223> OTHER INFORMATION: /note="May be 5'-Cholesteryl modified"

<400> SEQUENCE: 256
tttttttccg cttttccgct tttccgcttt                                        30

<210> SEQ ID NO 257
<211> LENGTH: 10
<212> TYPE: DNA
<213> ORGANISM: Artificial Sequence
<220> FEATURE:
<223> OTHER INFORMATION: /note="Description of Artificial Sequence:
      Synthetic oligonucleotide"
```

<400> SEQUENCE: 257
ggggttgggg                                                              10

<210> SEQ ID NO 258
<211> LENGTH: 14
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 258
ggggttgggg tttt                                                         14

<210> SEQ ID NO 259

<400> SEQUENCE: 259

000

<210> SEQ ID NO 260

<400> SEQUENCE: 260

000

<210> SEQ ID NO 261
<211> LENGTH: 12
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 261
ttagggttag gg                                                           12

<210> SEQ ID NO 262
<211> LENGTH: 12
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 262
ggggttttgg gg                                                           12

<210> SEQ ID NO 263
<211> LENGTH: 16
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 263
ttagggttag ggtttt                                                       16

<210> SEQ ID NO 264
<211> LENGTH: 14
<212> TYPE: DNA
<213> ORGANISM: Artificial Sequence
<220> FEATURE:
<223> OTHER INFORMATION: /note="Description of Artificial Sequence:
      Synthetic oligonucleotide"

<400> SEQUENCE: 264
tggaggctgg aggc                                                    14

<210> SEQ ID NO 265
<211> LENGTH: 4242
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 265
tgaccgccca acgaccccg cccattgacg tcaataatga cgtatgttcc catagtaacg      60
ccaataggga ctttccattg acgtcaatgg gtggagtatt tacggtaaac tgcccacttg    120
gcagtacatc aagtgtatca tatgccaagt ccgcccccta ttgacgtcaa tgacggtaaa   180
tggcccgcct ggcattatgc ccagtacatg accttacggg actttcctac ttggcagtac   240
atctacgtat tagtcatcgc tattaccatg gtgatgcggt tttggcagta catcaatggg   300
cgtggatagc ggtttgactc acggggattt ccaagtctcc accccattga cgtcaatggg   360
agtttgtttt ggcaccaaaa tcaacgggac tttccaaaat gtcgtaacaa ctccgcccca   420
ttgacgcaaa tgggcggtag gcgtgtacgg tgggaggtct atataagcag agctcgttta   480
gtgaaccgtc agatcgcctg gagacgccat ccacgctgtt tgacctccat agaagacac    540 cgggaccgat ccagcctccc ctcgaagccg atctgataac ggtaccgata agctggcggc   600
cgattaagct acagaagttg gtcgtgaggc actgggcagg taagtatcaa ggttacaaga   660
caggtttaag gagaccaata gaaactgggc ttgtcgagac agagaagact cttgcgtttc   720
tgataggcac ctattggtct tactgacatc cactttgcct ttctctccac aggtgtccac   780
tcccaggttc aattacagct cttaagcagc gcaagcttg atatcgaatt cctgcagccc    840
gggggatcca ctagttctag agcggccgcc accgcggtgg agctcgaatt atcagatcga   900
ttaataacta tgctcaaaaa ttgtgtacct ttagcttttt aatttgtaaa ggggttaata   960
aggaatattt gatgtatagt gccttgacta gagatcataa tcagccatac cacatttgta  1020
gaggttttac ttgctttaaa aaacctccca cacctccccc tgaacctgaa acataaaatg  1080
aatgcaattg ttgttgttaa cttgtttatt gcagcttata atggttacaa ataaagcaat  1140
agcatcacaa atttcacaaa taaagcattt ttttcactgc attctagttg tggtttgtcc  1200
aaactcatca atgtatctta tcatgtctgg atcatcagat ctgccggtct ccctatagtg  1260
agtcgtatta atttcgataa gccaggttaa cctgcattaa tgaatcggcc aacgcgcggg  1320
gagaggcggt ttgcgtattg ggcgctcttc cgcttcctcg ctcactgact cgctgcgctc  1380
ggtcgttcgg ctgcggcgag cggtatcagc tcactcaaag gcggtaatac ggttatccac  1440
agaatcaggg gataacgcag gaaagaacat gtgagcaaaa ggccagcaaa aggccaggaa  1500
ccgtaaaaag gccgcgttgc tggcgttttt ccataggctc cgccccctg acgagcatca    1560 caaaaatcga cgctcaagtc agaggtggcg aaacccgaca ggactataaa gataccaggc  1620
gtttccccct ggaagctccc tcgtgcgctc tcctgttccg accctgccgc ttaccggata  1680
cctgtccgcc tttctccctt cgggaagcgt ggcgctttct catagctcac gctgtaggta  1740
tctcagttcg gtgtaggtcg ttcgctccaa gctgggctgt gtgcacgaac cccccgttca  1800
gcccgaccgc tgcgccttat ccggtaacta tcgtcttgag tccaacccgg taagacacga  1860
cttatcgcca ctggcagcag ccactggtaa caggattagc agagcgaggt atgtaggcgg  1920

```
tgctacagag ttcttgaagt ggtggcctaa ctacggctac actagaagaa cagtatttgg    1980
tatctgcgct ctgctgaagc cagttacctt cggaaaaaga gttggtagct cttgatccgg    2040
caaacaaacc accgctggta gcggtggttt ttttgtttgc aagcagcaga ttacgcgcag    2100
aaaaaaagga tctcaagaag atcctttgat cttttctacg gggtctgacg ctcagtggaa    2160
cgaaaactca cgttaaggga ttttggtcat gggcgcgcct aggcttttgc aaagatcgat    2220
caagagacag gatgaggatc gtttcgcagc ttttcattct gactgcaacg ggcaataagt    2280
ctctgtgtgg attaaaaaaa gagtgtctga tagcagcttc tgaactggtt acctgccgtg    2340
agtaaattaa aattttattg acttaggtca ctaaggcgcc ttgcgctgag gttgcgtcgt    2400
gatatcatca gggcagaccg gttacatccc cctaacaagc tgtataaaga gaaatactat    2460
ctcattggcg ttgcccgcac ctgacagtgc gacgttgggc tgcgtccgtc gaccaacggt    2520
accgaggtaa cagcccaatc tatccatgat ctcggccagg ccgggtcggc cgttatgcag    2580
cccggctcgg gtatgaagcc attaaggagc cgacccagcg cgaccgggcg gccggtcacg    2640
ctgcctctgc tgaagcctgc ctgtcactcc ctgcgcggcg tacccgccgt tctcatcgag    2700
taggctccgg atcgcgaccc cggacgggcc ctgggcccag gagcggccta tgacaaatgc    2760
cgggtagcga tccggcattc agcattgact gcgcacggat ccagtccttg caggagcctt    2820
atgccgacct agcaaaaaaa tgagcccgag ccgatcgcga gttgtgatcc ggtcccgccg    2880
attgccggtc gcgatgacgg tcctgtgtaa gcgttatcgt taccaattgt ttaagaagta    2940
tatacgctac gaggtacttg ataacttctg cgtagcatac atgaggtttt gtataaaaat    3000
ggcgggcgat atcaacgcag tgtcagaaat ccgaaacagt ctgcgggact ctggggttcg    3060
aaatgaccga ccaagcgacg cccaacctgc catcacgaga tttcgattcc accgccgcct    3120
tctatgaaag gttgggcttc ggaatcgttt tccgggacgc cggctggatg atcctccagc    3180
gcggggatct catgctggag ttcttcgccc accctaggcg cgctcatgag cggatacata    3240
tttgaatgta tttagaaaaa taaacaaata ggggttccgc gcacatttcc ccgaaaagtg    3300
ccacctaaat tgtaagcgtt aatattttgt taaaattcgc gttaaatttt tgttaaatca    3360
gctcattttt taaccaatag gccgaaatcg gcaaaatccc ttataaatca aaagaataga    3420
ccgagatagg gttgagtgtt gttccagttt ggaacaagag tccactatta agaacgtgg    3480 actccaacgt caaagggcga aaaaccgtct atcagggcga tggcccacta cgtgaaccat    3540 cacccctaatc aagttttttg gggtcgaggt gccgtaaagc actaaatcgg aaccctaaag    3600
ggagcccccg atttagagct tgacggggaa agccggcgaa cgtggcgaga aaggaaggga    3660
agaaagcgaa aggagcgggc gctagggcgc tggcaagtgt agcggtcacg ctgcgcgtaa    3720
ccaccacacc cgccgcgctt aatgcgccgc tacagggcgc gtcccattcg ccattcaggc    3780
tgcgcaactg ttgggaaggg cgatcggtgc gggcctcttc gctattacgc cagctggcga    3840 aaggggatg tgctgcaagg cgattaagtt gggtaacgcc agggttttcc cagtcacgac    3900
gttgtaaaac gacggccagt gagcgcgcgt aatacgactc actatagggc gaattgggta    3960
ccgggccccc cctcgagcag gatctataca ttgaatcaat attggcaatt agccatatta    4020
gtcattggtt atatagcata aatcaatatt ggctattggc cattgcatac gttgtatcta    4080
tatcataata tgtacattta tattggctca tgtccaatat gaccgccatg ttgacattga    4140
ttattgacta gttattaata gtaatcaatt acggggtcat tagttcatag cccatatatg    4200
gagttccgcg ttacataact tacggtaaat ggcccgcctg gc                       4242
```

<210> SEQ ID NO 266
<211> LENGTH: 4242
<212> TYPE: DNA
<213> ORGANISM: Artificial Sequence
<220> FEATURE:
<223> OTHER INFORMATION: /note="Description of Artificial Sequence: Synthetic polynucleotide"

<400> SEQUENCE: 266

| | | | | | |
|---|---|---|---|---|---|
| ctaaattgta | agcgttaata | ttttgttaaa | attcgcgtta | aattttttgtt | aaatcagctc | 60 |
| atttttttaac | caataggccg | aaatcggcaa | aatcccttat | aaatcaaaag | aatagaccga | 120 |
| gatagggttg | agtgttgttc | cagtttggaa | caagagtcca | ctattaaaga | acgtggactc | 180 |
| caacgtcaaa | gggcgaaaaa | ccgtctatca | gggcgatggc | ccactacgtg | aaccatcacc | 240 |
| ctaatcaagt | tttttggggt | cgaggtgccg | taaagcacta | aatcggaacc | ctaaagggag | 300 |
| cccccgattt | agagcttgac | ggggaaagcc | ggcgaacgtg | gcgagaaagg | aagggaagaa | 360 |
| agcgaaagga | gcgggcgcta | gggcgctggc | aagtgtagcg | gtcacgctgc | gcgtaaccac | 420 |
| cacacccgcc | gcgcttaatg | cgccgctaca | gggcgcgtcc | cattcgccat | tcaggctgcg | 480 |
| caactgttgg | gaagggcgat | cggtgcgggc | ctcttcgcta | ttacgccagc | tggcgaaagg | 540 |
| gggatgtgct | gcaaggcgat | taagttgggt | aacgccaggg | ttttcccagt | cacgacgttg | 600 |
| taaaacgacg | gccagtgagc | gcgcgtaata | cgactcacta | tagggcgaat | tgggtaccgg | 660 |
| gccccccctc | gagcaggatc | tatacattga | atcaatattg | gcaattagcc | atattagtca | 720 |
| ttggttatat | agcataaatc | aatattggct | attggccatt | gcatacgttg | tatctatatc | 780 |
| ataatatgta | catttatatt | ggctcatgtc | caatatgacc | gccatgttga | cattgattat | 840 |
| tgactagtta | ttaatagtaa | tcaattacgg | ggtcattagt | tcatagccca | tatatggagt | 900 |
| tccgcgttac | ataacttacg | gtaaatggcc | cgcctggctg | accgcccaac | gacccccgcc | 960 |
| cattgacgtc | aataatgacg | tatgttccca | tagtaacgcc | aatagggact | ttccattgac | 1020 |
| gtcaatgggt | ggagtattta | cggtaaactg | cccacttggc | agtacatcaa | gtgtatcata | 1080 |
| tgccaagtcc | gccccctatt | gacgtcaatg | acggtaaatg | gcccgcctgg | cattatgccc | 1140 |
| agtacatgac | cttacgggac | tttcctactt | ggcagtacat | ctacgtatta | gtcatcgcta | 1200 |
| ttaccatggt | gatgcggttt | tggcagtaca | tcaatgggcg | tggatagcgg | tttgactcac | 1260 |
| ggggatttcc | aagtctccac | cccattgacg | tcaatgggag | tttgttttgg | caccaaaatc | 1320 |
| aacgggactt | tccaaaatgt | cgtaacaact | ccgccccatt | gacgcaaatg | ggcggtaggc | 1380 |
| gtgtacggtg | ggaggtctat | ataagcagag | ctcgtttagt | gaaccgtcag | atcgcctgga | 1440 |
| gacgccatcc | acgctgtttt | gacctccata | gaagacaccg | ggaccgatcc | agcctcccct | 1500 |
| cgaagccgat | ctgataacgg | taccgataag | ctggcggccg | attaagctac | agaagttggt | 1560 |
| cgtgaggcac | tgggcaggta | agtatcaagg | ttacaagaca | ggtttaagga | gaccaataga | 1620 |
| aactgggctt | gtcgagacag | agaagactct | tgcgtttctg | ataggcacct | attggtctta | 1680 |
| ctgacatcca | ctttgccttt | ctctccacag | gtgtccactc | ccaggttcaa | ttacagctct | 1740 |
| taagcagccg | caagcttgat | atcgaattcc | tgcagcccgg | gggatccact | agttctagag | 1800 |
| cggccgccac | cgcggtggag | ctcgaattat | cagatcgatt | aataactatg | ctcaaaaatt | 1860 |
| gtgtaccttt | agctttttaa | tttgtaaagg | ggttaataag | gaatatttga | tgtatagtgc | 1920 |
| cttgactaga | gatcataatc | agccatacca | catttgtaga | ggttttactt | gctttaaaaa | 1980 |
| acctcccaca | cctccccctg | aacctgaaac | ataaaatgaa | tgcaattgtt | gttgttaact | 2040 |

```
tgtttattgc agcttataat ggttacaaat aaagcaatag catcacaaat ttcacaaata    2100
aagcattttt ttcactgcat tctagttgtg gtttgtccaa actcatcaat gtatcttatc    2160
atgtctggat catcagatct gccggtctcc ctatagtgag tcgtattaat ttcgataagc    2220
caggttaacc tgcattaatg aatcggccaa cgcgcgggga gaggcggttt gcgtattggg    2280
cgctcttccg cttcctcgct cactgactcg ctgcgctcgg tcgttcggct gcggcgagcg    2340
gtatcagctc actcaaaggc ggtaatacgg ttatccacag aatcagggga taacgcagga    2400
aagaacatgt gagcaaaagg ccagcaaaag gccaggaacc gtaaaaaggc cgcgttgctg    2460
gcgtttttcc ataggctccg ccccctgac gagcatcaca aaaatcgacg ctcaagtcag    2520
aggtggcgaa acccgacagg actataaaga taccaggcgt ttccccctgg aagctccctc    2580
gtgcgctctc ctgttccgac cctgccgctt accggatacc tgtccgcctt ctcccttcg    2640 ggaagcgtgg cgctttctca tagctcacgc tgtaggtatc tcagttcggt gtaggtcgtt    2700
cgctccaagc tgggctgtgt gcacgaaccc cccgttcagc ccgaccgctg cgccttatcc    2760
ggtaactatc gtcttgagtc aacccggta agacacgact tatcgccact ggcagcagcc    2820
actggtaaca ggattagcag agcgaggtat gtaggcggtg ctacagagtt cttgaagtgg    2880
tggcctaact acgctacac tagaagaaca gtatttggta tctgcgctct gctgaagcca    2940
gttaccttcg gaaaaagagt tggtagctct tgatccggca acaaaccac cgctggtagc    3000 ggtggttttt ttgtttgcaa gcagcagatt acgcgcagaa aaaaggatc tcaagaagat    3060 cctttgatct tttctacggg gtctgacgct cagtggaacg aaaactcacg ttaagggatt    3120
ttggtcatga gcgcgcctag gcttttgcaa agatcgatca agagacagga tgaggatcgt    3180
ttcgcatgat tgaacaagat ggattgcacg caggttctcc ggccgcttgg gtggagaggc    3240
tattcggcta tgactgggca acagacaa tcggctgctc tgatgccgcc gtgttccggc    3300
tgtcagcgca ggggcgcccg gttctttttg tcaagaccga cctgtccggt gccctgaatg    3360
aactgcaaga cgaggcagcg cggctatcgt ggctggccac gacgggcgtt ccttgcgcag    3420
ctgtgctcga cgttgtcact gaagcgggaa gggactggct gctattgggc gaagtgccgg    3480
ggcaggatct cctgtcatct caccttgctc ctgccgagaa agtatccatc atggctgatg    3540
caatgcggcg gctgcatacg cttgatccgg ctacctgccc attcgaccac caagcgaaac    3600
atcgcatcga gcgagcacgt actcggatgg aagccggtct tgtcgatcag gatgatctgg    3660
acgaagagca tcaggggctc gcgccagccg aactgttcgc caggctcaag gcgagcatgc    3720
ccgacgcgca ggatctcgtc gtgacccatg gcgatgcctg cttgccgaat atcatggtgg    3780
aaaatggccg cttttctgga ttcatcgact gtggccggct gggtgtggcg gaccgctatc    3840
aggacatagc gttggctacc cgtgatattg ctgaagagct tggcggcgaa tgggctgacc    3900
gcttcctcgt gctttacggt atcgccgctc ccgattcgca gcgcatcgcc ttctatcgcc    3960
ttcttgacga gttcttctga gcgggactct ggggttcgaa atgaccgacc aagcgacgcc    4020
caacctgcca tcacgagatt tcgattccac cgccgccttc tatgaaaggt tgggcttcgg    4080
aatcgttttc cgggacgccg gctggatgat cctccagcgc ggggatctca tgctggagtt    4140
cttcgcccac cctaggcgcg ctcatgagcg gatacatatt tgaatgtatt tagaaaaata    4200
aacaaatagg ggttccgcgc acatttcccc gaaaagtgcc ac                      4242
```

<210> SEQ ID NO 267
<211> LENGTH: 4242
<212> TYPE: DNA
<213> ORGANISM: Artificial Sequence
<220> FEATURE:
<223> OTHER INFORMATION: /note="Description of Artificial Sequence: Synthetic polynucleotide"

<400> SEQUENCE: 267

```
tgaccgccca acgaccccg cccattgacg tcaataatga cgtatgttcc catagtaacg      60
ccaataggga ctttccattg acgtcaatgg gtggagtatt tacggtaaac tgcccacttg     120
gcagtacatc aagtgtatca tatgccaagt ccgcccccta ttgacgtcaa tgacggtaaa    180
tggcccgcct ggcattatgc ccagtacatg accttacggg actttcctac ttggcagtac    240
atctacgtat tagtcatcgc tattaccatg gtgatgcggt tttggcagta catcaatggg    300
cgtggatagc ggtttgactc acggggattt ccaagtctcc accccattga cgtcaatggg    360
agtttgtttt ggcaccaaaa tcaacgggac tttccaaaat gtcgtaacaa ctccgcccca    420
ttgacgcaaa tgggcggtag cgtgtacgg tgggaggtct atataagcag agctcgttta    480
gtgaaccgtc agatcgcctg gagacgccat ccacgctgtt ttgacctcca tagaagacac    540
cgggaccgat ccagcctccc ctcgaagccg atctgataac ggtaccgata agctggcggc    600
cgattaagct acagaagttg gtcgtgaggc actgggcagg taagtatcaa ggttacaaga    660
caggtttaag gagaccaata gaaactgggc ttgtcgagac agagaagact cttgcgtttc    720
tgataggcac ctattggtct tactgacatc cactttgcct ttctctccac aggtgtccac    780
tcccaggttc aattacagct cttaagcagc cgcaagcttg tatcgaatt cctgcagccc    840
ggggatcca ctagttctag agcggccgcc accgcggtgg agctcgaatt atcagatcga    900
ttaataacta tgctcaaaaa ttgtgtacct ttagctttt aatttgtaaa ggggttaata    960
aggaatattt gatgtatagt gccttgacta gagatcataa tcagccatac cacatttgta   1020
gaggtttac ttgctttaaa aaacctccca cacctccccc tgaacctgaa acataaaatg    1080
aatgcaattg ttgttgttaa cttgttttat gcagcttata atggttacaa ataaagcaat    1140
agcatcacaa atttcacaaa taaagcattt ttttcactgc attctagttg tggtttgtcc    1200
aaactcatca atgtatctta tcatgtctgg atcatcagat ctgccggtct ccctatagtg    1260
agtcgtatta atttcgataa gccaggttaa cctgcattaa tgaatcggcc aacgcgcggg    1320
gagaggcggt ttgcgtattg ggcgctcttc cgcttcctcg ctcactgact cgctgcgctc    1380
ggtcgttcgg ctgcggcgag cggtatcagc tcactcaaag gcggtaatac ggttatccac    1440
agaatcaggg gataacgcag gaaagaacat gtgagcaaaa ggccagcaaa aggccaggaa    1500
ccgtaaaaag gccgcgttgc tggcgttttt ccataggctc cgcccccctg acgagcatca    1560
caaaaatcga cgctcaagtc agaggtggcg aaacccgaca ggactataaa gataccaggc    1620
gtttccccct ggaagctccc tcgtgcgctc tcctgttccg accctgccgc ttaccggata    1680
cctgtccgcc tttctccctt cgggaagcgt ggcgctttct catagctcac gctgtaggta    1740
tctcagttcg gtgtaggtcg ttcgctccaa gctgggctgt gtgcacgaac cccccgttca    1800
gcccgaccgc tgcgccttat ccggtaacta tcgtcttgag tccaacccgg taagacacga    1860
cttatcgcca ctggcagcag ccactggtaa caggattagc agagcgaggt atgtaggcgg    1920
tgctacagag ttcttgaagt ggtggcctaa ctacggctac actagaagaa cagtatttgg    1980
tatctgcgct ctgctgaagc cagttacctt cggaaaaaga gttggtagct cttgatccgg    2040
caaacaaacc accgctggta gcggtggttt ttttgtttgc aagcagcaga ttacgcgcag    2100
aaaaaaagga tctcaagaag atcctttgat cttttctacg gggtctgacg ctcagtggaa    2160
cgaaaactca cgttaaggga ttttggtcat gggcgcgcct aggcttttgc aaagatcgat    2220
```

```
caagagacag gatgaggatc gtttcgcatg attgaacaag atggattgca cgcaggttct    2280
ccggccgctt gggtggagag gctattcggc tatgactggg cacaacagac aatcggctgc    2340
tctgatgccg ccgtgttccg gctgtcagcg caggggcgcc cggttctttt tgtcaagacc    2400
gacctgtccg gtgccctgaa tgaactgcaa gacgaggcag cgcggctatc gtggctggcc    2460
acgacgggcg ttccttgcgc agctgtgctc gacgttgtca ctgaagcggg aagggactgg    2520
ctgctattgg gcgaagtgcc ggggcaggat ctcctgtcat ctcaccttgc tcctgccgag    2580
aaagtatcca tcatggctga tgcaatgcgg cggctgcata cgcttgatcc ggctacctgc    2640
ccattcgacc accaagcgaa acatcgcatc gagcgagcac gtactcggat ggaagccggt    2700
cttgtcgatc aggatgatct ggacgaagag catcaggggc tcgcgccagc cgaactgttc    2760
gccaggctca aggcgagcat gcccgacggc gaggatctcg tcgtgaccca tggcgatgcc    2820
tgcttgccga atatcatggt ggaaaatggc cgcttttctg gattcatcga ctgtggccgg    2880
ctgggtgtgg cggaccgcta tcaggacata gcgttggcta cccgtgatat tgctgaagag    2940
cttggcggcg aatgggctga ccgcttcctc gtgctttacg gtatcgccgc tcccgattcg    3000
cagcgcatcg ccttctatcg ccttcttgac gagttcttct gagcgggact ctggggttcg    3060
aaatgaccga ccaagcgacg cccaacctgc catcacgaga tttcgattcc accgccgcct    3120
tctatgaaag gttgggcttc ggaatcgttt tccgggacgc cggctggatg atcctccagc    3180
gcggggatct catgctggag ttcttcgccc accctaggcg cgctcatgag cggatacata    3240
tttgaatgta tttagaaaaa taaacaaata ggggttccgc gcacatttcc ccgaaaagtg    3300
ccacctaaat tgtaagcgtt aatattttgt taaaattcgc gttaaatttt tgttaaatca    3360
gctcattttt taaccaatag gccgaaatcg gcaaaatccc ttataaatca aagaataga    3420 ccgagatagg gttgagtgtt gttccagttt ggaacaagag tccactatta agaacgtgg    3480 actccaacgt caaagggcga aaaccgtct atcagggcga tggcccacta cgtgaaccat    3540 cacccctaatc aagttttttg gggtcgaggt gccgtaaagc actaaatcgg aaccctaaag    3600 ggagccccccg atttagagct tgacggggaa agccggcgaa cgtggcgaga aggaaggga    3660 agaaagcgaa aggagcgggc gctagggcgc tggcaagtgt agcggtcacg ctgcgcgtaa    3720
ccaccacacc cgccgcgctt aatgcgccgc tacagggcgc gtcccattcg ccattcaggc    3780
tgcgcaactg ttgggaaggg cgatcggtgc gggcctcttc gctattacgc cagctggcga    3840
aagggggatg tgctgcaagg cgattaagtt gggtaacgcc agggttttcc cagtcacgac    3900
gttgtaaaac gacggccagt gagcgcgcgt aatacgactc actatagggc gaattgggta    3960
ccgggccccc cctcgagcag gatctataca ttgaatcaat attggcaatt agccatatta    4020
gtcattggtt atatagcata aatcaatatt ggctattggc cattgcatac gttgtatcta    4080
tatcataata tgtacattta tattggctca tgtccaatat gaccgccatg ttgacattga    4140
ttattgacta gttattaata gtaatcaatt acgggtcat tagttcatag cccatatatg    4200
gagttccgcg ttacataact tacggtaaat ggcccgcctg gc                       4242

<210> SEQ ID NO 268
<211> LENGTH: 4242
<212> TYPE: DNA
<213> ORGANISM: Artificial Sequence
<220> FEATURE:
<223> OTHER INFORMATION: /note="Description of Artificial Sequence:
      Synthetic polynucleotide"

<400> SEQUENCE: 268
```

```
tgaccgccca acgacccccg cccattgacg tcaataatga cgtatgttcc catagtaacg      60
ccaataggga ctttccattg acgtcaatgg gtggagtatt tacggtaaac tgcccacttg     120
gcagtacatc aagtgtatca tatgccaagt ccgcccccta ttgacgtcaa tgacggtaaa     180
tggcccgcct ggcattatgc ccagtacatg accttacggg actttcctac ttggcagtac     240
atctacgtat tagtcatcgc tattaccatg gtgatgcggt tttggcagta catcaatggg     300
cgtggatagc ggtttgactc acggggattt ccaagtctcc accccattga cgtcaatggg     360
agtttgtttt ggcaccaaaa tcaacgggac tttccaaaat gtcgtaacaa ctccgcccca     420
ttgacgcaaa tgggcggtag gcgtgtacgg tgggaggtct atataagcag agctcgttta     480
gtgaaccgtc agatcgcctg gagacgccat ccacgctgtt ttgacctcca tagaagacac     540
cgggaccgat ccagcctccc ctcgaagccg atctgataac ggtaccgata agctggcggc     600
cgattaagct acagaagttg gtcgtgaggc actgggcagg taagtatcaa ggttacaaga     660
caggtttaag gagaccaata gaaactgggc ttgtcgagac agagaagact cttgcgtttc     720
tgataggcac ctattggtct tactgacatc cactttgcct ttctctccac aggtgtccac     780
tcccaggttc aattacagct cttaagcagc cgccaaaaca aaattcctca aaaatcatca     840
tcgaatgaat ggtgaaataa tttccctgaa taactgtagt gttttcaggg cgcggcataa     900
taattaacta tgctcaaaaa ttgtgtacct ttagcttttt aatttgtaaa ggggttaata     960
aggaatattt gatgtatagt gccttgacta gagatcataa tcagccatac cacatttgta    1020
gaggttttac ttgctttaaa aaacctccca cacctccccc tgaacctgaa acataaaatg    1080
aatgcaattg ttgttgttaa cttgtttatt gcagcttata atggttacaa ataaagcaat    1140
agcatcacaa atttcacaaa taaagcattt ttttcactgc attctagttg tggtttgtcc    1200
aaactcatca atgtatctta tcatgtctgg atcatcagat ctgccggtct ccctatagtg    1260
agtcgtatta atttcgataa gccaggttaa cctgcattaa tgaatcggcc aacgcgcggg    1320
gagaggcggt ttgcgtattg ggcgctcttc cgcttcctcg ctcactgact cgctgcgctc    1380
ggtcgttcgg ctgcggcgag cggtatcagc tcactcaaag gcggtaatac ggttatccac    1440
agaatcaggg gataacgcag gaaagaacat gtgagcaaaa ggccagcaaa aggccaggaa    1500
ccgtaaaaag gccgcgttgc tggcgttttt ccataggctc cgcccccctg acgagcatca    1560
caaaaatcga cgctcaagtc agaggtggcg aaacccgaca ggactataaa gataccaggc    1620
gtttccccct ggaagctccc tcgtgcgctc tcctgttccg accctgccgc ttaccggata    1680
cctgtccgcc tttctccctt cgggaagcgt ggcgctttct catagctcac gctgtaggta    1740
tctcagttcg gtgtaggtcg ttcgctccaa gctgggctgt gtgcacgaac ccccgttca    1800 gcccgaccgc tgcgccttat ccggtaacta tcgtcttgag tccaacccgg taagacacga    1860
cttatcgcca ctggcagcag ccactggtaa caggattagc agagcgaggt atgtaggcgg    1920
tgctacagag ttcttgaagt ggtggcctaa ctacggctac actagaagaa cagtatttgg    1980
tatctgcgct ctgctgaagc cagttacctt cggaaaaaga gttggtagct cttgatccgg    2040
caaacaaacc accgctggta gcggtggttt ttttgtttgc aagcagcaga ttacgcgcag    2100
aaaaaaagga tctcaagaag atcctttgat cttttctacg gggtctgacg ctcagtggaa    2160
cgaaaactca cgttaaggga ttttggtcat gggcgcgcct aggcttttgc aaagatcgat    2220
caagagacag gatgaggatc gtttcgcagc ttttcattct gactgcaacg ggcaataagt    2280
ctctgtgtgg attaaaaaaa gagtgtctga tagcagcttc tgaactggtt acctgccgtg    2340
```

-continued

| | |
|---|---|
| agtaaattaa aattttattg acttaggtca ctaaggcgcc ttgcgctgag gttgcgtcgt | 2400 |
| gatatcatca gggcagaccg gttacatccc cctaacaagc tgtataaaga gaaatactat | 2460 |
| ctcattggcg ttgcccgcac ctgacagtgc gacgttgggc tgcgtccgtc gaccaacggt | 2520 |
| accgaggtaa cagcccaatc tatccatgat ctcggccagg ccgggtcggc cgttatgcag | 2580 |
| cccggctcgg gtatgaagcc attaaggagc cgacccagcg cgaccgggcg gccggtcacg | 2640 |
| ctgcctctgc tgaagcctgc ctgtcactcc ctgcgcggcg tacccgccgt tctcatcgag | 2700 |
| taggctccgg atcgcgaccc cggacgggcc ctgggcccag gagcggccta tgacaaatgc | 2760 |
| cgggtagcga tccggcattc agcattgact gcgcacggat ccagtccttg caggagcctt | 2820 |
| atgccgaccg tagcaaaaaa tgagcccgag ccgatcgcga gttgtgatcc ggtcccgccg | 2880 |
| attgccggtc gcgatgacgg tcctgtgtaa gcgttatcgt taccaattgt ttaagaagta | 2940 |
| tatacgctac gaggtacttg ataacttctg cgtagcatac atgaggtttt gtataaaaat | 3000 |
| ggcgggcgat atcaacgcag tgtcagaaat ccgaaacagt ctgcgggact ctggggttcg | 3060 |
| aaatgaccga ccaagcgacg cccaacctgc catcacgaga tttcgattcc accgccgcct | 3120 |
| tctatgaaag gttgggcttc ggaatcgttt tccgggacgc cggctggatg atcctccagc | 3180 |
| gcggggatct catgctggag ttcttcgccc accctaggcg cgctcatgag cggatacata | 3240 |
| tttgaatgta tttagaaaaa taaacaaata ggggttccgc gcacatttcc ccgaaaagtg | 3300 |
| ccacctaaat tgtaagcgtt aatattttgt taaaattcgc gttaaatttt tgttaaatca | 3360 |
| gctcattttt taaccaatag gccgaaatcg gcaaaatccc ttataaatca aagaataga | 3420 |
| ccgagatagg gttgagtgtt gttccagttt ggaacaagag tccactatta agaacgtgg | 3480 |
| actccaacgt caaagggcga aaaaccgtct atcagggcga tggcccacta cgtgaaccat | 3540 |
| caccctaatc aagttttttg gggtcgaggt gccgtaaagc actaaatcgg aaccctaaag | 3600 |
| ggagcccccg atttagagct tgacggggaa agccggcgaa cgtggcgaga aggaaggga | 3660 |
| agaaagcgaa aggagcgggc gctagggcgc tggcaagtgt agcggtcacg ctgcgcgtaa | 3720 |
| ccaccacacc cgccgcgctt aatgcgccgc tacagggcgc gtcccattcg ccattcaggc | 3780 |
| tgcgcaactg ttgggaaggg cgatcggtgc gggcctcttc gctattacgc cagctggcga | 3840 |
| aaggggatg tgctgcaagg cgattaagtt gggtaacgcc agggttttcc cagtcacgac | 3900 |
| gttgtaaaac gacggccagt gagcgcgcgt aatacgactc actatagggc gaattgggta | 3960 |
| ccgggccccc cctcgaggtc gacggtatcg ataagcttga tatcgaattc ctgcagcccg | 4020 |
| ggggatccac tagttctaga gcggccgcca ccgcggtgga gctccagctt ttgttccctt | 4080 |
| tagtgagggt taattgcgcg cttggcgtaa tcatggtcat agctgttccc tgtgtgaaat | 4140 |
| tgttatccgc tcacaattcc acacaacata cgagccggaa gcataaagtg taaagcctgg | 4200 |
| ggtgcctaat gagtgagcta actcacatta attgcgttgc gc | 4242 |

<210> SEQ ID NO 269
<211> LENGTH: 16
<212> TYPE: DNA
<213> ORGANISM: Artificial Sequence
<220> FEATURE:
<223> OTHER INFORMATION: /note="Description of Artificial Sequence:
    Synthetic oligonucleotide"

<400> SEQUENCE: 269
tgtgggtgtg tgtggg                                                      16

US 11,542,507 B2

IMMUNOSTIMULATORY COMPOSITIONS

REFERENCE TO RELATED APPLICATIONS

This application claims priority to and the benefit of European Patent Application Nos. EP17207740.6, EP17207746.3, and EP17207750.5, each filed Dec. 15, 2017, the disclosures of which are incorporated herein by reference in their entireties.

SEQUENCE LISTING

This application contains a Sequence Listing which has been submitted electronically in ASCII format and is hereby incorporated by reference in its entirety. Said ASCII copy, created Nov. 30, 2018, is named BHC_168027_SL.txt and is 92,167 bytes in size.

FIELD OF THE INVENTION

Compositions and methods for stimulating toll-like receptor protein 21 (TLR21) are provided. More specifically, immunostimulatory oligonucleotides and compositions, methods of making immunostimulatory oligonucleotides and compositions, and methods of stimulating TLR21 are disclosed herein.

BACKGROUND OF THE INVENTION

The immune systems of vertebrates have evolved molecular mechanisms for recognizing invading pathogens and initiating cellular signaling pathways to actively resist infection. Some of the molecular mechanisms are specific for a particular microbe and involve biomolecules such as antibodies that recognize the surface antigens of a single species of pathogen. Unfortunately, pathogen-specific defense mechanisms are not completely effective as some animals do not develop any acquired resistance until after infection has set in, and in some instances, the pathogen has evolved stealthy means for evading a vertebrate's acquired defenses.

Vertebrates also recognize infections more generally, and this recognition leads to non-specific immune responses such as an uptick in cytokine expression. This defense can be elicited when cellular receptors bind to pathogen-associated molecular patterns (PAMPs). This interaction between the PAMP and the host's cognate receptor for the PAMP can initiate an immune response. For example, toll-like receptor protein 21 (TLR21) is the chicken functional homolog of mammalian TLR9 and is capable of recognizing unmethylated CpG motifs, which have a higher CpG content in microbes than in vertebrates. Known methodologies leverage this nonspecific immune response pathway by administering plasmids or oligonucleotides having unmethylated CpG motifs, and activation of TLR21 by CpG motif-containing nucleic acids has been shown to activate cellular signals involved in the immune responses to microbial infections. However, administered immunostimulatory plasmids or oligonucleotides alone may fail to elicit a response sufficient to combat infection.

Large-scale animal producers are in dire need of alternatives to antibiotic treatment of infections. Consumers are pressing these producers for antibiotic-free animal products, and at the same time, increasing incidence of infection due to antibiotic resistant pathogens is illuminating the dangers of administering antibiotics prophylactically to large populations. Similarly, antibiotic resistance is becoming a national emergency in human healthcare. Hospitals and doctors' office are becoming ground zero for the emergence of drug resistance bacteria such as multiple resistance *Staphylococcus aureus* (MRSA).

Thus, there is a need for immunostimulatory compositions and methods for eliciting non-specific immune responses against pathogens. The disclosed methods and compositions are directed to these and other important needs.

SUMMARY OF THE INVENTION

Disclosed herein are immunostimulatory compositions comprising an immunomodulator composition comprising a nucleic acid plasmid and a liposomal delivery vehicle; and an immunostimulatory oligonucleotide having at least one CpG motif and a guanine nucleotide-enriched sequence at or near the 5' terminus of the immunostimulatory oligonucleotide Also disclosed herein are methods for preparing an immunostimulatory composition comprising combining an immunomodulator composition comprising a nucleic acid plasmid and an immunostimulatory oligonucleotide to form an immunostimulatory composition, centrifuging the immunostimulatory composition to generate a supernatant and a pellet; and isolating the pellet.

Further provided are methods of stimulating TLR21 comprising administering an immunostimulatory oligonucleotide and an immunomodulator composition to a subject, wherein the immunostimulatory oligonucleotide comprises at least one CpG motif and a guanine nucleotide enriched sequence at or near the 5' terminus of the immunostimulatory oligonucleotide, and wherein the immunomodulator composition comprises a noncoding nucleic acid plasmid and a cationic lipid delivery vehicle.

Methods are also disclosed for eliciting an immune response in a subject by administering an immunostimulatory oligonucleotide and an immunomodulator composition, or an immunostimulatory composition comprising an immunostimulatory oligonucleotide and an immunomodulator composition, to a subject, wherein the immunostimulatory oligonucleotide has at least one CpG motif and a guanine nucleotide enriched sequence at or near the 5' terminus of the immunostimulatory oligonucleotide, and wherein the immunomodulator composition comprises a noncoding nucleic acid plasmid and a cationic lipid delivery vehicle

BRIEF DESCRIPTION OF THE DRAWINGS

The summary, as well as the following detailed description, is further understood when read in conjunction with the appended drawings. For the purpose of illustrating the disclosed compositions and methods, there are shown in the drawings exemplary embodiments of the compositions and methods; however, the compositions and methods are not limited to the specific embodiments disclosed. In the drawings:

FIG. 2A compares the immunogenicities of an immunostimulatory plasmid DNA ("pDNA") and pDNA complexed with cationic liposomes ("pDNA-F"). FIG. 2B compares the immunogenicities of pDNA, pDNA- F, and immunostimulatory oligonucleotide GCGT3-TG4T having a 5'-cholesteryl modification ("5Chol-GCGT3-TG4T").

FIG. 3A compares the immunogenicities of pDNA, pDNA-F, 5Chol-GCGT3-TG4T, pDNA combined with 5'Chol-GCGT3-TG4T ("pDNA-5Chol-GCGT3-TG4T"), and pDNA-F combined with 5Chol-GCGT3-TG4T ("pDNA-F-5Chol-GCGT3-TG4T"), wherein the immunostimulatory oligonucleotides are at nM concentrations and pDNA and pDNA-F are at µg/ml concentrations. FIG. 3B depicts the differences in immunogenicity between pDNA, pDNA-F, 5Chol-GCGT3-TG4T, pDNA combined with 5'Chol-GCGT3-TG4T ("pDNA-5Chol-GCGT3-TG4T"), and pDNA-F combined with 5Chol-GCGT3-TG4T ("pDNA-F-5Chol-GCGT3-TG4T"), wherein the immunostimulatory oligonucleotides are at pM concentrations and pDNA and pDNA-F are at ng/ml concentrations;

DETAILED DESCRIPTION OF ILLUSTRATIVE EMBODIMENTS

Figure 1:
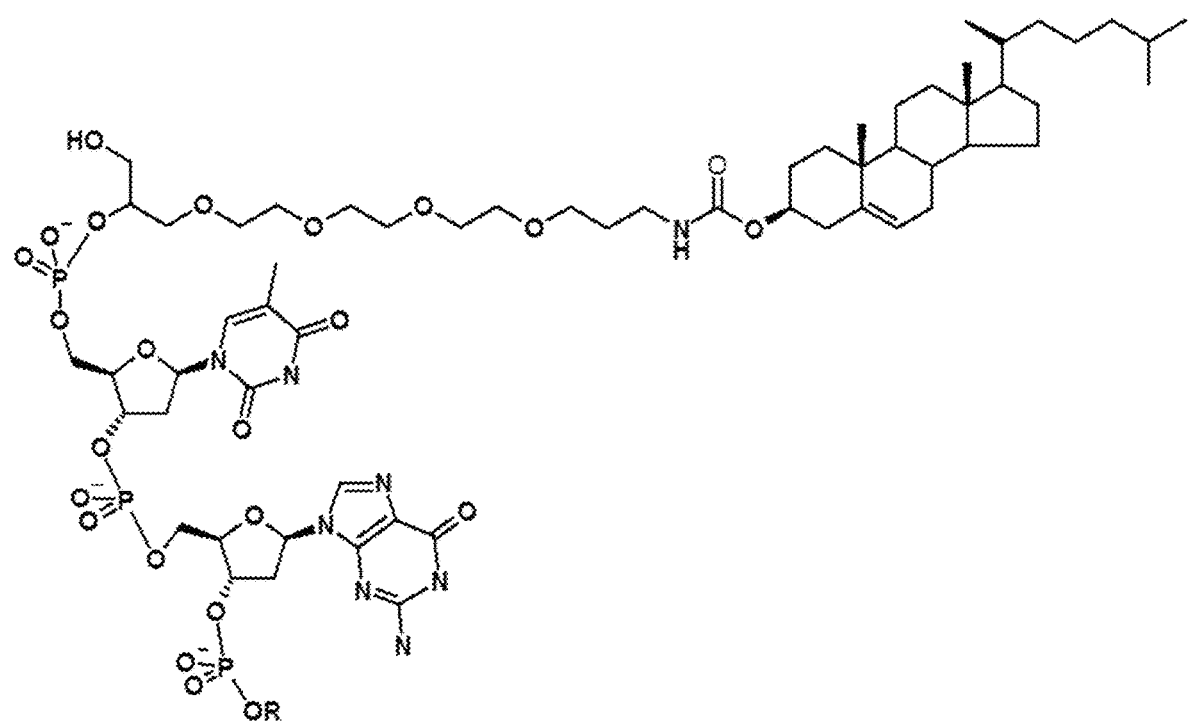
FIG. 1 illustrates the chemical structure of a cholesteryl moiety attached to a tetraethylene glycol linker.

The disclosed compositions and methods may be understood more readily by reference to the following detailed description taken in connection with the accompanying figures, which form a part of this disclosure. It is to be understood that the disclosed compositions and methods are not limited to the specific compositions and methods described and/or shown herein, and that the terminology used herein is for the purpose of describing particular embodiments by way of example only and is not intended to be limiting of the claimed compositions and methods.

Unless specifically stated otherwise, any description as to a possible mechanism or mode of action or reason for improvement is meant to be illustrative only, and the disclosed compositions and methods are not to be constrained by the correctness or incorrectness of any such suggested mechanism or mode of action or reason for improvement.

Throughout this text, the descriptions refer to compositions and methods of using said compositions. Where the disclosure describes or claims a feature or embodiment associated with a composition, such a feature or embodiment is equally applicable to the methods of using said composition. Likewise, where the disclosure describes or claims a feature or embodiment associated with a method of using a composition, such a feature or embodiment is equally applicable to the composition.

When a range of values is expressed, another embodiment includes from the one particular value and/or to the other particular value. Further, reference to values stated in ranges include each and every value within that range. All ranges are inclusive and combinable. When values are expressed as approximations, by use of the antecedent "about," it will be understood that the particular value forms another embodiment. Reference to a particular numerical value includes at least that particular value, unless the context clearly dictates otherwise.

It is to be appreciated that certain features of the disclosed compositions and methods which are, for clarity, described herein in the context of separate embodiments, may also be provided in combination in a single embodiment. Conversely, various features of the disclosed compositions and methods that are, for brevity, described in the context of a single embodiment, may also be provided separately or in any subcombination.

As used herein, the singular forms "a," "an," and "the" include the plural.

"Co-administered" as used herein refers to administering the immunomodulatory composition in combination with the immunostimulatory oligonucleotide to achieve the desired immunostimulatory effect. The immunomodulatory composition and the immunostimulatory oligonucleotide can be co-administered as separate compositions or together as a single composition. If the immunomodulatory composition and the immunostimulatory oligonucleotide are separate compositions, they can be co-administered either simultaneously or sequentially in either order. For sequential co-administration, there may be a delay of a minute, an hour, or even one or more days between the administration of the immunomodulatory composition and the immunostimulatory oligonucleotide.

As used herein, "fusing" refers to creating a chemical bond between two chemically reactive species. In the context of this disclosure, fusing most often refers to incorporating specific elements into an oligonucleotide. For example, a run of thymine nucleotides can be fused to the 3' end of an oligonucleotide.

As used herein, "G-quartet sequence" refers to a stretch of consecutive guanine residues near the 5' end of an oligonucleotide that enables the oligonucleotide to interact with other G-quartet sequences to form a G-quartet. The G-quartet enhances the immunostimulatory properties of the nucleic acid. For example, oligonucleotides comprising G-quartet sequences may interact, resulting in G-quartets. G-quartet sequences occurring in the promoter region of a gene may form quaternary structures involved in regulating the expression of the gene. While a G-quartet sequence is not limited to any particular sequence, an example of a G-quartet sequence is TGGGGT.

As used herein, "G-wire sequence," "G wire sequence," "Gwire sequence," and related terms, refer to a plurality, most often two, of at least four consecutive guanine nucleotides. The pluralities of guanine nucleotides, located at or near the 5' terminus of an oligonucleotide, are separated by two or more non-guanine nucleotides (i.e., thymine). G-wire sequences are capable of interacting with other G-wire sequences to form a G-wire structure. A G-wire structure can enhance the immunostimulatory properties of a nucleic acid. An exemplary G-wire sequence is GGGGTTGGGG (SEQ ID NO: 257) or GGGGTTGGGGTTTT (SEQ ID NO: 258).

As used herein, the terms "guanine nucleotide enriched sequence," "guanine enriched sequence," and the like, refer to sequences comprising either a run of consecutive guanine nucleotides, usually between four to six guanine nucleotides, or a region of a nucleic acid, typically at or near the 5' end of an oligonucleotide having more guanine nucleotides than adenine, cytosine, or thymine nucleotides. A guanine enriched sequence as disclosed herein can enhance the immunostimulatory properties of an oligonucleotide. G-quartet and G-wire sequences are both types of guanine nucleotide enriched sequences.

The term "immunomodulatory composition" as used herein refers to a composition comprising at least an immunogenic nucleic acid plasmid and a liposomal delivery vehicle. In some aspects of the presently disclosed compositions and methods, the nucleic acid plasmid may not code for a particular immunogen and may be immunogenic based on the inherent properties of the nucleic acid plasmid. In some aspects, the liposomal delivery vehicle is cationic.

An "immunogenic nucleic acid plasmid" is a nucleic acid plasmid that, when detected by a vertebrate immune system, elicits an immune response. Some immunogenic nucleic acid plasmids comprise an increased percentage of CpG dinucleotide motifs compared to nucleic acid plasmid sequences naturally occurring in some vertebrate organisms. Without being bound to theory, it is believed that increased CpG dinucleotide motifs are present in bacterially derived nucleic acid, and therefore, such CpG-enriched nucleic acid appears foreign to host immune defenses. Immunogenic nucleic acid plasmids can comprise non-naturally occurring nucleotides and derivatives of nucleotides.

"Immunostimulatory composition" as used herein refers to a composition comprising an immunomodulatory composition and an immunostimulatory oligonucleotide. In some aspects, the immunostimulatory oligonucleotide and the immunomodulatory composition comprise a single formulation that is the immunostimulatory composition. In some aspects, the immunostimulatory oligonucleotide may be physically associated with the liposomal delivery vehicle of the immunomodulatory composition.

As used herein, "inserting" refers to adding specific nucleotide(s) at specific positions during the synthesis of an oligonucleotide.

As used herein, "parallel orientation" refers to the directional interaction between different oligonucleotides. For example, individual oligonucleotides oriented in the same 5' to 3' direction are in a parallel orientation.

As used herein, "percent identity" and like terms are used to describe the sequence relationships between two or more nucleic acids, polynucleotides, proteins, or polypeptides, and are understood in the context of and in conjunction with the terms including: (a) reference sequence, (b) comparison window, (c) sequence identity and (d) percentage of sequence identity.

(a) A "reference sequence" is a defined sequence used as a basis for sequence comparison. A reference sequence may be a subset of or the entirety of a specified sequence; for example, a segment of a full-length cDNA or gene sequence, or the complete cDNA or gene sequence.

(b) A "comparison window" includes reference to a contiguous and specified segment of a polynucleotide sequence, wherein the polynucleotide sequence may be compared to a reference sequence and wherein the portion of the polynucleotide sequence in the comparison window may comprise additions, substitutions, or deletions (i.e., gaps) compared to the reference sequence (which does not comprise additions, substitutions, or deletions) for optimal alignment of the two sequences. Those of skill in the art understand that to avoid a misleadingly high similarity to a reference sequence due to inclusion of gaps in the polynucleotide sequence a gap penalty is typically introduced and is subtracted from the number of matches.

(c) Methods of alignment of sequences for comparison are well known in the art. Optimal alignment of sequences for comparison may be conducted by the local homology algorithm of Smith and Waterman, Adv. Appl. Math., 2: 482, 1981; by the homology alignment algorithm of Needleman and Wunsch, J. Mol. Biol., 48: 443, 1970; by the search for similarity method of Pearson and Lipman, Proc. Natl. Acad. Sci. USA, 8: 2444, 1988; by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 7 Science Dr., Madison, Wis., USA; the CLUSTAL program is well described by Higgins and Sharp, Gene, 73: 237-244, 1988; Corpet, et al., Nucleic Acids Research, 16:881-90, 1988; Huang, et al., Computer Applications in the Biosciences, 8:1-6, 1992; and Pearson, et al., Methods in Molecular Biology, 24:7-331, 1994. The BLAST family of programs which may be used for database similarity searches includes: BLASTN for nucleotide query sequences against nucleotide database sequences; BLASTX for nucleotide query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York, 1995. New versions of the above programs or new programs altogether will undoubtedly become available in the future, and may be used with the present disclosure.

(d) "Percent identity" means the value determined by comparing two optimally aligned sequences over a comparison window, wherein the portion of the polynucleotide sequence in the comparison window may comprise additions, substitutions, or deletions (i.e., gaps) as compared to the reference sequence (which does not comprise additions, substitutions, or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

"Therapeutically effective amount" refers to an amount of an immunomodulatory composition and/or an immunostimulatory oligonucleotide or of an immunostimulatory composition that treats the subject.

"Synergistically effective amount" refers to an amount of an immunomodulatory composition and an immunostimulatory oligonucleotide that provides a synergistic, or more than additive, effect in treating the subject. The term "subject" as used herein is intended to mean any animal, but in particular, avian species. "Avian species" includes, but is not limited to, chickens, domestic turkeys, waterfowl and any other food source fowl.

As used herein, "treating" and like terms refer to reducing the severity and/or frequency of symptoms of an infection, eliminating symptoms and/or the underlying cause of said symptoms, reducing the frequency or likelihood of symptoms and/or their underlying cause, and/or improving or remediating damage caused, directly or indirectly, by an infectious agent.

Various terms relating to aspects of the description are used throughout the specification and claims. Such terms are to be given their ordinary meaning in the art unless otherwise indicated. Other specifically defined terms are to be construed in a manner consistent with the definitions provided herein.

Immunostimulatory compositions are provided herein comprising an immunomodulator composition comprising a nucleic acid plasmid and a liposomal delivery vehicle and an immunostimulatory oligonucleotide having at least one CpG motif and an guanine nucleotide enriched sequence at or near the 5' terminus of the immunostimulatory oligonucleotide.

Immunostimulatory oligonucleotides, as described herein, can interact with TLR21 to elicit an immune response. The immunostimulatory oligonucleotides comprise at least one unmethylated dinucleotide CpG motif, which interacts with pathogen recognition receptors expressed in the host organism. The immunostimulatory oligonucleotides also have a guanine nucleotide enriched sequence. These sequences can facilitate the folding of a DNA strand into a quaternary structure or promote the aggregation of one or more immunostimulatory oligonucleotides that have an enhanced guanine the sequence. The guanine enriched sequence need not be comprised solely of guanine nucleotides, but it must be enriched. A guanine enriched sequence, as described supra and exemplified throughout these disclosures, typically is located at or near (within four nucleotides of) the oligonucleotide terminus. Additional manipulation of the oligonucleotide sequence and structure can further enhance the immunostimulatory oligonucleotide's ability to stimulate TLR21. Therefore, one embodiment of the present disclosure comprises an immunostimulatory composition comprising at least one immunostimulatory oligonucleotide having at least one CpG motif and a guanine enriched sequence beginning at or within four nucleotides of the 5' terminus of the immunostimulatory oligonucleotide.

In some aspects of the present disclosure, the addition of guanine nucleotide runs to the 5' end of the CpG containing immunostimulatory oligonucleotide can significantly improve immunogenicity of the immunostimulatory oligonucleotide. Not only does the position of the guanine rich sequence in the immunostimulatory oligonucleotide affect enhancement of TLR21 activation, but the content of the sequence has an effect as well. For this reason, in some aspects of the present disclosure, guanine enriched sequences comprise a plurality of consecutive guanine nucleotides.

In some embodiments, the guanine enriched sequence comprises a first plurality of consecutive guanine nucleotides. In some aspects the first plurality of guanine nucleotides comprises two to eight guanine nucleotides. In some aspects, the first plurality of guanine nucleotides comprises two guanine nucleotides. In some aspects, the first plurality of guanine nucleotides comprises three guanine nucleotides. In some aspects, the first plurality of guanine nucleotides comprises four guanine nucleotides. In some aspects, the first plurality of guanine nucleotides comprises five guanine nucleotides. In some aspects, the first plurality of guanine nucleotides comprises six guanine nucleotides. In some aspects, the first plurality of guanine nucleotides comprises seven guanine nucleotides. In some aspects, the first plurality of guanine nucleotides comprises eight guanine nucleotides. In still other aspects, the first plurality of guanine nucleotides comprises more than eight guanine nucleotides.

In some embodiments of the present invention, the oligonucleotide comprises SEQ ID NO:16, 17, 18, 19, 20, 21, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 77, 78, 81, 82, 85, 86, 89, 90, 92, 93, 96, 97, 100, 102, 104, 106, 108, or 143. In other embodiments, the guanine enriched sequence comprises TTAGGG, TTAGGGTTAGGG (SEQ ID NO:261), TTTTGGGG, GGGGTTTT, GGGGTTTTGGGG (SEQ ID NO:262), TTAGGG, TTAGGGTTAGGGTTTT (SEQ ID NO:263), TGTGGGTGTGTGTGGG (SEQ ID NO:269), GGAGG, TGGAGGC, or TGGAGGCTGGAGGC (SEQ ID NO:264). In still other embodiments, the oligonucleotide comprises SEQ ID NO:110, 111, 112, 113, 114, 115, 116, 117, 118, 119, 120, 124, 125, 126, 127, 129, 130, 131, 134, 136, 137, or 138.

A single run of guanine nucleotides is not the only 5' modification that can enhance TLR21 stimulation. For example, adenine, cytosine, and thymine enriched sequences can also be added to the 5' end of an oligonucleotide having CpG motif and result in enhanced TLR21 stimulation, albeit less than that elicited by the guanine enriched sequences at the 5' end of the oligonucleotide. While a single plurality of guanine residues at the 5' end of the oligonucleotide can elicit TLR21 stimulation, additional pluralities of guanine nucleotides in the guanine enriched sequence may further enhance the stimulatory properties of the oligonucleotide. Thus, in some aspects, the oligonucleotide of the present disclosure comprises a second plurality of guanine nucleotides between the first plurality of guanine nucleotides and the at least one CpG motif.

In some aspects, a plurality of guanine nucleotides comprises a G-quartet sequence. In some embodiments, the first plurality of guanine nucleotides, the second plurality of guanine nucleotides, or both comprise a G-quartet sequence. G-quartet sequences, as defined above, also allow for interaction between oligonucleotides. Without being bound by theory, interaction at the 5' end of the oligonucleotides allows for the concentration of CpG dinucleotide motifs and a corresponding enhanced opportunity for recognition by TRL21. In some embodiments, the immunostimulatory composition further comprises at least one additional oligonucleotide having a G-quartet sequence, wherein the oligonucleotide and the at least one additional oligonucleotide have a parallel orientation in a quaternary structure. In some aspects, the G-quartet sequence comprises TGGGGT.

Another guanine enriched sequence that can be added at or near the 5' terminus of an oligonucleotide having CpG motifs is a G-wire sequence. In some aspects of the present disclosure, the first and second pluralities of guanine nucleotides comprise a G-wire sequence. In some aspects, the G-wire sequence comprises SEQ ID NO:257 or 258. In still other aspects, the G-wire sequence comprises SEQ ID NO:141, 142, 176, 177, 178, 179, 180, 181, 182, 183, 184, 185, 186, 187, 188, 189, 192, 193, 194, 195, 196, 197, 198, 199, 200, 201, 202, 203, or GCGT-Gwire3. The two pluralities of guanine nucleotides can be separated by non-guanine nucleotides, nucleotide analogs, or any other spacer or linker. For example, in some aspects of the present disclosure, the first plurality of guanine nucleotides and the second plurality of guanine nucleotides are separated by at least one nucleotide. As used herein, the term "spacer" refers to a chemical linkage between similar nucleotide motifs, i.e., between two CpG motifs or between two guanine nucleotide enriched sequence motifs, whereas the term "linker" refers to a chemical linkage between different nucleotide motifs, i.e., between a guanine nucleotide enriched sequence and another nucleotide motif, e.g., a CpG motif. The terms "spacer" and "linker" are used for clarity in describing which aspect of an oligonucleotide is being discussed. However, it will be understood by those skilled in the art that the structures disclosed herein for spacers can be interchangeable with the structures disclosed herein for linkers, and vice versa.

Without being bound by any particular theory, it is possible that the G-wire sequence enables an oligonucleotide to interact and aggregate with other oligonucleotides having G-wire sequences. The conformation assumed by the aggregation of oligonucleotides having G-wire sequences is referred to as G-wire conformation, and this accumulation of oligonucleotides and their CpG motifs can lead to enhanced stimulation of TLR21.

The guanine enriched sequences may be separated from the CpG nucleotide motifs by nucleotides, nucleotide analogs, or other linkers. Therefore, in some embodiments of the present disclosure, the oligonucleotide further comprises a linker between the guanine enriched sequence and the downstream at least one CpG motif. As used herein, "downstream" means in the 5'→3' direction; i.e., a "downstream" nucleotide or motif is a nucleotide or motif that is 3' of a comparison sequence element. "Upstream" means in the 3'→5' direction; i.e., an "upstream" nucleotide or motif is a nucleotide or motif that is 5' of a comparison sequence element. The linker need not be directly adjacent to either the guanine enriched sequence or the CpG motif; rather, the linker must reside between the two sequence motifs regardless of intervening sequences between the guanine enriched sequence and the linker, as well as between the CpG motif and the linker. In some embodiments of the present disclosures, the linker comprises at least three nucleotides. The linker also may not comprise nitrogenous bases. For example, in some aspects, the linker is a hexaethyleneglycol, a propanediol, a triethyleneglycol, or derivatives thereof. In other examples, the oligonucleotide having a linker comprises 2006-PDE5dG4-X1 or 2006-PDE5dG4-X3.

Dinucleotide CpG motifs present in the oligonucleotides of the present disclosure are believed to be PAMPs recognized by TLR21 in chickens. While even a single CpG motif can stimulate TLR21, multiple CpGs present on an oligonucleotide can increase stimulated TLR21 signal strength. For this reason, in some aspects of the present invention, the at least one CpG motif comprises two, three, four, or five CpG motifs. In some aspects the at least one CpG motif comprises six or more CpG motifs. In some aspects, the at least one CpG motif comprises two CpG motifs. In some aspects, the at least one CpG motif comprises three CpG motifs. In some aspects, the at least one CpG motif comprises four CpG motifs. In some embodiments, the at least one CpG motif comprises four CpG motifs.

In some embodiments of the presently disclosed oligonucleotides, each CpG motif may be separated from the other CpG motifs by at least one nucleotide or nucleotide analog. In some aspects, the at least one nucleotide is two or three thymine nucleotides. In other aspects, the at least one nucleotide is between one and four nucleotides, although the number of intervening nucleotides may differ depending on the sequence of the intervening nucleotides. In some aspects, the oligonucleotide comprises SEQ ID NO:217, 218, 219, or 220. The nucleotides adjacent to a CpG—along with the CpG motif itself—constitute a CpG sequence element (e.g., XCGX, where X=any nucleotide). The oligonucleotides of the present disclosure, in some aspects comprise CpG sequence elements that are GCGA, GCGG, ACGC, CCGC, GCGT, TCGC, or any combination thereof.

In some embodiments of the present disclosures, the CpG motif comprises a CpG sequence element having four nucleotides. In some aspects, the oligonucleotide comprises at least two CpG sequence elements. In some aspects, the oligonucleotide comprises at least three CpG sequence elements. In some aspects, the oligonucleotide comprises at least four CpG sequence elements. In some aspects, the oligonucleotide comprises at least five CpG sequence elements. In some aspects, the oligonucleotide comprises at least six CpG sequence elements. In some aspects, the oligonucleotide comprises more than eight, ten, fifteen, or even twenty CpG sequence elements.

In other embodiments of the presently disclosed oligonucleotides, each of the CpG motifs are separated from every other CpG motif by a spacer or a combination of a spacer and at least one nucleotide. In some aspects, at least one CpG motif is separated from the nearest other CpG motif by a spacer or a combination of a spacer and at least one nucleotide, while at least two other CpG motifs are adjacent to each other. Although separated CpG motifs may enhance the immunostimulatory capabilities of the designed oligonucleotides, it is acknowledged that CpG motifs adjacent to each other can still stimulate TLR21.

The spacer employed to linearly separate CpG motifs can be any linkage that bridges at least a portion of the oligonucleotide between the CpG motifs. The spacer may be comprised of, but not necessarily limited to, a deoxyribose phosphate bridge, a multiple carbon chain, or a repeated chemical unit. One essential property of a spacer is the ability to form a chemical bond with the nucleotide backbone of the oligonucleotide. Therefore, in some embodiments the spacer is a deoxyribose phosphate bridge. The deoxyribose phosphate bridge may comprise nitrogenous bases in some aspects while in others the deoxyribose phosphate bridge is abasic. In some aspects, the oligonucleotide comprises SEQ ID NO:221, which comprises an abasic deoxyribose phosphate bridge.

In other embodiments of the present disclosure, the spacer comprises a carbon chain. The carbon chain can comprise two to twelve carbon atoms. Diols comprising a carbon chain can be used as the terminal alcohol groups can react with terminal alcohol and/or phosphate groups of an oligonucleotide. In some embodiments, the carbon chain comprises two carbon atoms, and in some aspects, the carbon chain is derived from ethanediol. In some embodiments, the oligonucleotide comprises ODN-X2, wherein X2 is ethanediol.

Other embodiments of the present disclosure provide for the carbon chain comprising three carbon atoms. In some aspects of these embodiments, the carbon chain is derived from 1,3-propanediol. In some embodiments, the oligonucleotide comprises CG-Gw2X2, CG-Gw2X2-2, or ODN-X3, CG-Gw2X2-1, CG-Gw2X2-3, CG-Gw2X2-4, CG-Gw2X2-5, CG-G4T16X2-1, CG-G4T16X2-2, CG-G4T16X2-3, CG-G4T16X2-4, or CG-G4T16X2-5, wherein X2 is a three carbon chain; 2006-PDE5dG4-X2 wherein X2 is a three carbon chain derived from propanediol; or SEQ ID NO:250, wherein X4 is a three carbon chain derived from propanediol.

In yet other embodiments of the present disclosure the oligonucleotide comprises a carbon chain spacer, wherein the carbon chain comprises four carbon atoms. In some aspects of these embodiments, the carbon chain is derived from 1,4-butanediol. In some embodiments, the oligonucleotide comprises ODN-X4, wherein X4 is a four carbon chain derived from 1,4-butanediol.

In still other embodiments of the present disclosures, the oligonucleotide comprises a spacer having a repeated chemical unit. For example, in some embodiments, the repeated chemical unit is an ethylene glycol. The repeated chemical unit may be repeated two to twelve times. In some embodiments, ethylene glycol is repeated six times. Thus, in some aspects, the oligonucleotide comprises CCGC-Gw2X1, wherein X1 is a spacer derived from hexaethyleneglycol.

Although guanine nucleotide runs on the 3' terminus of an oligonucleotide results in little, if any, TLR21 stimulation, other nucleotide runs can impart enhanced immunogenicity to the oligonucleotide. Specifically, in some aspects of the present disclosures, the oligonucleotide may further comprise a tri-thymine nucleotide 3' terminal end. In some aspects, the oligonucleotide comprises SEQ ID NO:204, 205, 206, 207, 208, 209, 210, 211, 212, 213, 214, or 215.

For each oligonucleotide disclosed herein, one skilled in the art would know that a nucleotide can be substituted with a nucleotide analog. The oligonucleotides in some embodiments comprise a phosphodiester backbone, although other embodiments of the oligonucleotides disclosed herein comprise a phosphorothioate backbone. Phosphorothioate backbones may, in some circumstances, be easier and more cost effective to manufacture.

In some embodiments of the present disclosure, the oligonucleotide may comprise a lipid moiety, which can lead to an increase in the oligonucleotide's immunogenicity. One possible explanation for the increased immunogenicity is that the lipid moiety may function to enhance the bioavailability of the oligonucleotide. In some embodiments, the lipid moiety is at or near the 5' terminus of the oligonucleotide. This lipid "cap" may prevent degradation, increase solubility, improve the oligonucleotide's stability in a pharmaceutical composition, or any combination thereof. In some aspects, the lipid moiety is a cholesteryl.

The potency of the immunostimulatory oligonucleotide and the immunostimulatory composition can be characterized by their half-maximum effective concentration ($EC_{50}$), which is a measurement of the concentration necessary to induce a response that is half of the maximum response that can be attained by administering the composition. The lower the concentration, the more potent the oligonucleotide. In some aspects of the present disclosures, the immunostimulatory composition can have an $EC_{50}$ in the pM range. In some aspects, the $EC_{50}$ is between about 0.1 and 100 pM. In some aspects, the $EC_{50}$ is between about 100 and 200 pM. In some aspects the $EC_{50}$ is between about 200 and 300 pM. In some aspects, the $EC_{50}$ is between about 300 and 400 pM. In some aspects the $EC_{50}$ is between about 400 and 500 pM. In some aspects the $EC_{50}$ is between about 500 and 600 pM. In some aspects the $EC_{50}$ is between about 600 and 700 pM. In some aspects the $EC_{50}$ is between about 700 and 800 pM. In some aspects the $EC_{50}$ is between about 800 and 900 pM. In some aspects the $EC_{50}$ is between about 900 and 1 nM. In still other aspects, the $EC_{50}$ is less than about 100 pM.

Regarding the concentration of the oligonucleotide in the immunostimulatory composition, in some aspects the concentration of the oligonucleotide is between about 0.1 and 10 nM. In some aspects, the concentration of the oligonucleotide is between about 10 and 20 nM. In some aspects the concentration of the oligonucleotide is between about 20 and 30 nM. In some aspects, the concentration of the oligonucleotide is between about 30 and 40 nM. In some aspects the concentration of the oligonucleotide is between about 40 and 50 nM. In some aspects the concentration of the oligonucleotide is between about 50 and 60 nM. In some aspects the concentration of the oligonucleotide is between about 60 and 70 nM. In some aspects the concentration of the oligonucleotide is between about 70 and 80 nM. In some aspects the concentration of the oligonucleotide is between about 80 and 90 nM. In some aspects the concentration of the oligonucleotide is between about 90 and 100 nM. In still other aspects, the concentration of the oligonucleotide is less than about 20 nM.

The immunostimulatory composition may further comprise at least one additional oligonucleotide having a G-wire sequence in some embodiments of the present disclosure. Because the G-wire sequence facilitates the aggregation of other oligonucleotides having the same, or similar, G-wire sequence, one aspect of the immunostimulatory composition further comprises at least one additional oligonucleotide having a G-wire sequence. In some aspects in which the immunostimulatory composition comprises multiple oligonucleotides having G-wire sequences, the oligonucleotide and the at least one additional oligonucleotide have a G-wire conformation.

The ability of an oligonucleotide to stimulate TLR21 may be further enhanced according to some aspect of the invention by inserting additional CpG motifs. In some aspects, the at least one CpG motif is a plurality of CpG motifs, and the plurality of CpG motifs comprises two, three, four, or five CpG motifs. Distance between the CpG motifs can influence the oligonucleotide's TLR21 stimulatory properties. For this reason, some aspects of the disclosed oligonucleotides provide for insertion of at least one nucleotide or nucleotide analog between the CpG motifs. The at least one nucleotide may be two or three thymine nucleotides.

Other embodiments provide for inclusion of a spacer between each of the CpG motifs. The spacer must be able to bond to the 3' terminus of one adjacent nucleotide strand and to the 5' end of the other nucleotide strand. In some aspects, the spacer is a deoxyribose phosphate bridge, which can be abasic in some aspects.

The spacer, in some aspects, may comprise a carbon chain. In some embodiments the carbon chain comprises two carbon atoms. In some aspects the carbon chain is derived from ethanediol. Other embodiments provide for a carbon chain comprising three carbon atoms. In some aspects, the carbon chain is derived from 1,3-propanediol. In some embodiments, the carbon chain comprises four carbon atoms, and in some aspects the carbon chain is derived from 1,4-butanediol. In still other embodiments, the spacer comprises a repeated chemical unit. In some aspects, the repeated chemical unit is an ethylene glycol, and in some aspects the spacer is derived from hexaethyleneglycol.

Representative oligonucleotides of the present disclosure are identified in Table 1.

TABLE 1

| Oligonucleotide sequences | | |
|---|---|---|
| 5Chol-GCGT3-TG4T | SEQ ID NO: 1 | XTGGGGTTTTTTTGCGTTTTTGCGTTTTTGCGTTTT<br>X = 5'-Cholesteryl |
| 2006-PTO | SEQ ID NO: 3 | tcgtcgttttgtcgttttgtcgtt |
| 2006-PDE | SEQ ID NO: 4 | TCGTCGTTTTGTCGTTTTGTCGTT |
| 2006-PDE3dG1 | SEQ ID NO: 5 | TCGTCGTTTTGTCGTTTTGTCGTTG |
| 2006-PDE3dG2 | SEQ ID NO: 6 | TCGTCGTTTTGTCGTTTTGTCGTTGG |
| 2006-PDE3dG3 | SEQ ID NO: 7 | TCGTCGTTTTGTCGTTTTGTCGTTGGG |
| 2006-PDE3dG4 | SEQ ID NO: 8 | TCGTCGTTTTGTCGTTTTGTCGTTGGGG |
| 2006-PDE3dG5 | SEQ ID NO: 9 | TCGTCGTTTTGTCGTTTTGTCGTTGGGGG |
| 2006-PDE3dG6 | SEQ ID NO: 10 | TCGTCGTTTTGTCGTTTTGTCGTTGGGGGG |
| 2006-PDE3dG7 | SEQ ID NO: 11 | TCGTCGTTTTGTCGTTTTGTCGTTGGGGGGG |
| 2006-PDE3dG8 | SEQ ID NO: 12 | TCGTCGTTTTGTCGTTTTGTCGTTGGGGGGGG |
| 2006-PTO | SEQ ID NO: 3 | tcgtcgttttgtcgttttgtcgtt |
| 2006-PDEV3 | SEQ ID NO: 13 | TCGTCGTTTTGTCGTTTTGTCGTT |
| 2006-PDE5dG1 | SEQ ID NO: 14 | GTCGTCGTTTTGTCGTTTTGTCGTT |

TABLE 1-continued

Oligonucleotide sequences

| | | |
|---|---|---|
| 2006-PDE5dG2 | SEQ ID NO: 15 | GGTCGTCGTTTTGTCGTTTTGTCGTT |
| 2006-PDE5dG3 | SEQ ID NO: 16 | GGGTCGTCGTTTTGTCGTTTTGTCGTT |
| 2006-PDE5dG4 | SEQ ID NO: 17 | GGGGTCGTCGTTTTGTCGTTTTGTCGTT |
| 2006-PDE5dG5 | SEQ ID NO: 18 | GGGGGTCGTCGTTTTGTCGTTTTGTCGTT |
| 2006-PDE5dG6 | SEQ ID NO: 19 | GGGGGGTCGTCGTTTTGTCGTTTTGTCGTT |
| 2006-PDE5dG7 | SEQ ID NO: 20 | GGGGGGGTCGTCGTTTTGTCGTTTTGTCGTT |
| 2006-PDE5dG8 | SEQ ID NO: 21 | GGGGGGGGTCGTCGTTTTGTCGTTTTGTCGTT |
| 2006-PDE5dA6 | SEQ ID NO: 22 | AAAAAATCGTCGTTTTGTCGTTTTGTCGTT |
| 2006-PDE5dC6 | SEQ ID NO: 23 | CCCCCCTCGTCGTTTTGTCGTTTTGTCGTT |
| 2006-PDE5dT6 | SEQ ID NO: 24 | TTTTTTTCGTCGTTTTGTCGTTTTGTCGTT |
| 2006-PDE5dG6-Me | SEQ ID NO: 25 | GGGGGGTm5cGTm5cGTTTTGTm5cGTTTTGTm5cGTT<br>m5c = 5-methyl-cytidine |
| 2006-PDE5dC6-GC | SEQ ID NO: 26 | CCCCCCTGCTGCTTTTGTGCTTTTGTGCTT |
| 2006-PDE5dT6-CA | SEQ ID NO: 27 | TTTTTTTCATCATTTTGTCATTTTGTCATT |
| 2006-PTO3dG5 | SEQ ID NO: 28 | tggggGTCGTCGTTTTGTCGTTTTGTCGTT |
| 2006-PTO5dG6 | SEQ ID NO: 29 | tcgtcgttttgtcgttttgtcgttggggg |
| 2006-PDE5dG6-A1 | SEQ ID NO: 30 | AGGGGGTCGTCGTTTTGTCGTTTTGTCGTT |
| 2006-PDE5dG6-A2 | SEQ ID NO: 31 | GAGGGGTCGTCGTTTTGTCGTTTTGTCGTT |
| 2006-PDE5dG6-A3 | SEQ ID NO: 32 | GGAGGGTCGTCGTTTTGTCGTTTTGTCGTT |
| 2006-PDE5dG6-A4 | SEQ ID NO: 33 | GGGAGGTCGTCGTTTTGTCGTTTTGTCGTT |
| 2006-PDE5dG6-A5 | SEQ ID NO: 34 | GGGGAGTCGTCGTTTTGTCGTTTTGTCGTT |
| 2006-PDE5dG6-A6 | SEQ ID NO: 35 | GGGGGATCGTCGTTTTGTCGTTTTGTCGTT |
| 2006-PDE5dG6-A12 | SEQ ID NO: 36 | AAGGGGTCGTCGTTTTGTCGTTTTGTCGTT |
| 2006-PDE5dG6-A23 | SEQ ID NO: 37 | GAAGGGTCGTCGTTTTGTCGTTTTGTCGTT |
| 2006-PDE5dG6-A34 | SEQ ID NO: 38 | GGAAGGTCGTCGTTTTGTCGTTTTGTCGTT |
| 2006-PDE5dG6-A45 | SEQ ID NO: 39 | GGGAAGTCGTCGTTTTGTCGTTTTGTCGTT |
| 2006-PDE5dG6-A56 | SEQ ID NO: 40 | GGGGAATCGTCGTTTTGTCGTTTTGTCGTT |
| 2006-PDE5dG6-C1 | SEQ ID NO: 41 | CGGGGGTCGTCGTTTTGTCGTTTTGTCGTT |
| 2006-PDE5dG6-C2 | SEQ ID NO: 42 | GCGGGGTCGTCGTTTTGTCGTTTTGTCGTT |
| 2006-PDE5dG6-C3 | SEQ ID NO: 43 | GGCGGGTCGTCGTTTTGTCGTTTTGTCGTT |
| 2006-PDE5dG6-C4 | SEQ ID NO: 44 | GGGCGGTCGTCGTTTTGTCGTTTTGTCGTT |

TABLE 1-continued

Oligonucleotide sequences

| | | |
|---|---|---|
| 2006-PDE5dG6-C5 | SEQ ID NO: 45 | GGGGCGTCGTCGTTTTGTCGTTTTGTCGTT |
| 2006-PDE5dG6-C6 | SEQ ID NO: 46 | GGGGGCTCGTCGTTTTGTCGTTTTGTCGTT |
| 2006-PDE5dG6-C12 | SEQ ID NO: 47 | CCGGGGTCGTCGTTTTGTCGTTTTGTCGTT |
| 2006-PDE5dG6-C23 | SEQ ID NO: 48 | GCCGGGTCGTCGTTTTGTCGTTTTGTCGTT |
| 2006-PDE5dG6-C34 | SEQ ID NO: 49 | GGCCGGTCGTCGTTTTGTCGTTTTGTCGTT |
| 2006-PDE5dG6-C45 | SEQ ID NO: 50 | GGGCCGTCGTCGTTTTGTCGTTTTGTCGTT |
| 2006-PDE5dG6-C56 | SEQ ID NO: 51 | GGGGCCTCGTCGTTTTGTCGTTTTGTCGTT |
| 2006-PDE5dG6-T1 | SEQ ID NO: 52 | TGGGGGTCGTCGTTTTGTCGTTTTGTCGTT |
| 2006-PDE5dG6-T2 | SEQ ID NO: 53 | GTGGGGTCGTCGTTTTGTCGTTTTGTCGTT |
| 2006-PDE5dG6-T3 | SEQ ID NO: 54 | GGTGGGTCGTCGTTTTGTCGTTTTGTCGTT |
| 2006-PDE5dG6-T4 | SEQ ID NO: 55 | GGGTGGTCGTCGTTTTGTCGTTTTGTCGTT |
| 2006-PDE5dG6-T5 | SEQ ID NO: 56 | GGGGTGTCGTCGTTTTGTCGTTTTGTCGTT |
| 2006-PDE5dG6-T6 | SEQ ID NO: 57 | GGGGGTTCGTCGTTTTGTCGTTTTGTCGTT |
| 2006-PDE5dG6-T12 | SEQ ID NO: 58 | TTGGGGTCGTCGTTTTGTCGTTTTGTCGTT |
| 2006-PDE5dG6-T23 | SEQ ID NO: 59 | GTTGGGTCGTCGTTTTGTCGTTTTGTCGTT |
| 2006-PDE5dG6-T34 | SEQ ID NO: 60 | GGTTGGTCGTCGTTTTGTCGTTTTGTCGTT |
| 2006-PDE5dG6-T45 | SEQ ID NO: 61 | GGGTTGTCGTCGTTTTGTCGTTTTGTCGTT |
| 2006-PDE5dG6-T56 | SEQ ID NO: 62 | GGGGTTTCGTCGTTTTGTCGTTTTGTCGTT |
| 2006-PDE5dG4-A1 | SEQ ID NO: 63 | AGGGTCGTCGTTTTGTCGTTTTGTCGTT |
| 2006-PDE5dG4-A2 | SEQ ID NO: 64 | GAGGTCGTCGTTTTGTCGTTTTGTCGTT |
| 2006-PDE5dG4-A3 | SEQ ID NO: 65 | GGAGTCGTCGTTTTGTCGTTTTGTCGTT |
| 2006-PDE5dG4-A4 | SEQ ID NO: 66 | GGGATCGTCGTTTTGTCGTTTTGTCGTT |
| 2006-PDE5dG4-C1 | SEQ ID NO: 67 | CGGGTCGTCGTTTTGTCGTTTTGTCGTT |
| 2006-PDE5dG4-C2 | SEQ ID NO: 68 | GCGGTCGTCGTTTTGTCGTTTTGTCGTT |
| 2006-PDE5dG4-C3 | SEQ ID NO: 69 | GGCGTCGTCGTTTTGTCGTTTTGTCGTT |
| 2006-PDE5dG4-C4 | SEQ ID NO: 70 | GGGCTCGTCGTTTTGTCGTTTTGTCGTT |

TABLE 1-continued

Oligonucleotide sequences

| Name | SEQ ID | Sequence |
|---|---|---|
| 2006-PDE5dG4-T1 | SEQ ID NO: 71 | TGGGTCGTCGTTTTGTCGTTTTGTCGTT |
| 2006-PDE5dG4-T2 | SEQ ID NO: 72 | GTGGTCGTCGTTTTGTCGTTTTGTCGTT |
| 2006-PDE5dG4-T3 | SEQ ID NO: 73 | GGTGTCGTCGTTTTGTCGTTTTGTCGTT |
| 2006-PDE5dG4-T4 | SEQ ID NO: 74 | GGGTTCGTCGTTTTGTCGTTTTGTCGTT |
| 1668 | SEQ ID NO: 75 | TCCATGACGTTCCTGATGCT |
| 1668-3dG5 | SEQ ID NO: 76 | TCCATGACGTTCCTGATGCTGGGGG |
| 1668-5dG4 | SEQ ID NO: 77 | GGGGTCCATGACGTTCCTGATGCT |
| 1668-5dG6 | SEQ ID NO: 78 | GGGGGGTCCATGACGTTCCTGATGCT |
| 1826 | SEQ ID NO: 79 | TCCATGACGTTCCTGACGTT |
| 1826-3dG5 | SEQ ID NO: 80 | TCCATGACGTTCCTGACGTTGGGGG |
| 1826-5dG4 | SEQ ID NO: 81 | GGGGTCCATGACGTTCCTGACGTT |
| 1826-5dG6 | SEQ ID NO: 82 | GGGGGGTCCATGACGTTCCTGACGTT |
| BW006 | SEQ ID NO: 83 | TCGACGTTCGTCGTTCGTCGTTC |
| BW006-3dG5 | SEQ ID NO: 84 | TCGACGTTCGTCGTTCGTCGTTCGGGGG |
| BW006-5dG4 | SEQ ID NO: 85 | GGGGTCGACGTTCGTCGTTCGTCGTTC |
| BW006-5dG6 | SEQ ID NO: 86 | GGGGGGTCGACGTTCGTCGTTCGTCGTTC |
| D-SL01 | SEQ ID NO: 87 | TCGCGACGTTCGCCCGACGTTCGGTA |
| D-SL01-3dG5 | SEQ ID NO: 88 | TCGCGACGTTCGCCCGACGTTCGGTAGGGGG |
| D-SL01-5dG4 | SEQ ID NO: 89 | GGGGTCGCGACGTTCGCCCGACGTTCGGTA |
| D-SL01-5dG6 | SEQ ID NO: 90 | GGGGGGTCGCGACGTTCGCCCGACGTTCGGTA |
| 2395 | SEQ ID NO: 91 | TCGTCGTTTTCGGCGCGCGCCG |
| 2395-5dG4 | SEQ ID NO: 92 | GGGGTCGTCGTTTTCGGCGCGCGCCG |
| 2395-5dG6 | SEQ ID NO: 93 | GGGGGGTCGTCGTTTTCGGCGCGCGCCG |
| M362 | SEQ ID NO: 94 | TCGTCGTCGTTCGAACGACGTTGAT |
| M362-3dG5 | SEQ ID NO: 95 | TCGTCGTCGTTCGAACGACGTTGATGGGGG |
| M362-5dG4 | SEQ ID NO: 96 | GGGGTCGTCGTCGTTCGAACGACGTTGAT |
| M362-5dG6 | SEQ ID NO: 97 | GGGGGGTCGTCGTCGTTCGAACGACGTTGAT |
| 2007-PDE | SEQ ID NO: 98 | TCGTCGTTGTCGTTTTGTCGTT |
| 2007-PDE3dG5 | SEQ ID NO: 99 | TCGTCGTTGTCGTTTTGTCGTTGGGGG |
| 2007-PDE5dG6 | SEQ ID NO: 100 | GGGGGGTCGTCGTTGTCGTTTTGTCGTT |
| CPG-202 | SEQ ID NO: 101 | GATCTCGCTCGCTCGCTAT |
| CPG-202-5dG6 | SEQ ID NO: 102 | GGGGGGGATCTCGCTCGCTCGCTAT |
| CPG-685 | SEQ ID NO: 103 | TCGTCGACGTCGTTCGTTCTC |
| CPG-685-5dG6 | SEQ ID NO: 104 | GGGGGGTCGTCGACGTCGTTCGTTCTC |
| CPG-2000 | SEQ ID NO: 105 | TCCATGACGTTCCTGCAGTTCCTGACGTT |
| CPG-2000-5dG6 | SEQ ID NO: 106 | GGGGGGTCCATGACGTTCCTGCAGTTCCTGACGTT |
| CPG-2002 | SEQ ID NO: 107 | TCCACGACGTTTTCGACGTT |

TABLE 1-continued

Oligonucleotide sequences

| | | |
|---|---|---|
| CPG-2002-5dG6 | SEQ ID NO: 108 | GGGGGGTCCACGACGTTTTCGACGTT |
| 2006-T4-PDE | SEQ ID NO: 109 | TTTTTCGTCGTTTTGTCGTTTTGTCGTT |
| 2006-HuTel-1 | SEQ ID NO: 110 | TTAGGGTCGTCGTTTTGTCGTTTTGTCGTT |
| 2006-HuTel-2 | SEQ ID NO: 111 | TTAGGGTTAGGGTCGTCGTTTTGTCGTTTTGTCGTT |
| 2006-PDE-Oxy1 | SEQ ID NO: 112 | TTTTGGGGTCGTCGTTTTGTCGTTTTGTCGTT |
| 2006-PDE-Oxy2 | SEQ ID NO: 113 | GGGGTTTTCGTCGTTTTGTCGTTTTGTCGTT |
| 2006-PDE-Oxy3 | SEQ ID NO: 114 | GGGGTTTTGGGTCGTCGTTTTGTCGTTTTGTCGTT |
| 2006-T4-HuTel-1 | SEQ ID NO: 115 | TTAGGGTTTTCGTCGTTTTGTCGTTTTGTCGTT |
| 2006-T4-HuTel-2 | SEQ ID NO: 116 | TTAGGGTTAGGGTTTTCGTCGTTTTGTCGTTTTGTCGTT |
| 2006-T4-ScerTel | SEQ ID NO: 117 | TGTGGGTGTGTGGGTTTTCGTCGTTTTGTCGTTTTGTCGTT |
| 2006-T4-cMyc | SEQ ID NO: 118 | GGAGGTTTTCGTCGTTTTGTCGTTTTGTCGTT |
| 2006-T4-cMyc2 | SEQ ID NO: 119 | TGGAGGCTTTTCGTCGTTTTGTCGTTTTGTCGTT |
| 2006-T4-cMyc3 | SEQ ID NO: 120 | TGGAGGCTGGAGGCTTTTCGTCGTTTTGTCGTTTTGTCGTT |
| EA2-2006 | SEQ ID NO: 121 | GCTGCGAGGCGGGTGGGTGGGATCGTCGTTTTGTCGTTTTGTCGTT |
| EA2D-2006 | SEQ ID NO: 122 | GCTGCGGGCGGGTGGGTGGGATCGTCGTTTTGTCGTTTTGTCGTT |
| EA2a-2006 | SEQ ID NO: 123 | CGAGGCGGGTGGGTGGGATCGTCGTTTTGTCGTTTTGTCGTT |
| EA2aD-2006 | SEQ ID NO: 124 | CGGGCGGGTGGGTGGGATCGTCGTTTTGTCGTTTTGTCGT |
| HCV-2006 | SEQ ID NO: 125 | GGGCGTGGTGGGTGGGGTTCGTCGTTTTGTCGTTTTGTCGTT |
| HIV-93del-2006 | SEQ ID NO: 126 | GGGGTGGGAGGAGGGTTCGTCGTTTTGTCGTTTTGTCGTT |
| Hema-2006 | SEQ ID NO: 127 | GGGGTCGGGCGGGCCGGGTGTCGTCGTTTTGTCGTTTTGTCGTT |
| Insu-2006 | SEQ ID NO: 128 | GGTGGTGGGGGGGTTGGTAGGGTTCGTCGTTTTGTCGTTTTGTCGTT |
| IonK-2006 | SEQ ID NO: 129 | GGGTTAGGGTTAGGGTAGGGTCGTCGTTTTGTCGTTTTGTCGTT |
| Scle-2006 | SEQ ID NO: 130 | TGGGGGGGTGGGTGGGTTCGTCGTTTTGTCGTTTTGTCGT |
| STAT-2006 | SEQ ID NO: 131 | GGGCGGCGGGCGGGCTCGTCGTTTTGTCGTTTTGTCGTT |
| TBA-2006 | SEQ ID NO: 132 | GGTTGGTGTGGTTGGTCGTCGTTTTGTCGTTTTGTCGTT |
| TNF-2006 | SEQ ID NO: 133 | GGTGGATGGCGCAGTCGGTCGTCGTTTTGTCGTTTTGTCGTT |
| apVEGF-D-2006 | SEQ ID NO: 134 | TGGGGGTGGACGGGCCGGGTTCGTCGTTTTGTCGTTTTGTCGTT |
| apVEGF-2006 | SEQ ID NO: 135 | TGTGGGGGTGGACGGGCCGGGTTCGTCGTTTTGTCGTTTTGTCGTT |
| HTR-2006 | SEQ ID NO: 136 | GGGTTAGGGTTAGGGTTAGGGTCGTCGTTTTGTCGTTTTGTCGTT |
| bcl-2-2006 | SEQ ID NO: 137 | GGGCGCGGGAGGAAGGGGGCGGGTCGTCGTTTTGTCGTTTTGTCGTT |
| c-myc-2006 | SEQ ID NO: 138 | AGGGTGGGGAGGGTGGGGATCGTCGTTTTGTCGTTTTGTCGTT |

TABLE 1-continued

Oligonucleotide sequences

| | | |
|---|---|---|
| c-kit87-2006 | SEQ ID NO: 139 | AGGGAGGGCGCTGGGAGGAGGGTCGTCGTTTTGTCGTTTT GTCGTT |
| vegf-2006 | SEQ ID NO: 140 | GGGGCGGGCCGGGGCGGGGTCGTCGTTTTGTCGTTTTGT CGTT |
| 2006-PDE-Gwire1 | SEQ ID NO: 141 | GGGGTTGGGGTCGTCGTTTTGTCGTTTTGTCGTT |
| 2006-PDE-Gwire2 | SEQ ID NO: 142 | GGGGTTGGGGTTTTCGTCGTTTTGTCGTTTTGTCGTT |
| 2006PDE5dG4-T1-6 | SEQ ID NO: 143 | TGGGGTTCGTCGTTTTGTCGTTTTGTCGTT |
| 1-ACGA | SEQ ID NO: 144 | TTTTTTTACGATTT |
| 2-GCGA | SEQ ID NO: 145 | TTTTTTTGCGATTT |
| 3-CCGA | SEQ ID NO: 146 | TTTTTTTCCGATTT |
| 4-TCGA | SEQ ID NO: 147 | TTTTTTTTCGATTT |
| 5-ACGG | SEQ ID NO: 148 | TTTTTTTACGGTTT |
| 6-GCGG | SEQ ID NO: 149 | TTTTTTTGCGGTTT |
| 7-CCGG | SEQ ID NO: 150 | TTTTTTTCCGGTTT |
| 8-TCGG | SEQ ID NO: 151 | TTTTTTTTCGGTTT |
| 9-ACGC | SEQ ID NO: 152 | TTTTTTTACGCTTT |
| 10-GCGC | SEQ ID NO: 153 | TTTTTTTGCGCTTT |
| 11-CCGC | SEQ ID NO: 154 | TTTTTTTCCGCTTT |
| 12-TCGC | SEQ ID NO: 155 | TTTTTTTTCGCTTT |
| 13-ACGT | SEQ ID NO: 156 | TTTTTTTACGTTTT |
| 14-GCGT | SEQ ID NO: 157 | TTTTTTTGCGTTTT |
| 15-CCGT | SEQ ID NO: 158 | TTTTTTTCCGTTTT |
| 16-TCGT | SEQ ID NO: 159 | TTTTTTTTCGTTTT |
| 17-ACGA-5dG6 | SEQ ID NO: 160 | GGGGGGTTTTTTTACGATTT |
| 18-GCGA-5dG6 | SEQ ID NO: 161 | GGGGGGTTTTTTTGCGATTT |
| 19-CCGA-5dG6 | SEQ ID NO: 162 | GGGGGGTTTTTTTCCGATTT |
| 20-TCGA-5dG6 | SEQ ID NO: 163 | GGGGGGTTTTTTTTCGATTT |
| 21-ACGG-5dG6 | SEQ ID NO: 164 | GGGGGGTTTTTTTACGGTTT |
| 22-GCGG-5dG6 | SEQ ID NO: 165 | GGGGGGTTTTTTTGCGGTTT |
| 23-CCGG-5dG6 | SEQ ID NO: 166 | GGGGGGTTTTTTTCCGGTTT |
| 24-TCGG-5dG6 | SEQ ID NO: 167 | GGGGGGTTTTTTTTCGGTTT |
| 25-ACGC-5dG6 | SEQ ID NO: 168 | GGGGGGTTTTTTTACGCTTT |
| 26-GCGC-5dG6 | SEQ ID NO: 169 | GGGGGGTTTTTTTGCGCTTT |
| 27-CCGC-5dG6 | SEQ ID NO: 170 | GGGGGGTTTTTTTCCGCTTT |
| 28-TCGC-5dG6 | SEQ ID NO: 171 | GGGGGGTTTTTTTTCGCTTT |
| 29-ACGT-5dG6 | SEQ ID NO: 172 | GGGGGGTTTTTTTACGTTTT |
| 30-GCGT-5dG6 | SEQ ID NO: 173 | GGGGGGTTTTTTTGCGTTTT |
| 31-CCGT-5dG6 | SEQ ID NO: 174 | GGGGGGTTTTTTTCCGTTTT |
| 32-TCGT-5dG6 | SEQ ID NO: 175 | GGGGGGTTTTTTTTCGTTTT |

TABLE 1-continued

Oligonucleotide sequences

| | | |
|---|---|---|
| 33-ACGA-Gwire2 | SEQ ID NO: 176 | GGGGTTGGGGTTTTTTTTTTTACGATTT |
| 34-GCGA-Gwire2 | SEQ ID NO: 177 | GGGGTTGGGGTTTTTTTTTTTGCGATTT |
| 35-CCGA-Gwire2 | SEQ ID NO: 178 | GGGGTTGGGGTTTTTTTTTTTCCGATTT |
| 36-TCGA-Gwire2 | SEQ ID NO: 179 | GGGGTTGGGGTTTTTTTTTTTTCGATTT |
| 37-ACGG-Gwire2 | SEQ ID NO: 180 | GGGGTTGGGGTTTTTTTTTTTACGGTTT |
| 38-GCGG-Gwire2 | SEQ ID NO: 181 | GGGGTTGGGGTTTTTTTTTTTGCGGTTT |
| 39-CCGG-Gwire2 | SEQ ID NO: 182 | GGGGTTGGGGTTTTTTTTTTTCCGGTTT |
| 40-TCGG-Gwire2 | SEQ ID NO: 183 | GGGGTTGGGGTTTTTTTTTTTTCGGTTT |
| 41-ACGC-Gwire2 | SEQ ID NO: 184 | GGGGTTGGGGTTTTTTTTTTTACGCTTT |
| 42-GCGC-Gwire2 | SEQ ID NO: 185 | GGGGTTGGGGTTTTTTTTTTTGCGCTTT |
| 43-CCGC-Gwire2 | SEQ ID NO: 186 | GGGGTTGGGGTTTTTTTTTTTCCGCTTT |
| 44-TCGC-Gwire2 | SEQ ID NO: 187 | GGGGTTGGGGTTTTTTTTTTTTCGCTTT |
| 45-ACGT-Gwire2 | SEQ ID NO: 188 | GGGGTTGGGGTTTTTTTTTTTACGTTTT |
| 46-GCGT-Gwire2 | SEQ ID NO: 189 | GGGGTTGGGGTTTTTTTTTTTGCGTTTT |
| 47-CCGT-Gwire2 | SEQ ID NO: 190 | GGGGTTGGGGTTTTTTTTTTTCCGTTTT |
| 48-TCGT-Gwire2 | SEQ ID NO: 191 | GGGGTTGGGGTTTTTTTTTTTTCGTTTT |
| GCGT-Gwire2-GC | SEQ ID NO: 192 | GGGGTTGGGGTTTTTTTTTTTGGCTTTT |
| GCGT-Gwire2-TG | SEQ ID NO: 193 | GGGGTTGGGGTTTTTTTTTTTGTGTTTT |
| GCGT-Gwire2-CA | SEQ ID NO: 194 | GGGGTTGGGGTTTTTTTTTTTGCATTTT |
| GCGT-Gwire2-T1 | SEQ ID NO: 195 | GGGGTTGGGGTTTTTTTTTTGCGTTTT |
| GCGT-Gwire2-T2 | SEQ ID NO: 196 | GGGGTTGGGGTTTTTTTTTGCGTTTT |
| GCGT-Gwire2-T3 | SEQ ID NO: 197 | GGGGTTGGGGTTTTTTTTGCGTTTT |
| GCGT-Gwire2-T4 | SEQ ID NO: 198 | GGGGTTGGGGTTTTTTTGCGTTTT |
| GCGT-Gwire2-T5 | SEQ ID NO: 199 | GGGGTTGGGGTTTTTTGCGTTTT |
| GCGT-Gwire2-T6 | SEQ ID NO: 200 | GGGGTTGGGGTTTTTGCGTTTT |
| GCGT-Gwire2-eT1 | SEQ ID NO: 201 | GGGGTTGGGGTTTTTTTTTTTGCGTTT |
| GCGT-Gwire2-eT2 | SEQ ID NO: 202 | GGGGTTGGGGTTTTTTTTTTTGCGTT |
| GCGT-Gwire2-eT3 | SEQ ID NO: 203 | GGGGTTGGGGTTTTTTTTTTTGCGT |
| GCGT-Gwire3 | SEQ ID NO: 224 | GGGGTTGGGGTGGGGTTTTTTTTTTTGCGTTTT |
| GCGT-Gwire2-do | SEQ ID NO: 204 | GGGGTTGGGGTTTTTTTTTTTGCGTTTTGCGTTTT |
| GCGT-Gwire2-tri | SEQ ID NO: 205 | GGGGTTGGGGTTTTTTTTTTTGCGTTTTGCGTTTTGCGTTT |
| GCGA-Gwire2 | SEQ ID NO: 177 | GGGGTTGGGGTTTTTTTTTTTGCGATTT |
| GCGA-Gwire2-do | SEQ ID NO: 206 | GGGGTTGGGGTTTTTTTTTTTGCGATTTGCGATTT |
| GCGA-Gwire2-tri | SEQ ID NO: 207 | GGGGTTGGGGTTTTTTTTTTTGCGATTTGCGATTTGCGATTT |
| ACGC-Gwire2 | SEQ ID NO: 184 | GGGGTTGGGGTTTTTTTTTTTACGCTTT |

TABLE 1-continued

Oligonucleotide sequences

| Name | SEQ ID | Sequence |
|---|---|---|
| ACGC-Gwire2-do | SEQ ID NO: 208 | GGGGTTGGGGTTTTTTTTTTACGCTTTACGCTTT |
| ACGC-Gwire2-tri | SEQ ID NO: 209 | GGGGTTGGGGTTTTTTTTTTACGCTTTACGCTTTACGCTTT |
| TCGC-Gwire2 | SEQ ID NO: 187 | GGGGTTGGGGTTTTTTTTTTCGCTTT |
| TCGC-Gwire2-do | SEQ ID NO: 210 | GGGGTTGGGGTTTTTTTTTTCGCTTTTCGCTTT |
| TCGC-Gwire2-tri | SEQ ID NO: 211 | GGGGTTGGGGTTTTTTTTTTCGCTTTTCGCTTTTCGCTTT |
| CCGC-Gwire2 | SEQ ID NO: 186 | GGGGTTGGGGTTTTTTTTTTCCGCTTT |
| CCGC-Gwire2-do | SEQ ID NO: 212 | GGGGTTGGGGTTTTTTTTTTCCGCTTTCCGCTTT |
| CCGC-Gwire2-tri | SEQ ID NO: 213 | GGGGTTGGGGTTTTTTTTTTCCGCTTTCCGCTTTCCGCTTT |
| GCGG-Gwire2-mo | SEQ ID NO: 181 | GGGGTTGGGGTTTTTTTTTTGCGGTTT |
| GCGG-Gwire2-do | SEQ ID NO: 214 | GGGGTTGGGGTTTTTTTTTTGCGGTTTGCGGTTT |
| GCGG-Gwire2-tri | SEQ ID NO: 215 | GGGGTTGGGGTTTTTTTTTTGCGGTTTGCGGTTTGCGGTTT |
| CG-Gw2-T0 | SEQ ID NO: 216 | GGGGTTGGGGTTTTTTTCGCGCGTTT |
| CG-Gw2-T1 | SEQ ID NO: 217 | GGGGTTGGGGTTTTTTTCGTCGTCGTTT |
| CG-Gw2-T2 | SEQ ID NO: 218 | GGGGTTGGGGTTTTTTTCGTTCGTTCGTTT |
| CG-Gw2-T3 | SEQ ID NO: 219 | GGGGTTGGGGTTTTTTTCGTTTCGTTTCGTTT |
| CG-Gw2-T4 | SEQ ID NO: 220 | GGGGTTGGGGTTTTTTTCGTTTTCGTTTTCGTTT |
| CG-Gw2-abase | SEQ ID NO: 221 | GGGGTTGGGGTTTTTTTCGXCGXCGTTT<br>X = abasic site |
| CG-Gw2X1 | SEQ ID NO: 222** | GGGGTTGGGGTTTTTTTCGX1CGX1CGTTT<br>X1 = C18 |
| CG-Gw2X2 | SEQ ID NO: 223** | GGGGTTGGGGTTTTTTTCGX2CGX2CGTTT<br>X2 = C3 |
| CG-Gw2X2-1 | SEQ ID NO: 225** | GGGGTTGGGGTTTTTTTCGX2CGTTT<br>X2 = C3 |
| CG-Gw2X2-2 | SEQ ID NO: 223** | GGGGTTGGGGTTTTTTTCGX2CGX2CGTTT<br>X2 = C3 |
| CG-Gw2X2-3 | SEQ ID NO: 226** | GGGGTTGGGGTTTTTTTCGX2CGX2CGX2CGTTT<br>X2 = C3 |
| CG-Gw2X2-4 | SEQ ID NO: 227** | GGGGTTGGGGTTTTTTTCGX2CGX2CGX2CGX2CGTTT<br>X2 = C3 |
| CG-Gw2X2-5 | SEQ ID NO: 228** | GGGGTTGGGGTTTTTTTCGX2CGX2CGX2CGX2CGX2CGTTT<br>X2 = C3 |
| CG-G4T16X2-1 | SEQ ID NO: 229** | TGGGGTTTTTTTTCGX2CGTTT<br>X2 = C3 |
| CG-G4T16X2-2 | SEQ ID NO: 230** | TGGGGTTTTTTTTCGX2CGX2CGTTT<br>X2 = C3 |
| CG-G4T16X2-3 | SEQ ID NO: 231** | TGGGGTTTTTTTTCGX2CGX2CGX2CGTTT<br>X2 = C3 |
| CG-G4T16X2-4 | SEQ ID NO: 232** | TGGGGTTTTTTTTCGX2CGX2CGX2CGX2CGTTT<br>X2 = C3 |
| CG-G4T16X2-5 | SEQ ID NO: 233** | TGGGGTTTTTTTTCGX2CGX2CGX2CGX2CGX2CGTTT<br>X2 = C3 |

TABLE 1-continued

Oligonucleotide sequences

| Name | SEQ ID | Sequence |
|---|---|---|
| ODN-X2 | SEQ ID NO: 234** | GGGGTTGGGGTTTTTTTTCGX2CGX2CGTTT (X2 = Ethanediol) |
| ODN-X3 | SEQ ID NO: 223** | GGGGTTGGGGTTTTTTTTCGX3CGX3CGTTT (X3 = Propanediol) |
| ODN-X4 | SEQ ID NO: 235** | GGGGTTGGGGTTTTTTTTCGX4CGX4CGTTT (X4 = Butanediol) |
| ODN-X6 | SEQ ID NO: 236** | GGGGTTGGGGTTTTTTTTCGX6CGX6CGTTT (X6 = Hexanediol) |
| ODN-X9 | SEQ ID NO: 237** | GGGGTTGGGGTTTTTTTTCGX9CGX9CGTTT (X9 = Nonanediol) |
| ODN-X12 | SEQ ID NO: 238** | GGGGTTGGGGTTTTTTTTCGX12CGX12CGTTT (X12 = Dodecanediol) |
| ODN-Xab | SEQ ID NO: 239 | GGGGTTGGGGTTTTTTTTCGXabCGXabCGTTT (Xab = dSpacer (abasic)) |
| ODN-XtrEG | SEQ ID NO: 240** | GGGGTTGGGGTTTTTTTTCGXtrCGXtrCGTTT (Xtr = Triethyleneglycol) |
| ACGC-Gw2X1 | SEQ ID NO: 241** | GGGGTTGGGGTTTTTTTTACGCX1ACGCX1ACGCTTT X1 = C18 (HEG*) |
| CCGC-Gw2X1 | SEQ ID NO: 242** | GGGGTTGGGGTTTTTTTTCCGCX1CCGCX1CCGCTTT X1 = C18 (HEG*) |
| ACGC-Gw2X2 | SEQ ID NO: 243** | GGGGTTGGGGTTTTTTTTACGCX2ACGCX2ACGCTTT X2 = Propanediol |
| CCGC-Gw2X2 | SEQ ID NO: 244** | GGGGTTGGGGTTTTTTTTCCGCX2CCGCX2CCGCTTT X2 = Propanediol |
| ACGC-G4T16-X2 | SEQ ID NO: 245** | TGGGGTTTTTTTTACGCX2ACGCX2ACGCTTT X2 = Propanediol |
| CCGC-G4T16-X2 | SEQ ID NO: 246** | TGGGGTTTTTTTTCCGCX2CCGCX2CCGCTTT X2 = Propanediol |
| 2006-PDE5dG4-X1 | SEQ ID NO: 247** | GGGGX1TCGTCGTTTTGTCGTTTTGTCGTT X1 = C18 (HEG*) |
| 2006-PDE5dG4-X2 | SEQ ID NO: 248** | GGGGX2TCGTCGTTTTGTCGTTTTGTCGTT X2 = Propanediol |
| 2006-PDE5dG4-X3 | SEQ ID NO: 249** | GGGGX3GGGGTCGTCGTTTTGTCGTTTTGTCGTT X3 = C18 (HEG*) |
| 2006-PDE5dG4-X4 | SEQ ID NO: 250** | GGGGX4GGGGTCGTCGTTTTGTCGTTTTGTCGTT X4 = Propanediol |
| 2006-T4-5dTG4T | SEQ ID NO: 251 | TGGGGTTTTTCGTCGTTTTGTCGTTTTGTCGTT |
| 2006-T4TG4T-3C | SEQ ID NO: 251 | TGGGGTTTTTCGTCGTTTTGTCGTTTTGTCGTTX 3'-Cholesteryl |
| 5Chol-GCGT3-TG4T | SEQ ID NO: 1 | XTGGGGTTTTTTTGCGTTTTTGCGTTTTTGCGTTTT X = 5'-Cholesteryl |
| GCGT3-TG4T | SEQ ID NO: 252 | TGGGGTTTTTTTGCGTTTTTGCGTTTTTGCGTTTT |
| GCGT-3-Gw2-5Chol | SEQ ID NO: 253 | XGGGGTTGGGGTTTTTTTGCGTTTTTGCGTTTTTGCGTTTT 5'-Cholesteryl |
| GCGT-3-Gw2 | SEQ ID NO: 253 | GGGGTTGGGGTTTTTTTGCGTTTTTGCGTTTTTGCGTTTT |
| GCGT3-5Chol | SEQ ID NO: 254 | XTTTTTTTGCGTTTTTGCGTTTTTGCGTTTT X = 5'-Cholesteryl |

TABLE 1-continued

Oligonucleotide sequences

| | | |
|---|---|---|
| GCGT3 | SEQ ID NO: 254 | TTTTTTTGCGTTTTTGCGTTTTTGCGTTTT |
| 5Chol-CCGC3-Gw2 | SEQ ID NO: 255 | XGGGGTTGGGGTTTTTTTTCCGCTTTTCCGCTTTTCCGCTT<br>X = 5'-Cholesteryl |
| CCGC3-Gw2 | SEQ ID NO: 255 | GGGGTTGGGGTTTTTTTCCGCTTTTCCGCTTTTCCGCTTT |
| 5Chol-CCGC3 | SEQ ID NO: 256 | XTTTTTTTCCGCTTTTCCGCTTTTCCGCTTT<br>X = 5'-Cholesteryl |
| CCGC3 | SEQ ID NO: 256 | TTTTTTTCCGCTTTTCCGCTTTTCCGCTTT |

(lower case: PTO bonds, upper case PDE bonds)
*Hexaethyleneglycol
**As referred to herein, sequence names (e.g., "CG-Gw2X1," etc.) refer to the full sequences shown in this table, including the X1, X2, X3, X4, X6, X9, X12, and Xtr non-nucleotide linkers.

The immunogenic nucleic acid plasmids described herein are enriched in CpG motifs. In some aspects, the immunogenic nucleic acid plasmids contain more than 20% CpG motifs compared to the frequency of CpG motifs found in vertebrate nucleic acid sequences.

In some aspects, the present disclosure relates to immunogenic nucleic acid plasmids that do not comprise an antibiotic resistance gene. In some aspects, the plasmids do not comprise a nucleic acid sequence coding for a full-length or functional selectable or screenable marker. For example, the pGCMB75.6 plasmid described herein does not comprise any full-length or functional selectable or screenable marker genes. The sequence of pGCMB75.6 is provided in SEQ ID NO:265 (Table 1A). In some aspects, the plasmids described herein do not encode an immunogen.

In some aspects, the immunogenic plasmids may comprise a nucleic acid sequence coding for a selectable or screenable marker gene that is not an antibiotic resistance gene. For example, the pLacZMB75.6 plasmid described herein comprises a LacZ gene as a screenable marker. The sequence of pLacZMB75.6 is provided in SEQ ID NO:268. In still other aspects, the plasmid will contain an antibiotic resistance gene. For example, pMB75.6 comprises a nucleic acid sequence encoding a resistance to the antibiotic kanamycin. The sequence of pMB75.6 is provided in SEQ ID NO:266.

It will be appreciated that the nucleotide sequence of the pMB75.6, pGCMB75.6, or pLacZMB75.6 plasmid may be varied to a certain extent without significantly adversely affecting its immunostimulatory properties. In some aspects are provided an immunogenic nucleic acid plasmids comprising or consisting of a nucleic acid sequence having at least 89% sequence identity with the sequence of pGCMB75.6 (SEQ ID NO: 265). In some aspects, the immunogenic plasmid comprises a nucleic acid sequence having at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the sequence of pGCMB75.6 (SEQ ID NO:265). In some aspects, the immunogenic nucleic acid plasmid comprises the sequence of pGCMB75.6 (SEQ ID NO:265).

In some aspects are provided immunogenic nucleic acid plasmids comprising a nucleic acid sequence having at least 84% sequence identity with the sequence of pLacZMB75.6 (SEQ ID NO:268). In some aspects, the immunogenic plasmid comprises or consists of a nucleic acid sequence having at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the sequence of pLacZMB75.6 (SEQ ID NO:268). In some aspects, the immunogenic nucleic acid comprises a plasmid having the sequence of pLacZMB75.6 (SEQ ID NO:268).

In some aspects are provided immunogenic nucleic acid plasmids comprising a nucleic acid sequence having at least 80% sequence identity with the sequence of SEQ ID NO:266. In some aspects, the immunogenic plasmid comprises or consists of a nucleic acid sequence having at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the sequence of SEQ ID NO:266. In some aspects, the immunogenic nucleic acid plasmid comprises the sequence of SEQ ID NO:266.

In some aspects are provided an immunogenic nucleic acid plasmid comprising a nucleic acid sequence having at least 80% sequence identity with the sequence of pMB75.6_AscI (SEQ ID NO:267). In some aspects, the immunogenic plasmid comprises or consists of a nucleic acid sequence having at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the sequence of SEQ ID NO:267. In some aspects, the immunogenic nucleic acid plasmid comprises the sequence of SEQ ID NO:267.

TABLE 1A

| Plasmid sequences |
|---|
| pGCMB75.6<br>(SEQ ID NO: 265) |

```
tgaccgccca acgaccccg cccattgacg tcaataatga cgtatgttcc catagtaacg   60
ccaataggga ctttccattg acgtcaatgg gtggagtatt tacggtaaac tgcccacttg  120
gcagtacatc aagtgtatca tatgccaagt ccgcccccta ttgacgtcaa tgacggtaaa  180
tggcccgcct ggcattatgc ccagtacatg accttacggg actttcctac ttggcagtac  240
atctacgtat tagtcatcgc tattaccatg gtgatgcggt tttggcagta catcaatggg  300
cgtggatagc ggtttgactc acggggattt ccaagtctcc accccattga cgtcaatggg  360
agtttgtttt ggcaccaaaa tcaacgggac tttccaaaat gtcgtaacaa ctccgcccca  420
ttgacgcaaa tgggcggtag gcgtgtacgg tgggaggtct atataagcag agctcgttta  480
gtgaaccgtc agatcgcctg gagacgccat ccacgctgtt ttgacctcca tagaagacac  540
cgggaccgat ccagcctccc ctcgaagccg atctgataac ggtaccgata agctggcggc  600
cgattaagct acagaagttg gtcgtgaggc actgggcagg taagtatcaa ggttacaaga  660
caggtttaag gagaccaata gaaactgggc ttgtcgagac agagaagact cttgcgtttc  720
tgataggcac ctattggtct tactgacatc cactttgcct ttctctccac aggtgtccac  780
tcccaggttc aattacagct cttaagcagc gcaagcttg atatcgaatt cctgcagccc  840
gggggatcca ctagttctag agcggccgcc accgcggtgg agctcgaatt atcagatcga  900
ttaataacta tgctcaaaaa ttgtgtacct ttagcttttt aatttgtaaa ggggttaata  960
aggaatattt gatgtatagt gccttgacta gagatcataa tcagccatac cacatttgta 1020
gaggttttac ttgctttaaa aaacctccca cacctccccc tgaacctgaa acataaaatg 1080
aatgcaattg ttgttgttaa cttgtttatt gcagcttata atggttacaa ataaagcaat 1140
agcatcacaa atttcacaaa taaagcattt ttttcactgc attctagttg tggtttgtcc 1200
aaactcatca atgtatctta tcatgtctgg atcatcagat ctgccggtct ccctatagtg 1260
agtcgtatta atttcgataa gccaggttaa cctgcattaa tgaatcggcc aacgcgcggg 1320
gagaggcggt ttgcgtattg ggcgctcttc cgcttcctcg ctcactgact cgctgcgctc 1380
ggtcgttcgg ctgcggcgag cggtatcagc tcactcaaag gcggtaatac ggttatccac 1440
agaatcaggg gataacgcag gaaagaacat gtgagcaaaa ggccagcaaa aggccaggaa 1500
ccgtaaaaag gccgcgttgc tggcgttttt ccataggctc cgcccccctg acgagcatca 1560
caaaaatcga cgctcaagtc agaggtggcg aaacccgaca ggactataaa gataccaggc 1620
gtttccccct ggaagctccc tcgtgcgctc tcctgttccg accctgccgc ttaccggata 1680
cctgtccgcc tttctccctt cgggaagcgt ggcgctttct catagctcac gctgtaggta 1740
tctcagttcg gtgtaggtcg ttcgctccaa gctgggctgt gtgcacgaac cccccgttca 1800
gcccgaccgc tgcgccttat ccggtaacta tcgtcttgag tccaacccgg taagacacga 1860
cttatcgcca ctggcagcag ccactggtaa caggattagc agagcgaggt atgtaggcgg 1920
tgctacagag ttcttgaagt ggtggcctaa ctacggctac actagaagaa cagtatttgg 1980
tatctgcgct ctgctgaagc cagttacctt cggaaaaaga gttggtagct cttgatccgg 2040
caaacaaacc accgctggta gcggtggttt ttttgtttgc aagcagcaga ttacgcgcag 2100
aaaaaaagga tctcaagaag atcctttgat cttttctacg ggtctgacg ctcagtggaa 2160
cgaaaactca cgttaaggga ttttggtcat gggcgcgcct aggcttttgc aaagatcgat 2220
caagagacag gatgaggatc gtttcgcagc ttttcattct gactgcaacg ggcaataagt 2280
```

TABLE 1A-continued

Plasmid sequences

```
ctctgtgtgg attaaaaaaa gagtgtctga tagcagcttc tgaactggtt acctgccgtg 2340
agtaaattaa aattttattg acttaggtca ctaaggcgcc ttgcgctgag gttgcgtcgt 2400
gatatcatca gggcagaccg gttacatccc cctaacaagc tgtataaaga gaaatactat 2460
ctcattggcg ttgcccgcac ctgacagtgc gacgttgggc tgcgtccgtc gaccaacggt 2520
accgaggtaa cagcccaatc tatccatgat ctcggccagg ccgggtcggc cgttatgcag 2580
cccggctcgg gtatgaagcc attaaggagc cgacccagcg cgaccgggcg gccggtcacg 2640
ctgcctctgc tgaagcctgc ctgtcactcc ctgcgcggcg tacccgccgt tctcatcgag 2700
taggctccgg atcgcgaccc cggacgggcc ctgggcccag gagcggccta tgacaaatgc 2760
cgggtagcga tccggcattc agcattgact gcgcacggat ccagtccttg caggagcctt 2820
atgccgaccg tagcaaaaaa tgagcccgag ccgatcgcga ttgtgatcc ggtcccgccg 2880
attgccggtc gcgatgacgg tcctgtgtaa gcgttatcgt taccaattgt ttaagaagta 2940
tatacgctac gaggtacttg ataacttctg cgtagcatac atgaggtttt gtataaaaat 3000
ggcgggcgat atcaacgcag tgtcagaaat ccgaaacagt ctgcgggact ctggggttcg 3060
aaatgaccga ccaagcgacg cccaacctgc catcacgaga tttcgattcc accgccgcct 3120
tctatgaaag gttgggcttc ggaatcgttt tccgggacgc cggctggatg atcctccagc 3180
gcggggatct catgctggag ttcttcgccc accctaggcg cgctcatgag cggatacata 3240
tttgaatgta tttagaaaaa taaacaaata ggggttccgc gcacatttcc ccgaaaagtg 3300
ccacctaaat tgtaagcgtt aatattttgt taaaattcgc gttaaatttt tgttaaatca 3360
gctcattttt taaccaatag gccgaaatcg gcaaaatccc ttataaatca aagaataga 3420
ccgagatagg gttgagtgtt gttccagttt ggaacaagag tccactatta agaacgtgg 3480
actccaacgt caaagggcga aaaaccgtct atcaggcga tggcccacta cgtgaaccat 3540
cacccctaatc aagttttttg gggtcgaggt gccgtaaagc actaaatcgg aaccctaaag 3600
ggagccccg atttagagct tgacggggaa agccggcgaa cgtggcgaga aggaaggga 3660
agaaagcgaa aggagcgggc gctagggcgc tggcaagtgt agcggtcacg ctgcgcgtaa 3720
ccaccacacc cgccgcgctt aatgcgccgc tacagggcgc gtcccattcg ccattcaggc 3780
tgcgcaactg ttgggaaggg cgatcggtgc gggcctcttc gctattacgc cagctggcga 3840
aaggggatg tgctgcaagg cgattaagtt gggtaacgcc aggttttcc cagtcacgac 3900
gttgtaaaac gacggccagt gagcgcgcgt aatacgactc actatagggc gaattgggta 3960
ccgggccccc cctcgagcag gatctataca ttgaatcaat attggcaatt agccatatta 4020
gtcattggtt atatagcata atcaatatt ggctattggc cattgcatac gttgtatcta 4080
tatcataata tgtacattta tattggctca tgtccaatat gaccgccatg ttgacattga 4140
ttattgacta gttattaata gtaatcaatt acggggtcat tagttcatag cccatatatg 4200
gagttccgcg ttacataact tacggtaaat ggcccgcctg gc           4242
``` pMB75.6
(SEQ ID NO: 266)

```
ctaaattgta agcgttaata ttttgttaaa attcgcgtta aattttttgtt aaatcagctc   60
attttttaac caataggccg aaatcggcaa aatcccttat aaatcaaaag aatagaccga  120
gatagggttg agtgttgttc cagtttggaa caagagtcca ctattaaaga acgtggactc  180
caacgtcaaa gggcgaaaaa ccgtctatca gggcgatggc ccactacgtg aaccatcacc  240
```

TABLE 1A-continued

Plasmid sequences

```
ctaatcaagt tttttggggt cgaggtgccg taaagcacta aatcggaacc ctaaagggag  300
cccccgattt agagcttgac ggggaaagcc ggcgaacgtg gcgagaaagg aagggaagaa  360
agcgaaagga gcgggcgcta gggcgctggc aagtgtagcg gtcacgctgc gcgtaaccac  420
cacacccgcc gcgcttaatg cgccgctaca gggcgcgtcc cattcgccat tcaggctgcg  480
caactgttgg gaagggcgat cggtgcgggc ctcttcgcta ttacgccagc tggcgaaagg  540
gggatgtgct gcaaggcgat taagttgggt aacgccaggg ttttcccagt cacgacgttg  600
taaaacgacg gccagtgagc gcgcgtaata cgactcacta tagggcgaat tgggtaccgg  660
gccccccctc gagcaggatc tatacattga atcaatattg gcaattagcc atattagtca  720
ttggttatat agcataaatc aatattggct attggccatt gcatacgttg tatctatatc  780
ataatatgta catttatatt ggctcatgtc caatatgacc gccatgttga cattgattat  840
tgactagtta ttaatagtaa tcaattacgg ggtcattagt tcatagccca tatatggagt  900
tccgcgttac ataacttacg gtaaatggcc cgcctggctg accgcccaac gacccccgcc  960
cattgacgtc aataatgacg tatgttccca tagtaacgcc aatagggact ttccattgac 1020
gtcaatgggt ggagtattta cggtaaactg cccacttggc agtacatcaa gtgtatcata 1080
tgccaagtcc gccccctatt gacgtcaatg acggtaaatg gcccgcctgg cattatgccc 1140
agtacatgac cttacgggac tttcctactt ggcagtacat ctacgtatta gtcatcgcta 1200
ttaccatggt gatgcggttt tggcagtaca tcaatgggcg tggatagcgg tttgactcac 1260
ggggatttcc aagtctccac cccattgacg tcaatgggag tttgttttgg caccaaaatc 1320
aacgggactt tccaaaatgt cgtaacaact ccgccccatt gacgcaaatg ggcggtaggc 1380
gtgtacggtg ggaggtctat ataagcagag ctcgtttagt gaaccgtcag atcgcctgga 1440
gacgccatcc acgctgtttt gacctccata agacaccg ggaccgatcc agcctcccct 1500
cgaagccgat ctgataacgg taccgataag ctggcggccg attaagctac agaagttggt 1560
cgtgaggcac tgggcaggta agtatcaagg ttacaagaca ggtttaagga gaccaataga 1620
aactgggctt gtcgagacag agaagactct tgcgtttctg ataggcacct attggtctta 1680
ctgacatcca ctttgccttt ctctccacag gtgtccactc ccaggttcaa ttacagctct 1740
taagcagccg caagcttgat atcgaattcc tgcagcccgg gggatccact agttctagag 1800
cggccgccac cgcggtggag ctcgaattat cagatcgatt aataactatg ctcaaaaatt 1860
gtgtaccttt agcttttaa tttgtaaagg ggttaataag gaatatttga tgtatagtgc 1920
cttgactaga gatcataatc agccatacca catttgtaga ggttttactt gctttaaaaa 1980
acctcccaca cctcccctg aacctgaaac ataaaatgaa tgcaattgtt gttgttaact 2040
tgtttattgc agcttataat ggttacaaat aaagcaatag catcacaaat ttcacaaata 2100
aagcattttt ttcactgcat tctagttgtg gtttgtccaa actcatcaat gtatcttatc 2160
atgtctggat catcagatct gccggtctcc ctatagtgag tcgtattaat ttcgataagc 2220
caggttaacc tgcattaatg aatcggccaa cgcgcgggga gaggcggttt gcgtattggg 2280
cgctcttccg cttcctcgct cactgactcg ctgcgctcgg tcgttcggct gcggcgagcg 2340
gtatcagctc actcaaaggc ggtaatacgg ttatccacag aatcagggga taacgcagga 2400
aagaacatgt gagcaaaagg ccagcaaaag gccaggaacc gtaaaaaggc cgcgttgctg 2460
gcgtttttcc ataggctccg ccccctgac gagcatcaca aaaatcgacg ctcaagtcag 2520
aggtggcgaa acccgacagg actataaaga taccaggcgt ttccccctgg aagctccctc 2580
```

TABLE 1A-continued

Plasmid sequences

```
gtgcgctctc ctgttccgac cctgccgctt accggatacc tgtccgcctt tctcccttcg 2640
ggaagcgtgg cgctttctca tagctcacgc tgtaggtatc tcagttcggt gtaggtcgtt 2700
cgctccaagc tgggctgtgt gcacgaaccc cccgttcagc ccgaccgctg cgccttatcc 2760
ggtaactatc gtcttgagtc caacccggta agacacgact tatcgccact ggcagcagcc 2820
actggtaaca ggattagcag agcgaggtat gtaggcggtg ctacagagtt cttgaagtgg 2880
tggcctaact acggctacac tagaagaaca gtatttggta tctgcgctct gctgaagcca 2940
gttaccttcg gaaaaagagt tggtagctct tgatccggca acaaaccac cgctggtagc 3000 ggtggttttt ttgtttgcaa gcagcagatt acgcgcagaa aaaaggatc tcaagaagat 3060 cctttgatct tttctacggg gtctgacgct cagtggaacg aaaactcacg ttaagggatt 3120
ttggtcatga gcgcgcctag gcttttgcaa agatcgatca agagacagga tgaggatcgt 3180
ttcgcatgat tgaacaagat ggattgcacg caggttctcc ggccgcttgg gtggagaggc 3240
tattcggcta tgactgggca caacagacaa tcggctgctc tgatgccgcc gtgttccggc 3300
tgtcagcgca ggggcgcccg gttcttttg tcaagaccga cctgtccggt gccctgaatg 3360
aactgcaaga cgaggcagcg cggctatcgt ggctggccac gacgggcgtt ccttgcgcag 3420
ctgtgctcga cgttgtcact gaagcgggaa gggactggct gctattggc gaagtgccgg 3480 ggcaggatct cctgtcatct caccttgctc ctgccgagaa agtatccatc atggctgatg 3540
caatgcggcg gctgcatacg cttgatccgg ctacctgccc attcgaccac caagcgaaac 3600
atcgcatcga gcgagcacgt actcggatgg aagccggtct tgtcgatcag gatgatctgg 3660
acgaagagca tcaggggctc gcgccagccg aactgttcgc caggctcaag gcgagcatgc 3720
ccgacggcga ggatctcgtc gtgacccatg gcgatgcctg cttgccgaat atcatggtgg 3780
aaaatggccg cttttctgga ttcatcgact gtggccggct gggtgtggcg gaccgctatc 3840
aggacatagc gttggctacc cgtgatattg ctgaagagct tggcggcgaa tgggctgacc 3900
gcttcctcgt gctttacggt atcgccgctc ccgattcgca gcgcatcgcc ttctatcgcc 3960
ttcttgacga gttcttctga gcgggactct ggggttcgaa atgaccgacc aagcgacgcc 4020
caacctgcca tcacgagatt tcgattccac cgccgccttc tatgaaaggt tgggcttcgg 4080
aatcgttttc cgggacgccg gctggatgat cctccagcgc ggggatctca tgctggagtt 4140
cttcgcccac cctaggcgcg ctcatgagcg gatacatatt tgaatgtatt tagaaaaata 4200
aacaaatagg ggttccgcgc acatttcccc gaaaagtgcc ac                     4242
``` pMB75.6_AscI
(SEQ ID NO: 267)

```
tgaccgccca acgaccccg cccattgacg tcaataatga cgtatgttcc catagtaacg   60
ccaataggga ctttccattg acgtcaatgg gtggagtatt tacggtaaac tgcccacttg  120
gcagtacatc aagtgtatca tatgccaagt ccgccccta ttgacgtcaa tgacggtaaa  180
tggcccgcct ggcattatgc ccagtacatg accttacggg actttcctac ttggcagtac  240
atctacgtat tagtcatcgc tattaccatg gtgatgcggt tttggcagta catcaatggg  300
cgtggatagc ggtttgactc acggggattt ccaagtctcc accccattga cgtcaatggg  360
agtttgtttt ggcaccaaaa tcaacgggac tttccaaaat gtcgtaacaa ctccgcccca  420
ttgacgcaaa tgggcggtag gcgtgtacgg tgggaggtct atataagcag agctcgttta  480
gtgaaccgtc agatcgcctg gagacgccat ccacgctgtt tgacctcca tagaagacac  540 cgggaccgat ccagcctccc ctcgaagccg atctgataac ggtaccgata agctggcggc  600
```

TABLE 1A-continued

Plasmid sequences

```
cgattaagct acagaagttg gtcgtgaggc actgggcagg taagtatcaa ggttacaaga  660
caggtttaag gagaccaata gaaactgggc ttgtcgagac agagaagact cttgcgtttc  720
tgataggcac ctattggtct tactgacatc cactttgcct ttctctccac aggtgtccac  780
tcccaggttc aattacagct cttaagcagc cgcaagcttg atatcgaatt cctgcagccc  840
ggggatcca ctagttctag agcggccgcc accgcggtgg agctcgaatt atcagatcga  900
ttaataacta tgctcaaaaa ttgtgtacct ttagcttttt aatttgtaaa ggggttaata  960
aggaatattt gatgtatagt gccttgacta gagatcataa tcagccatac cacatttgta 1020
gaggttttac ttgctttaaa aaacctccca cacctccccc tgaacctgaa acataaaatg 1080
aatgcaattg ttgttgttaa cttgtttatt gcagcttata atggttacaa ataaagcaat 1140
agcatcacaa atttcacaaa taaagcattt ttttcactgc attctagttg tggtttgtcc 1200
aaactcatca atgtatctta tcatgtctgg atcatcagat ctgccggtct ccctatagtg 1260
agtcgtatta atttcgataa gccaggttaa cctgcattaa tgaatcggcc aacgcgcggg 1320
gagaggcggt ttgcgtattg ggcgctcttc cgcttcctcg ctcactgact cgctgcgctc 1380
ggtcgttcgg ctgcggcgag cggtatcagc tcactcaaag gcggtaatac ggttatccac 1440
agaatcaggg gataacgcag gaaagaacat gtgagcaaaa ggccagcaaa aggccaggaa 1500
ccgtaaaaag gccgcgttgc tggcgttttt ccataggctc cgcccccctg acgagcatca 1560
caaaaatcga cgctcaagtc agaggtggcg aaacccgaca ggactataaa gataccaggc 1620
gtttccccct ggaagctccc tcgtgcgctc tcctgttccg accctgccgc ttaccggata 1680
cctgtccgcc tttctccctt cgggaagcgt ggcgctttct catagctcac gctgtaggta 1740
tctcagttcg gtgtaggtcg ttcgctccaa gctgggctgt gtgcacgaac cccccgttca 1800
gcccgaccgc tgcgccttat ccggtaacta tcgtcttgag tccaacccgg taagacacga 1860
cttatcgcca ctggcagcag ccactggtaa caggattagc agagcgaggt atgtaggcgg 1920
tgctacagag ttcttgaagt ggtggcctaa ctacggctac actagaagaa cagtatttgg 1980
tatctgcgct ctgctgaagc cagttacctt cggaaaaaga gttggtagct cttgatccgg 2040
caaacaaacc accgctggta gcggtggttt ttttgtttgc aagcagcaga ttacgcgcag 2100
aaaaaaagga tctcaagaag atcctttgat cttttctacg gggtctgacg ctcagtggaa 2160
cgaaaactca cgttaaggga ttttggtcat gggcgcgcct aggcttttgc aaagatcgat 2220
caagagacag gatgaggatc gtttcgcatg attgaacaag atggattgca cgcaggttct 2280
ccggccgctt gggtggagag gctattcggc tatgactggg cacaacagac aatcggctgc 2340
tctgatgccg ccgtgttccg gctgtcagcg caggggcgcc cggttctttt tgtcaagacc 2400
gacctgtccg gtgccctgaa tgaactgcaa gacgaggcag cgcggctatc gtggctggcc 2460
acgacgggcg ttccttgcgc agctgtgctc gacgttgtca ctgaagcggg aagggactgg 2520
ctgctattgg gcgaagtgcc ggggcaggat ctcctgtcat ctcaccttgc tcctgccgag 2580
aaagtatcca tcatggctga tgcaatgcgg cggctgcata cgcttgatcc ggctacctgc 2640
ccattcgacc accaagcgaa acatcgcatc gagcgagcac gtactcggat ggaagccggt 2700
cttgtcgatc aggatgatct ggacgaagag catcaggggc tcgcgccagc cgaactgttc 2760
gccaggctca aggcgagcat gcccgacggc gaggatctcg tcgtgaccca tggcgatgcc 2820
tgcttgccga atatcatggt ggaaaatggc cgcttttctg gattcatcga ctgtggccgg 2880
ctgggtgtgg cggaccgcta tcaggacata gcgttggcta cccgtgatat tgctgaagag 2940
```

TABLE 1A-continued

Plasmid sequences

```
cttggcggcg aatgggctga ccgcttcctc gtgctttacg gtatcgccgc tcccgattcg 3000
cagcgcatcg ccttctatcg ccttcttgac gagttcttct gagcgggact ctggggttcg 3060
aaatgaccga ccaagcgacg cccaacctgc catcacgaga tttcgattcc accgccgcct 3120
tctatgaaag gttgggcttc ggaatcgttt tccgggacgc cggctggatg atcctccagc 3180
gcggggatct catgctggag ttcttcgccc accctaggcg cgctcatgag cggatacata 3240
tttgaatgta tttagaaaaa taaacaaata ggggttccgc gcacatttcc ccgaaaagtg 3300
ccacctaaat tgtaagcgtt aatattttgt taaaattcgc gttaaatttt tgttaaatca 3360
gctcattttt taaccaatag gccgaaatcg gcaaaatccc ttataaatca aagaataga 3420 ccgagatagg gttgagtgtt gttccagttt ggaacaagag tccactatta agaacgtgg 3480 actccaacgt caaagggcga aaaaccgtct atcagggcga tggcccacta cgtgaaccat 3540
caccctaatc aagttttttg gggtcgaggt gccgtaaagc actaaatcgg aaccctaaag 3600
ggagcccccg atttagagct tgacggggaa agccggcgaa cgtggcgaga aggaaggga 3660 agaaagcgaa aggagcgggc gctagggcgc tggcaagtgt agcggtcacg ctgcgcgtaa 3720
ccaccacacc cgccgcgctt aatgcgccgc tacagggcgc gtcccattcg ccattcaggc 3780
tgcgcaactg ttgggaaggg cgatcggtgc gggcctcttc gctattacgc cagctggcga 3840 aaggggatg tgctgcaagg cgattaagtt gggtaacgcc agggttttcc cagtcacgac 3900
gttgtaaaac gacggccagt gagcgcgcgt aatacgactc actatagggc gaattgggta 3960
ccgggccccc cctcgagcag gatctataca ttgaatcaat attggcaatt agccatatta 4020
gtcattggtt atatagcata atcaatatt ggctattggc cattgcatac gttgtatcta 4080
tatcataata tgtacattta tattggctca tgtccaatat gaccgccatg ttgacattga 4140
ttattgacta gttattaata gtaatcaatt acggggtcat tagttcatag cccatatatg 4200
gagttccgcg ttacataact tacggtaaat ggcccgcctg gc           4242
``` pLacZMB75.6
(SEQ ID NO: 268)

```
tgaccgccca acgaccccg cccattgacg tcaataatga cgtatgttcc catagtaacg   60
ccaataggga ctttccattg acgtcaatgg gtggagtatt tacggtaaac tgcccacttg  120
gcagtacatc aagtgtatca tatgccaagt ccgcccccta ttgacgtcaa tgacggtaaa  180
tggcccgcct ggcattatgc ccagtacatg accttacggg actttcctac ttggcagtac  240
atctacgtat tagtcatcgc tattaccatg gtgatgcggt tttggcagta catcaatggg  300
cgtggatagc ggtttgactc acggggattt ccaagtctcc accccattga cgtcaatggg  360
agtttgtttt ggcaccaaaa tcaacgggac tttccaaaat gtcgtaacaa ctccgcccca  420
ttgacgcaaa tgggcggtag gcgtgtacgg tgggaggtct atataagcag agctcgttta  480
gtgaaccgtc agatcgcctg gagacgccat ccacgctgtt tgacctccaa tagaagacac  540
cgggaccgat ccagcctccc ctcgaagccg atctgataac ggtaccgata agctggcggc  600
cgattaagct acagaagttg gtcgtgaggc actgggcagg taagtatcaa ggttacaaga  660
caggtttaag gagaccaata gaaactgggc ttgtcgagac agagaagact cttgcgtttc  720
tgataggcac ctattggtct tactgacatc cactttgcct ttctctccac aggtgtccac  780
tcccaggttc aattacagct cttaagcagc gccaaaaca aaattcctca aaatcatca   840 tcgaatgaat ggtgaaataa tttccctgaa taactgtagt gttttcaggg cgcggcataa  900
```

TABLE 1A-continued

Plasmid sequences

```
taattaacta tgctcaaaaa ttgtgtacct ttagctttt aatttgtaaa ggggttaata  960
aggaatattt gatgtatagt gccttgacta gagatcataa tcagccatac cacatttgta 1020
gaggttttac ttgctttaaa aaacctccca cacctccccc tgaacctgaa acataaaatg 1080
aatgcaattg ttgttgttaa cttgtttatt gcagcttata atggttacaa ataaagcaat 1140
agcatcacaa atttcacaaa taaagcattt ttttcactgc attctagttg tggtttgtcc 1200
aaactcatca atgtatctta tcatgtctgg atcatcagat ctgccggtct ccctatagtg 1260
agtcgtatta atttcgataa gccaggttaa cctgcattaa tgaatcggcc aacgcgcggg 1320
gagaggcggt ttgcgtattg ggcgctcttc cgcttcctcg ctcactgact cgctgcgctc 1380
ggtcgttcgg ctgcggcgag cggtatcagc tcactcaaag gcggtaatac ggttatccac 1440
agaatcaggg gataacgcag gaaagaacat gtgagcaaaa ggccagcaaa aggccaggaa 1500
ccgtaaaaag gccgcgttgc tggcgttttt ccataggctc cgcccccctg acgagcatca 1560
caaaaatcga cgctcaagtc agaggtggcg aaacccgaca ggactataaa gataccaggc 1620
gtttccccct ggaagctccc tcgtgcgctc tcctgttccg accctgccgc ttaccggata 1680
cctgtccgcc tttctccctt cgggaagcgt ggcgctttct catagctcac gctgtaggta 1740
tctcagttcg tgtaggtcg ttcgctccaa gctgggctgt gtgcacgaac ccccgttca 1800
gcccgaccgc tgcgccttat ccggtaacta tcgtcttgag tccaacccgg taagacacga 1860
cttatcgcca ctggcagcag ccactggtaa caggattagc agagcgaggt atgtaggcgg 1920
tgctacagag ttcttgaagt ggtggcctaa ctacggctac actagaagaa cagtatttgg 1980
tatctgcgct ctgctgaagc cagttacctt cggaaaaaga gttggtagct cttgatccgg 2040
caaacaaacc accgctggta gcggtggttt ttttgtttgc aagcagcaga ttacgcgcag 2100
aaaaaaagga tctcaagaag atcctttgat cttttctacg gggtctgacg ctcagtggaa 2160
cgaaaactca cgttaaggga ttttggtcat gggcgcgcct aggcttttgc aaagatcgat 2220
caagagacag gatgaggatc gtttcgcagc ttttcattct gactgcaacg ggcaataagt 2280
ctctgtgtgg attaaaaaaa gagtgtctga tagcagcttc tgaactggtt acctgccgtg 2340
agtaaattaa aatttattg acttaggtca ctaaggcgcc ttgcgctgag gttgcgtcgt 2400
gatatcatca gggcagaccg gttacatccc cctaacaagc tgtataaaga gaatactat 2460
ctcattggcg ttgcccgcac ctgacagtgc gacgttgggc tgcgtccgtc gaccaacggt 2520
accgaggtaa cagcccaatc tatccatgat ctcggccagg ccgggtcggc cgttatgcag 2580
cccggctcgg gtatgaagcc attaaggagc cgacccagcg cgaccgggcg gccggtcacg 2640
ctgcctctgc tgaagcctgc ctgtcactcc ctgcgcggcg tacccgccgt tctcatcgag 2700
taggctccgg atcgcgaccc cggacgggcc ctgggcccag gagcggccta tgacaaatgc 2760
cgggtagcga tccggcattc agcattgact gcgcacggat ccagtccttg caggagcctt 2820
atgccgaccg tagcaaaaaa tgagcccgag ccgatcgcga gttgtgatcc ggtcccgccg 2880
attgccggtc gcgatgacgg tcctgtgtaa gcgttatcgt taccaattgt ttaagaagta 2940
tatacgctac gaggtacttg ataacttctg cgtagcatac atgaggtttt gtataaaaat 3000
ggcgggcgat atcaacgcag tgtcagaaat ccgaaacagt ctgcgggact ctggggttcg 3060
aaatgaccga ccaagcgacg cccaacctgc catcacgaga tttcgattcc accgccgcct 3120
tctatgaaag gttgggcttc ggaatcgttt tccgggacgc cggctggatg atcctccagc 3180
gcggggatct catgctggag ttcttcgccc accctaggcg cgctcatgag cggatacata 3240
```

TABLE 1A-continued

Plasmid sequences

```
tttgaatgta tttagaaaaa taaacaaata ggggttccgc gcacatttcc ccgaaaagtg 3300
ccacctaaat tgtaagcgtt aatattttgt taaaattcgc gttaaatttt tgttaaatca 3360
gctcattttt taaccaatag gccgaaatcg gcaaaatccc ttataaatca aaagaataga 3420
ccgagatagg gttgagtgtt gttccagttt ggaacaagag tccactatta aagaacgtgg 3480
actccaacgt caaagggcga aaaaccgtct atcagggcga tggcccacta cgtgaaccat 3540
caccctaatc aagtttttg gggtcgaggt gccgtaaagc actaaatcgg aaccctaaag 3600 ggagccccg atttagagct tgacgggaa agccggcgaa cgtggcgaga aaggaaggga 3660
agaaagcgaa aggagcgggc gctagggcgc tggcaagtgt agcggtcacg ctgcgcgtaa 3720
ccaccacacc cgccgcgctt aatgcgccgc tacagggcgc gtcccattcg ccattcaggc 3780
tgcgcaactg ttgggaaggg cgatcggtgc gggcctcttc gctattacgc cagctggcga 3840 aaggggatg tgctgcaagg cgattaagtt gggtaacgcc agggttttcc cagtcacgac 3900
gttgtaaaac gacggccagt gagcgcgcgt aatacgactc actatagggc gaattgggta 3960 ccgggcccc cctcgaggtc gacggtatcg ataagcttga tatcgaattc ctgcagcccg 4020
ggggatccac tagttctaga gcggccgcca ccgcggtgga gctccagctt ttgttcccctt 4080 tagtgagggt taattgcgcg cttggcgtaa tcatggtcat agctgtttcc tgtgtgaaat 4140
tgttatccgc tcacaattcc acacaacata cgagccggaa gcataaagtg taaagcctgg 4200
ggtgcctaat gagtgagcta actcacatta attgcgttgc gc          4242
```

Further provided herein are immunogenic nucleic acids or immunogenic plasmids capable of stimulating an immune response including nucleic acid sequences that hybridize under high stringency conditions to SEQ ID NO:265, SEQ ID NO:266, SEQ ID NO:267, or SEQ ID NO:268. Suitable nucleic acid sequences include those that are homologous, substantially similar, or identical to the nucleic acids described herein. In some aspects, homologous nucleic acid sequences will have a percent identity of at least about 75%, 76%, 77%, 78%, 79%, 80% 81%, 82%, 83%, 84%, 85%, 86%, 87%, 88%, 89%, 90%, 91%, 92%, 93%, 94%, 95%, 96%, 97%, 98%, 99%, or 100% to SEQ ID NO:265 or the respective complementary sequence. In other aspects, homologous nucleic acid sequences will have a sequence similarity of at least about 75%, 76%, 77%, 78%, 79%, 80% 81%, 82%, 83%, 84%, 85%, 86%, 88%, 89%, 90%, 91%, 92%, 93%, 94%, 95%, 96%, 97%, 98%, 99%, or 100% to SEQ ID NO:268 or the respective complementary sequence. In other aspects, homologous nucleic acid sequences will have a sequence similarity of at least about 75%, 76%, 77%, 78%, 79%, 80% 81%, 82%, 83%, 84%, 85%, 86%, 88%, 89%, 90%, 91%, 92%, 93%, 94%, 95%, 96%, 97%, 98%, 99%, or 100% to SEQ ID NO:266 or the respective complementary sequence. In other aspects, homologous nucleic acid sequences will have a sequence similarity of at least about 75%, 76%, 77%, 78%, 79%, 80% 81%, 82%, 83%, 84%, 85%, 86%, 88%, 89%, 90%, 91%, 92%, 93%, 94%, 95%, 96%, 97%, 98%, 99%, or 100% to SEQ ID NO:267 or the respective complementary sequence. Sequence similarity may be calculated using a number of algorithms known in the art, such as BLAST, described in Altschul, S. F., et al., J. Mol. Biol. 215:403-10, 1990. The nucleic acids may differ in sequence from the above-described nucleic acids due to the degeneracy of the genetic code. In general, a reference sequence will be 18 nucleotides, more usually 30 or more nucleotides, and may comprise the entire nucleic acid sequence of the composition for comparison purposes.

Nucleic acids that can hybridize to SEQ ID NO:265, SEQ ID NO:266, SEQ ID NO:267, or SEQ ID NO:268 are contemplated herein. Stringent hybridization conditions include conditions such as hybridization at 50° C. or higher and 0.1×SSC (15 mM sodium chloride/1.5 mM sodium citrate). Another example is overnight incubation at 42° C. in a solution of 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing in 0.1×SSC at about 65° C. Exemplary stringent hybridization conditions are hybridization conditions that are at least about 80%, 85%, 90%, or 95% as stringent as the above specific conditions. Other stringent hybridization conditions are known in the art and may also be employed to identify homologs of the nucleic acids of the present disclosure (Current Protocols in Molecular Biology, Unit 6, pub. John Wiley & Sons, N.Y. 1989).

It will be appreciated that the nucleotide sequences of the immunogenic nucleic acid plasmids may be varied to a certain extent without significantly adversely affecting their immunogenic properties. The nucleic acid sequence of such a variant nucleic acid plasmid molecule will usually differ by one or more nucleotides. The sequence changes may be substitutions, insertions, deletions, or a combination thereof. Techniques for mutagenesis of cloned genes are known in the art. Methods for site specific mutagenesis may be found in Gustin et al., Biotechniques 14:22, 1993; Barany, Gene 37:111-23, 1985; Colicelli et al., Mol. Gen. Genet. 199:537-9, 1985; and Sambrook et al., Molecular Cloning: A Laboratory Manual, CSH Press 1989, pp. 15.3-15.108 and all incorporated herein by reference. In summary, the invention relates to nucleic acid plasmid molecules, and variants or mutants thereof, capable of stimulating an innate immune response in a subject. Also, the invention encompasses the intermediary RNAs encoded by the described nucleic acids, as well as any resultant amino acid sequences encoded by the nucleic acid plasmids described herein.

In some aspects, where the nucleotide sequence of the immunogenic nucleic acid plasmid varies from the sequence provided in SEQ ID NOs:265, 266, 267, or 268, the CpG dinucleotides in the immunogenic nucleic acid plasmid are preferably left intact. Alternatively, if the nucleotide sequence of the immunogenic plasmid is altered such that a CpG dinucleotide is eliminated, the sequence of the immunogenic nucleic acid plasmid may be altered at another location such that the total number of CpG dinucleotides in the nucleic acid plasmid remains the same. Further CpG dinucleotides in addition to those already present in the immunogenic nucleic acid plasmid may also be introduced. Thus, for example, the immunogenic nucleic acid plasmids described herein comprise at least about 200, at least about 220, at least about 240, at least about 260, at least about 270, at least about 275, at least about 280, at least about 283, at least about 285, or at least about 288 CpG dinucleotides. In some embodiments, the immunogenic nucleic acid plasmid can comprise 283 CpG dinucleotides. In some embodiments, CpG dinucleotides in addition to those already present in the nucleotide sequences of pGCMB75.6 or pLacZMB75.6 are introduced into the plasmid.

In some aspects, where the nucleotide sequence of the immunogenic nucleic acid plasmid varies from the sequences provided herein, the CpG motif types in the immunogenic nucleic acid are varied to modulate the resultant activation of a cytosolic nucleic acid surveillance molecule, i.e., TLR21 and/or TLR9. For example, the number of immune stimulatory CpG motifs may be increased to enhance the activation of at least one cytosolic nucleic acid surveillance molecule responsive to an immunogenic nucleic acid plasmid. Alternatively, the number of non-immune stimulatory CpG motifs may be increased to reduce the activation of at least one cytosolic nucleic acid surveillance molecule. In some aspects, the number of stimulatory and nonstimulatory CpG motifs can be modified to enhance the activation of at least one cytosolic nucleic acid surveillance molecule and reduce the activation of at least one cytosolic nucleic acid surveillance molecule.

A suitable immunogenic nucleic acid plasmid molecule includes any of the immunogenic coding and noncoding nucleic acids described herein. Coding nucleic acid sequences encode at least a portion of a protein or peptide, while non-coding sequence does not encode any portion of a protein or peptide. According to the present invention, "non-coding" nucleic acids can include regulatory regions of a transcription unit, such as a promoter region. The term, "empty vector" can be used interchangeably with the term "non-coding," and particularly refers to a nucleic acid sequence in the absence of a protein coding portion, such as a plasmid vector without a gene insert. Expression of a protein encoded by the nucleic acid plasmids described herein is not required for inducing an immune response; therefore, the plasmids need not contain any coding sequences operatively linked to a transcription control sequence. However, further advantages may be obtained (i.e., antigen-specific and enhanced immunity) by including in the immunomodulatory composition at least one nucleic acid sequence (DNA or RNA) which encodes an immunogen and/or a cytokine. Such a nucleic acid sequence encoding an immunogen and/or a cytokine may be included in the immunogenic nucleic acid plasmids described herein, or may be included in a separate nucleic acid (e.g., a separate plasmid) in the composition.

In some embodiments of the immunomodulatory compositions described herein, the immunomodulatory composition comprises a liposomal delivery vehicle and at least one of the immunogenic nucleic acid plasmids described herein. Suitable immunomodulatory compositions are described in U.S. Patent Application Publications Nos. 2012/0064151 A1 and 2013/0295167 A1, the contents of both are hereby incorporated by reference in their entirety.

A suitable liposomal delivery vehicle comprises a lipid composition that is capable of delivering nucleic acid molecules to the tissues of a treated subject. In some embodiments, a liposomal delivery vehicle may be capable of remaining stable in a subject for a sufficient amount of time to deliver a nucleic acid molecule and/or a biological agent. For example, the liposomal delivery vehicle is stable in the recipient subject for at least about five minutes, for at least about 1 hour, or for at least about 24 hours.

A liposomal delivery vehicle as described herein comprises a lipid composition that is capable of fusing with the plasma membrane of a cell to deliver a nucleic acid molecule into a cell. When the nucleic acid molecule encodes one or more proteins, the nucleic acid:liposome complex has, in some aspects, a transfection efficiency of at least about 1 picogram (pg) of protein expressed per milligram (mg) of total tissue protein per microgram (μg) of nucleic acid delivered. For example, the transfection efficiency of a nucleic acid: liposome complex can be at least about 10 pg of protein expressed per mg of total tissue protein per μg of nucleic acid delivered; or at least about 50 pg of protein expressed per mg of total tissue protein per μg of nucleic acid delivered. The transfection efficiency of the complex may be as low as 1 femtogram (fg) of protein expressed per mg of total tissue protein per μg of nucleic acid delivered, with the above amounts being more preferred.

In some embodiments, the liposomal delivery vehicle of the present invention is between about 100 and 500 nanometers (nm) in diameter. For example, the liposomal delivery vehicle can be between about 150 and 450 nm or between about 200 and 400 nm in diameter.

Suitable liposomes include any liposome, such as those commonly used in, for example, gene delivery methods known to those of skill in the art. In some embodiments, liposomal delivery vehicles comprise multilamellar vesicle (MLV) lipids, extruded lipids, or both. In some aspects, the liposomal delivery vehicle is cationic. Methods for preparation of MLVs are well known in the art. In some aspects, liposomal delivery vehicles comprise liposomes having a polycationic lipid composition (i.e., cationic liposomes) and/or liposomes having a cholesterol backbone conjugated to polyethylene glycol. Exemplary cationic liposome compositions include, but are not limited to, N-[1-(2,3-dioleyloxy)propyl]-N,N,N-trimethylammonium chloride (DOTMA) and cholesterol, N-[1-(2,3-dioleoyloxy)propyl]-N,N,N-trimethylammonium chloride (DOTAP) and cholesterol, 1-[2-(oleoyloxy)ethyl]-2-oleyl-3-(2-hydroxyethyl)-imidazolinium chloride (DOTIM) and cholesterol, dimethyldioctadecylammonium bromide (DDAB) and cholesterol, and combinations thereof. In some aspects, the liposomal delivery vehicle comprises pairs of lipids selected from the group consisting of N-[1-(2,3-dioleyloxy)propyl]-N,N,N-trimethylammonium chloride (DOTMA) and cholesterol; N-[1-(2,3-dioleoyloxy)propyl]-N,N,N-trimethylammonium chloride (DOTAP) and cholesterol; 1-[2-

(oleoyloxy)ethyl]-2-oleyl-3-(2-hydroxyethyl)imidazolinium chloride (DOTIM) and cholesterol; and dimethyldioctadecylammonium bromide (DDAB) and cholesterol. In some aspects, the liposome composition for use as a delivery vehicle includes DOTIM and cholesterol.

Complexing a liposome with a herein described immunogenic nucleic acid plasmid may be achieved using methods standard in the art or as described in U.S. Pat. No. 6,693,086, the contents of which are hereby incorporated by reference in their entirety. A suitable concentration of nucleic acid plasmid to add to a liposome includes a concentration effective for delivering a sufficient amount of the immunogenic nucleic acid plasmid into a subject such that a systemic immune response is elicited. For example, from about 0.1 μg to about 10 μg of immunogenic nucleic acid plasmid can be combined with about 8 nmol liposomes, from about 0.5 μg to about 5 μg of immunogenic nucleic acid plasmid can be combined with about 8 nmol liposomes, or about 1.0 μg of immunogenic nucleic acid plasmid can be combined with about 8 nmol liposomes. The ratio of immunogenic nucleic acid plasmid to lipid (μg immunogenic nucleic acid plasmid:nmol lipid) in a composition can be at least about 1:1 immunogenic nucleic acid plasmid:lipid by weight (e.g., 1 μg immunogenic nucleic acid plasmid:1 nmol lipid). For example, the ratio of immunogenic nucleic acid plasmid to lipids can be at least about 1:5, at least about 1:10, or at least about 1:20. Ratios expressed herein are based on the amount of lipid in the composition, and not on the total amount of lipid in the composition. The ratio of immunogenic nucleic acid plasmid to lipids in a composition of the invention is suitably from about 1:1 to about 1:80 immunogenic nucleic acid plasmid:lipid by weight; from about 1:2 to about 1:40 immunogenic nucleic acid plasmid:lipid by weight; from about 1:3 to about 1:30 immunogenic nucleic acid:lipid by weight; or from about 1:6 to about 1:15 immunogenic nucleic acid plasmid:lipid by weight.

The concentration of the immunomodulatory composition, if elevated above a threshold, can be cytotoxic. For this reason, the concentration of the immunomodulatory composition as contemplated in the present disclosure is non-cytotoxic, i.e., at a level below this threshold. "Cytotoxicity," as used herein, refers to an abnormal cellular state such as failure to thrive, retarded growth, irregular microscopic appearance, and/or decline in immunoresponsiveness. In some aspects, the concentration of the immunomodulatory composition is between about 0.1 and about 250 ng/ml. In some aspects the concentration is between about 0.1 and about 200 ng/ml. In some aspects, the concentration of the immunomodulatory composition is between about 0.1 and about 150 ng/ml. In other aspects, the concentration of the immunomodulatory composition is between about 0.1 and about 100 ng/ml. In still other aspects, the concentration of the immunomodulatory complex is between about 0.1 and about 50 ng/ml. In other aspects, the concentration of the immunomodulatory composition is between about 1 and about 250 ng/ml. In some aspects, the concentration of the immunomodulatory composition is between about 10 and about 250 ng/ml. In some aspects, the concentration of the immunomodulatory composition is between about 50 and about 250 ng/ml. In some aspects, the concentration of the immunomodulatory composition is between about 100 and about 250 ng/ml. In some aspects, the concentration of the immunomodulatory composition is between about 150 and about 250 ng/ml. In still other aspects, the concentration of the immunomodulatory composition is between about 200 and about 250 ng/ml. In some embodiments, the concentration of the immunomodulatory composition is about or less than 120 ng/ml. In some aspects, the concentration of the immunomodulatory composition is non-cytotoxic.

Further provided herein are pharmaceutical compositions comprising an immunostimulatory composition as described supra and a pharmaceutically acceptable carrier. The immunomodulatory composition may be administered before, simultaneously with, or after immunostimulatory oligonucleotide. The pharmaceutical carriers for the individual immunomodulatory composition and immunostimulatory oligonucleotide may be but need not be the same carrier. The pharmaceutically acceptable carrier adapts the composition for administration by a route selected from intravenous, intramuscular, intramammary, intradermal, intraperitoneal, subcutaneous, by spray, by aerosol, in ovo, mucosal, transdermal, by immersion, oral, intraocular, intratracheal, intranasal, pulmonary, rectal, or other means known to those skilled in the art. The pharmaceutically acceptable carrier(s) may be a diluent, adjuvant, excipient, or vehicle with which the immunostimulatory composition is, or immunomodulatory composition and immunostimulatory oligonucleotide are, administered. Such vehicles may be liquids, such as water and oils, including those of petroleum, animal, vegetable, or synthetic origin, such as peanut oil, soybean oil, mineral oil, sesame oil, and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating, and coloring agents, etc. The concentration of the molecules of the invention in such pharmaceutical formulation may vary widely, i.e., from less than about 0.5%, usually to at least about 1% to as much as 15 or 20% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, $21^{st}$ Edition, Troy, D. B. ed., Lipincott Williams and Wilkins, Philadelphia, Pa. 2006, Part 5, Pharmaceutical Manufacturing pp 691-1092, (see especially pp. 958-989).

Methods are also provided herein for preparing the immunostimulatory composition, described supra, comprising combining the immunomodulator composition and the immunostimulatory oligonucleotide, to form the immunostimulatory composition; centrifuging the immunostimulatory composition to generate a supernatant and a pellet; and isolating the pellet.

Centrifuging the immunostimulatory composition will cause the sedimentation of the immunostimulatory composition. Isolating the pellet may be accomplished by pouring off the supernatant, pipetting off the supernatant, or removing the supernatant by other means so long as a portion of the pellet remains. It is to be expected that some pellet will be lost during the removal of the supernatant. Also, some immunostimulatory composition may remain in the supernatant even after centrifugation. In such a scenario, the supernatant may retain immunostimulatory properties. If immunostimulatory activity due to the presence of the immunostimulatory composition remains in the supernatant but it is desired to have nearly all of the immunostimulatory composition in the pellet, higher centrifugation speeds should be used. For example, if the supernatant contains immunostimulatory composition after centrifugation at 8,000 rpm, increasing the centrifugation to 14,000 rpm may bring down the remaining immunostimulatory composition.

Also provided herein are methods for stimulating toll-like receptor 21 (TLR21) comprising administering an immunostimulatory oligonucleotide and an immunomodulator composition, wherein the immunostimulatory oligonucleotide comprises at least one CpG motif and an guanine nucleotide enriched sequence at or near the 5' terminus of the immunostimulatory oligonucleotide, and wherein the immunomodulator composition comprises a noncoding nucleic acid plasmid and a cationic lipid delivery vehicle.

The immunostimulatory oligonucleotide and the immunomodulator composition can be administered by a route selected from intravenous, intramuscular, intramammary, intradermal, intraperitoneal, subcutaneous, by spray, by aerosol, in ovo, mucosal, transdermal, by immersion, oral, intraocular, intratracheal, intranasal, pulmonary, rectal, or other means known to those skilled in the art. In some aspects, the immunomodulator composition and the immunostimulatory oligonucleotide are present in synergistically effective amounts. The administration of the immunostimulatory composition and the immunomodulator composition may be sequential or simultaneous.

The concentration of the immunomodulator composition can be cytotoxic when above 250 μg/ml, and this cytotoxicity can more than offset any immunostimulatory effect of the immunomodulator. In some aspects of the present disclosures, the concentration of the immunomodulator is about 200 μg/ml. With administration of the immunostimulatory oligonucleotide, cytotoxic levels are not observed at or below the 10 μM range. Even higher concentrations of the immunostimulatory oligonucleotide may be tolerated by the recipient. In some aspects of the present disclosure the concentration of the immunostimulatory oligonucleotide is between about 10 μM and 0.5 μM. In some aspects the concentration of the immunostimulatory oligonucleotide is about 2 μM, and in some aspects, the concentration of the immunomodulator composition is greater than the concentration of the immunostimulatory oligonucleotide. Because cytotoxicity is a limiting factor with administration of the immunomodulator composition, in some aspects, the immunomodulator composition is present in non-cytotoxic amounts.

In each aspect of the methods presented herein, the immunomodulator composition and the immunostimulatory oligonucleotide can be any embodiment or aspect as described supra.

Also provided are methods for eliciting an immune response in a subject comprising administering any embodiment of the immunostimulatory composition described herein. Other embodiments included in the present disclosure include methods for eliciting an immune response in a subject comprising administering the immunostimulatory oligonucleotide and the immunomodulator composition described herein.

EXAMPLES

The following examples are provided to further describe some of the embodiments disclosed herein. The examples are intended to illustrate, not to limit, the disclosed embodiments.

The immunomodulator composition used in the following examples was a composition comprising a cationic lipid (DOTIM and cholesterol) and non-coding DNA (pMB75.6) (SEQ ID NO:266). The cationic lipid components were [1-[2-[9-(Z)-octadeceno-yloxy]]-2-[8](Z)-heptadecenyl]-3-[hydroxyethyl]imidazolinium chloride (DOTIM) and a synthetic neutral lipid cholesterol, formulated to produce liposomes approximately 200 nm in diameter (see, U.S. Pat. No. 6,693,086). The non-coding DNA component was a 4292 base-pair non-coding DNA plasmid (pMB75.6) (SEQ ID NO:266) produced in *E. coli*, which, being negatively charged, associates with the positively-charged (cationic) liposomes (see, U.S. Pat. No. 6,693,086). In the examples, the term "immunostimulatory nucleic acid plasmid" refers to pMB75.6.

Example 1: Combining TLR21-Active Oligodeoxynucleotides with an Immunomodulator Composition The activity of the immunomodulator composition on TLR21 was explored. Specifically, HEK293-NFκB-bsd-cTLR21 cells were seeded into 384 well plates at 10,000 cells/well in 45 μl growth medium. These cells were exposed to the oligonucleotide dissolved in growth medium and incubated at 37° for 3-4 days. 10 μl of culture supernatant per well was transferred to a 384 well plate and 90 μl of 50 mM $NaHCO_3/Na_2CO_3$, 2 mM $MgCl_2$, 5 mM para-nitrophenylphospate (pNP) pH 9.6 were added and reaction rates were determined by kinetic measurement of the temporal changes of the optical density at 405 nM (mOD405 nm/min).

Figure 2A:
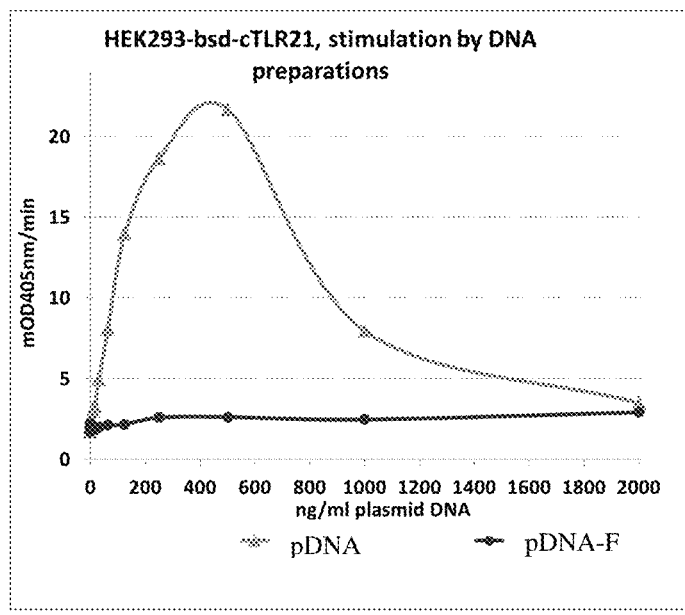
FIGS. 2A and 2B compare the immunogenicities of immunostimulatory plasmid DNA, plasmid DNA complexed with cationic liposomes, and immunostimulatory oligonucleotides.
Figure 2B:
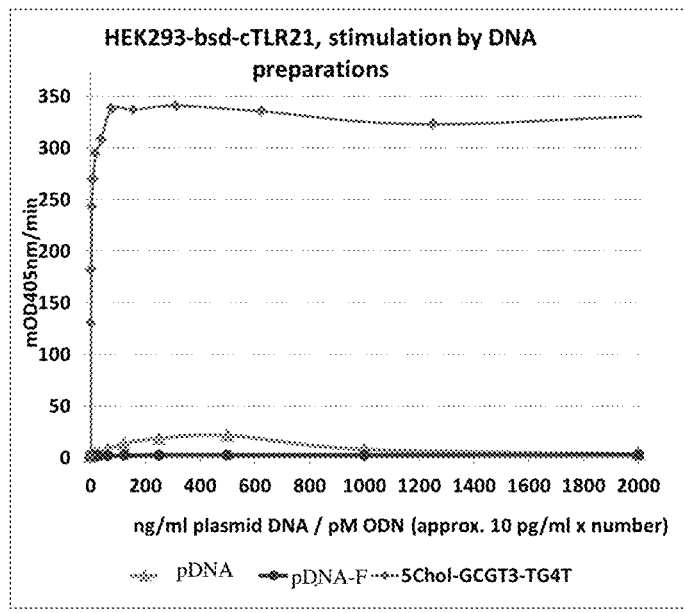

The immunostimulatory nucleic acid plasmid alone proved to be inactive in the concentration range considered (2 μg/ml and lower), while liposomally formulated immunostimulatory nucleic acid plasmid (pDNA-F) showed a weak but clear signal with a bell-shaped curve, indicating its interaction with TLR21 (FIG. 2A). The TLR21-stimulatory activity was, however, several orders of magnitude lower compared to 5-Chol-GCGT3-TG4T (SEQ ID NO:1) (FIGS. 2A and 2B), an oligonucleotide ligand optimized for interacting with this receptor.

TABLE 2

| ODN sequences | | |
|---|---|---|
| Immunostimulatory oligonucleotide | SEQ ID NO | Sequence |
| 5Chol-GCGT3-TG4T (ODN1) | SEQ ID NO: 1 | XTGGGGTTTTTTTGCGTTTTTGC GTTTTTGCGTTTT X = 5'-Cholesteryl |
| GCGT3-TG4T (ODN2) | SEQ ID NO: 252 | TGGGGTTTTTTTGCGTTTTTGCG TTTTTGCGTTTT |
| 2006-PTO (ODN3) | SEQ ID NO: 3 | tcgtcgttttgtcgttttgtcgtt |

The activity of the immunomodulator composition pDNA-F on TLR21 suggests that this receptor may indeed be a component of the in vivo action of the immunomodulator composition, but because the immunomodulator composition is a rather weak ligand for TLR21, this receptor may not be the sole and dominant cognate receptor.

Figure 3A:
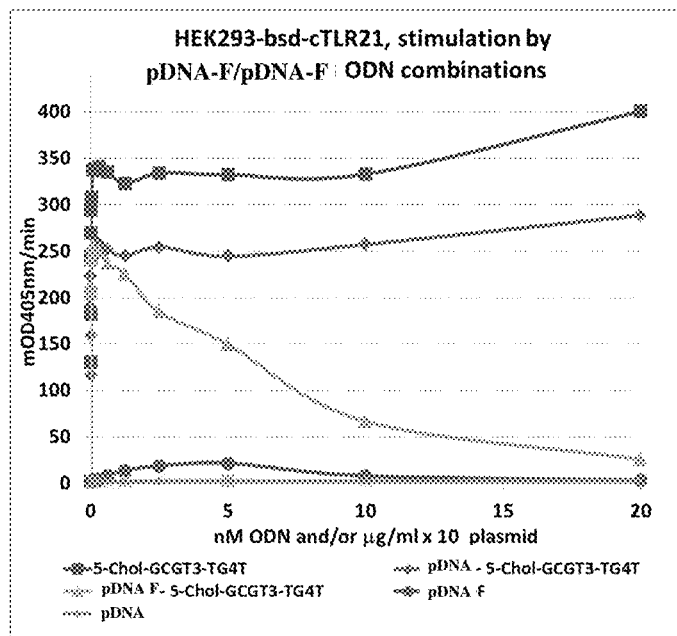
FIGS. 3A and 3B compare the immunogenicities of immunostimulatory plasmid DNA, immunostimulatory plasmid DNA complexed with cationic liposomes, immunostimulatory oligonucleotides, and combinations thereof.
Figure 3B:
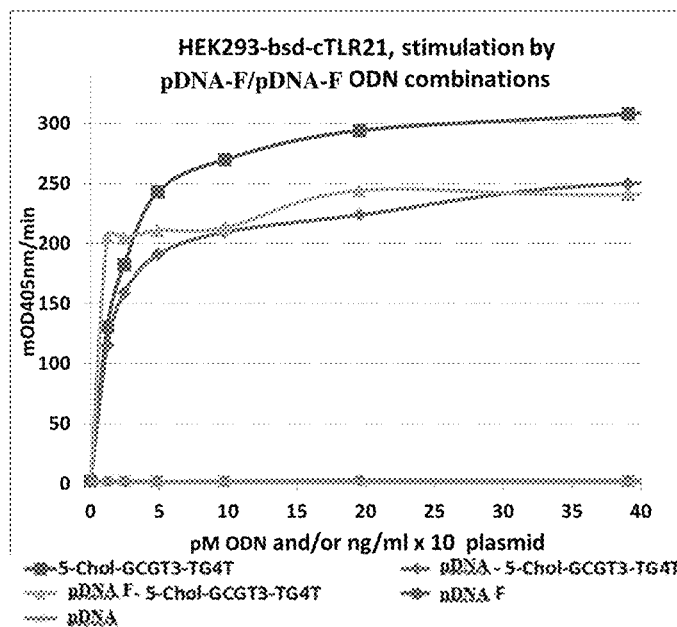

Example 2: Combination of 5-Chol-GCGT3-TG4T with the Immunostimulatory Nucleic Acid Plasmid and the Immunomodulator Composition 200 μg/ml solutions of the immunostimulatory nucleic acid plasmid alone and the immunomodulator composition and 2 μM solutions of 5-Chol-GCGT3-TG4T were prepared and incubated for 2 h at 4° C. Subsequently, from this solution, serial 1:2 dilutions were prepared and administered to HEK293-bsd-cTLR21 cells starting at 20 nM plasmid concentration (and 2 µg/ml plasmid concentration) according to the protocol in Example 1 and compared to a sample containing only 5-Chol-GCGT3-TG4T. All samples showed strong TLR21 stimulatory activity, with the only sample showing slightly higher peak values and an $EC_{50}$ of 2.44 pM (FIG. 3A, Table 3). Except for showing a slightly lower $V_{max}$, combination of 5-Chol-GCGT3-TG4T with the immunostimulatory nucleic acid plasmid, which by itself was totally inactive, led to little change in $EC_{50}$, compared to 5-Chol-GCGT3-TG4T alone (2.11 pM) (FIG. 3A, Table 3). By contrast, the liposome-containing sample (immunostimulatory oligonucleotide 5-Chol-GCGT3-TG4T and the immunomodulator composition) showed an activity maximum and a strong signal decrease at higher concentrations, (FIG. 3A). However, closer inspection of low concentrations (pM) revealed a defined activity plateau with a calculated $EC_{50}$ of 1.04 pM (FIG. 3B, Table 3). In this concentration range, the immunomodulator composition is also totally inactive (FIG. 3B) and is, by itself, not responsible for the lower $EC_{50}$.

TABLE 3

Half-maximum effective concentration
($EC_{50}$) and maximum signal velocity ($V_{max}$)

| Immunostimulant | $EC_{50}$ (pM) | Vmax milliOD 405 nm/min (mOD405/min) |
|---|---|---|
| 5-Chol-GCGT3-TG4T | 2.44 | 338 |
| 5-Chol-GCGT3-TG4T-pDNA combination | 2.11 | 260 |
| 5-Chol-GCGT3-TG4T-pDNA-F combination | 1.04 | 254 |

The results suggest that the combination of the TLR21-stimulatory ODN 5-Chol-GCGT3-TG4T and non-cytotoxic concentrations of either immunostimulatory nucleic acid plasmid or the immunomodulator composition leads to active mixtures. Furthermore, the combination of the TLR21-stimulatory ODN 5-Chol-GCGT3-TG4T and the immunomodulator composition is synergistic with respect to the $EC_{50}$ of TLR21 activation.

Example 3: Centrifugation of the Immunomodulator Composition and TLR21 Activity

An immunomodulator composition solution of 200n/ml plasmid concentration was centrifuged for 2 hours at 4° C. in an Eppendorf tabletop centrifuge at 14,000 rpm at 4° C. For comparison, a non-centrifuged aliquot was stored at 4° C. for 2 hours. The supernatant was removed and stored, while the pellet was resuspended in an equivalent volume. Titrations starting at a 2 mg/ml plasmid content were prepared for use in the TLR21 assay as described in Example 1, as it had been established earlier that the immunomodulator composition possesses some weak TLR21 stimulatory activity (see Example 1).

Figure 4:
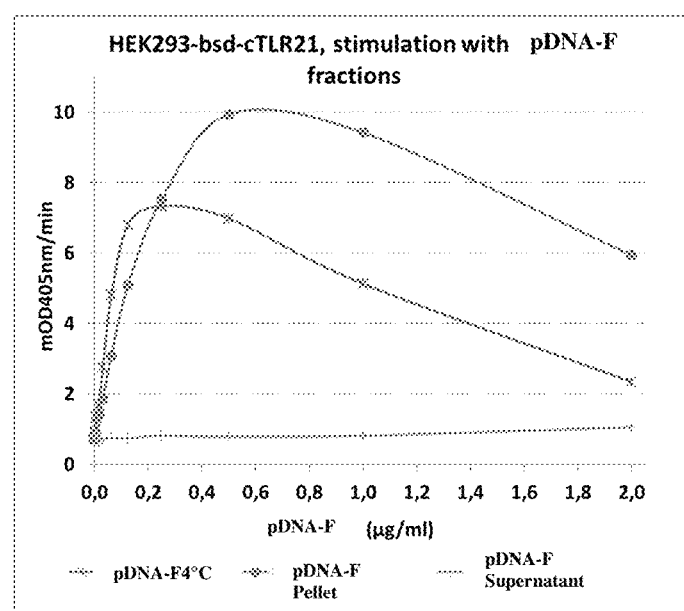
FIG. 4 illustrates the ability of pDNA-F fractions to stimulate TLR21-mediated immune responses in HEK293-bsd-cTLR21 cells. Specifically, the immunogenicity of pDNA-F stored at 4° C. was compared to that of pDNA-F obtained in the pellet ("pDNA-F pellet") and the supernatant ("pDNA-F supernatant") of a centrifuged sample.

Centrifugation of the immunomodulator composition resulted in a pellet that was difficult to resuspend with a pipette. All TLR21 stimulatory activity of immunomodulator composition was found in the pellet after centrifugation, and the supernatant was devoid of TLR21 activity (FIG. 4). The resuspended liposomes exhibited higher $EC_{50}$'s for TLR21 stimulation compared to the liposomes stored at 4° C. This effect may be due to changes in the liposomes after centrifugation (e.g., incomplete resuspension/dispersion).

Example 4: Combination of 5-Chol-GCGT3-TG4T with Immunomodulator Composition

Figure 5A:
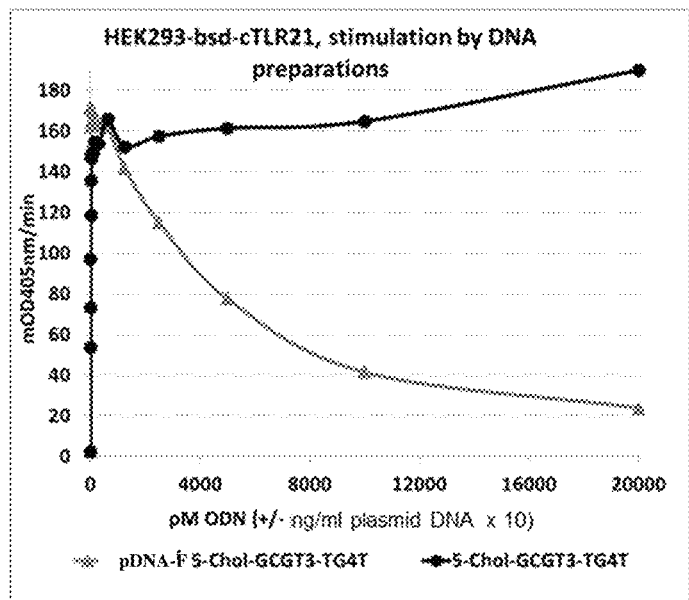
FIGS. 5A and 5B graphically depict the ability to generate a TLR21-mediated immune response in HEK293-bsd-cTLR21 cells of pDNA-F-5Chol-GCGT3-TG4T and 5Chol-GCGT3-TG4T at high and low concentrations, respectively.
Figure 5B:
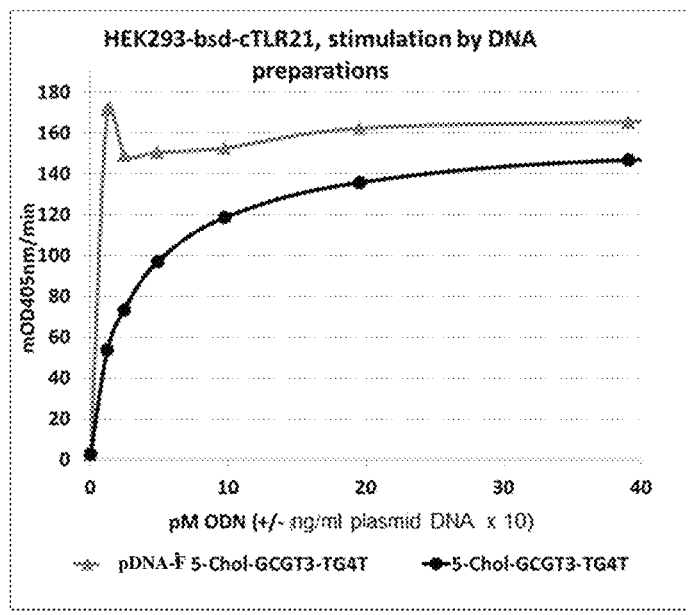

An immunomodulator composition/5-Chol-GCGT3-TG4T solution having a 200 µg/ml plasmid concentration and 2 µM 5-Chol-GCGT3-TG4T was prepared. A 2 µM solution of 5-Chol-GCGT3-TG4T was also prepared. Both samples were incubated for 2 hours at 4° C. 100 µl aliquots of these solutions were centrifuged in an Eppendorf tabletop centrifuge at 14,000 rpm at 4° C. for 2 hours for use in Example 5, while the remainder of the incubations were stored at 4° C. for analysis according to this Example 4. Both samples showed potent TLR21 stimulatory activity, but the immunomodulator composition/5-Chol-GCGT3-TG4T combination showed strongly decreasing signals at higher concentrations (FIG. 5A), likely a consequence of immunomodulator composition cytotoxicity. The respective $V_{max}$ values were similar when the immunomodulator composition component of the sample was considered at low toxicity concentrations (FIG. 5B, Table 4). However, the calculated $EC_{50}$ of the combination immunomodulator composition/5-Chol-GCGT3-TG4T was 4-fold lower than that of 5-Chol-GCGT3-TG4T alone (FIG. 5B, Table 4).

TABLE 4

Half-maximum effective concentration
($EC_{50}$) and maximum signal velocity ($V_{max}$)

| Immunostimulant | $EC_{50}$ (pM) | Vmax milliOD 405 nm/min (mOD405/min) |
|---|---|---|
| 5-Chol-GCGT3-TG4T | 3.2 | 158 |
| 5-Chol-GCGT3-TG4T (centrifugation supernatant) | 2.5 | 160 |
| 5-Chol-GCGT3-TG4T (centrifugation pellet) | 819 | 184 |
| 5-Chol-GCGT3-TG4T-pDNA-F combination | 0.62 | 160 |
| 5-Chol-GCGT3-TG4T-pDNA-F combination (centrifugation supernatant) | 5145 | 184 |
| 5-Chol-GCGT3-TG4T-pDNA-F combination (centrifugation pellet) | 1.81 | 140 |

Example 5: Centrifugation of Immunomodulator Composition/5-Chol-GCGT3-TG4T and 5-Chol-GCGT3-TG4T An immunomodulator composition/5-Chol-GCGT3-TG4T solution having a 200 µg/ml plasmid concentration and 2 µM 5-Chol-GCGT3-TG4T was prepared. A 2 µM solution of 5-Chol-GCGT3-TG4T was also prepared. Both samples were incubated for 2 hours at 4° C. 100 µl aliquots of these solutions were centrifuged in an Eppendorf tabletop centrifuge at 14,000 rpm at 4° C. for 2 hours. The supernatants were removed and stored, while the pellets were resuspended in 100 µl. Subsequently, from these solutions, serial 1:2 dilutions were prepared and administered to HEK293-bsd-cTLR21 cells starting at 20 nM plasmid concentration (and 2 µg/ml plasmid concentration) and compared to a sample containing only 5-Chol-GCGT3-TG4T.

Figure 6A:
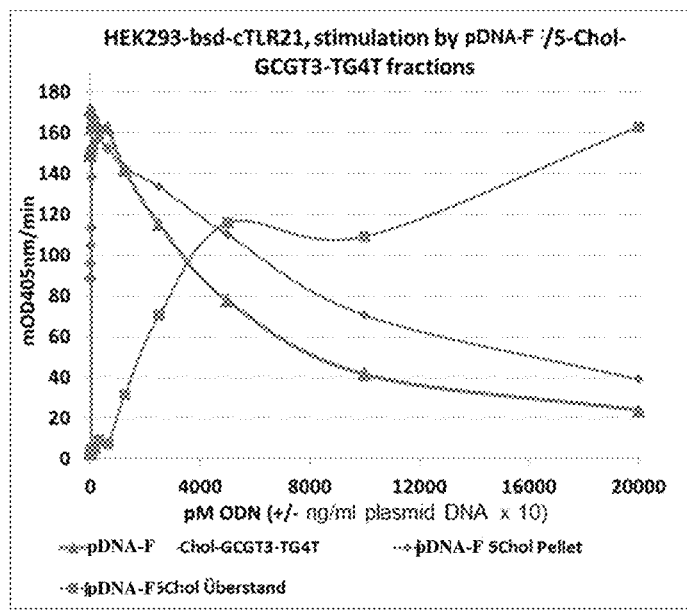
FIGS. 6A and 6B compare the ability of high and low concentrations, respectively, of pDNA-F-5Chol-GCGT3-TG4T to generate a TLR21-mediated immune response in HEK293-bsd-cTLR21 cells to that of 5Chol-GCGT3-TG4T obtained in the pellet ("pDNA-F 5Chol pellet") and supernatant ("pDNA-F 5Chol Uberstand") of a centrifuged pDNA-F sample.
Figure 6B:
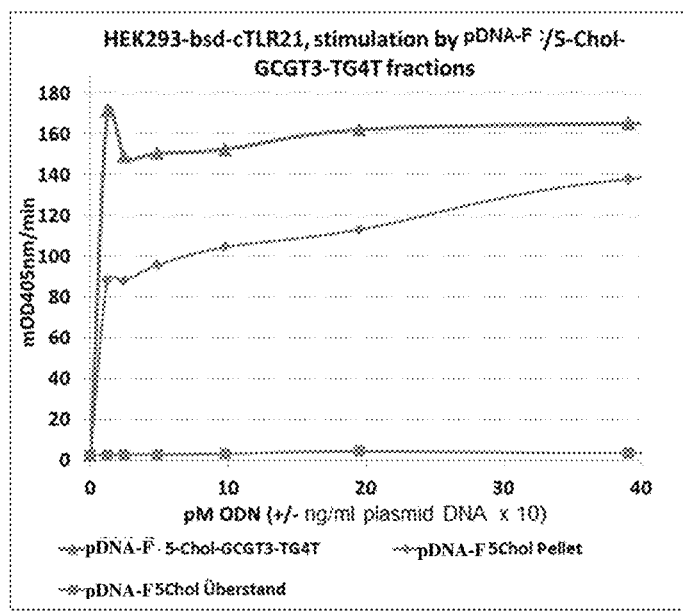
Figure 7A:
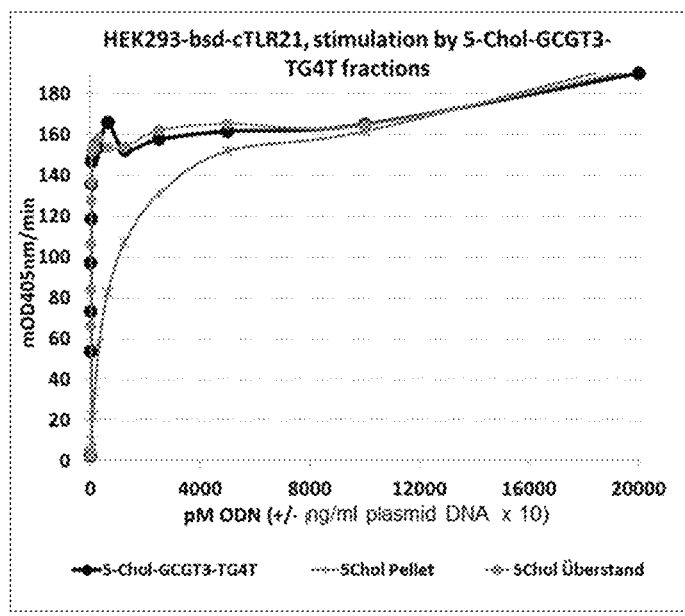
FIGS. 7A and 7B compare the ability of high and low concentrations, respectively, of 5Chol-GCGT3-TG4T to generate a TLR21-mediated immune response in HEK293-bsd-cTLR21 cells to that of 5Chol-GCGT3-TG4T obtained in the pellet ("5Chol pellet") and supernatant ("5Chol Uberstand") of a centrifuged pDNA-F sample.
Figure 7B:
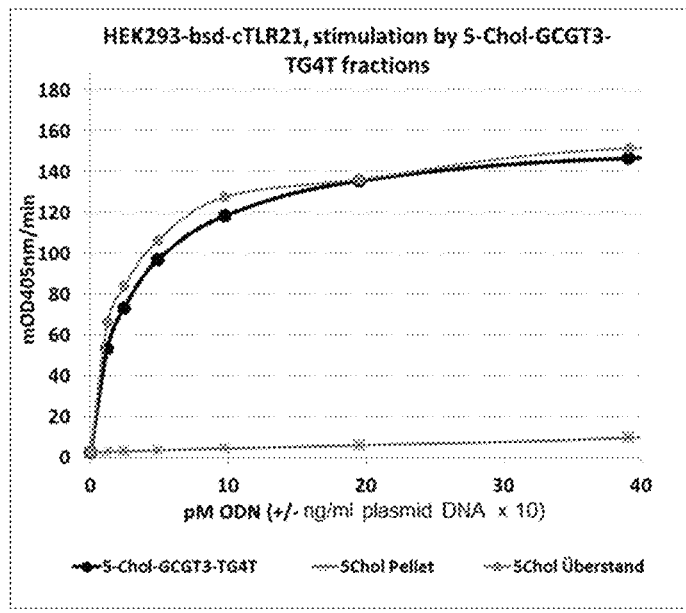

Centrifugation of the immunomodulator composition/5-Chol-GCGT3-TG4T combination led to a clearly visible pellet, while no visible pellet was observed for 5-Chol-GCGT3-TG4T. The immunomodulator composition/5-Chol-GCGT3-TG4T combination pellet ("pDNA-F 5Chol Pellet") was difficult to resuspend, but in the TLR21 assay as described in Example 1, it contained virtually all stimulating activity (FIGS. 6A and 6B), with only traces being detected in the supernatant ("pDNA-F 5Chol Uberstand") (FIG. 6B, Table 4), albeit with higher $EC_{50}$ than the original sample ("pDNA-f F-Chol-GCGT3-TG4T") (Table 4). This result suggests that after mixing with immunomodulator composition, 5-Chol-GCGT3-TG4T is quantitatively physically associated with the liposomal fraction. 5-Chol-GCGT3-TG4T alone, which, when centrifuged, remains almost exclusively (an estimated 99%, Table 4) in the supernatant, as expected from a soluble compound (FIGS. 7A and 7B).

Example 6: Combination of 5-Chol-GCGT3-TG4T and Immunomodulator Composition

An immunostimulatory composition with 200 µg/ml plasmid concentration and 2 µM 5-Chol-GCGT3-TG4T was prepared. A 2 µM solution of 5-Chol-GCGT3-TG4T was also prepared. Both samples were incubated for 2 hours at 4° C. 100 µl aliquots of these solutions were centrifuged in an Eppendorf tabletop centrifuge at 14,000 rpm at 4° C. for 2 hours for use in Example 7, while the remainder of the incubations were stored at 4° C. for analysis according to this Example 6. The supernatants were removed and stored, while the pellets were resuspended in 200 Subsequently, from these solutions, serial 1:2 dilutions were performed and administered to HEK293-bsd-cTLR21 cells for TLR21 analysis according to the protocol in Example 1. The starting plasmid concentration was 20 nM (and 2 µg/ml plasmid concentration) and compared to a sample containing only 5-Chol-GCGT3-TG4T.

Figure 8A:
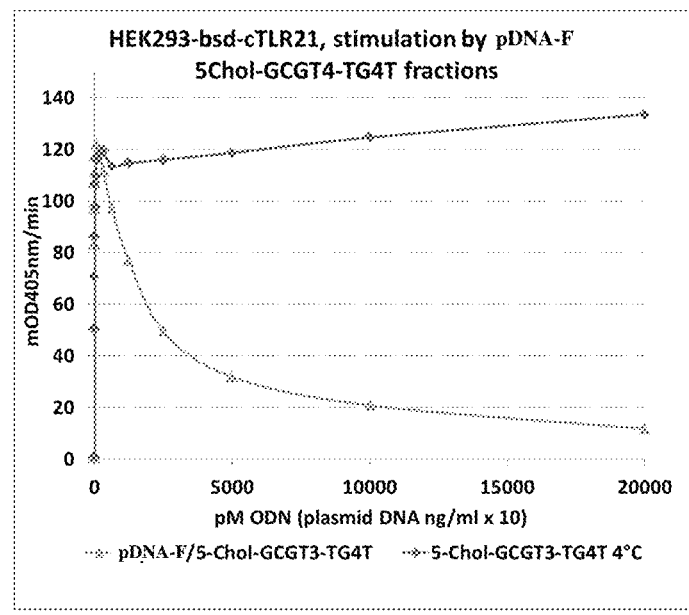
FIGS. 8A and 8B compare the ability of high and low concentrations, respectively, of 5Chol-GCGT3-TG4T ("5Chol-GCGT3-TG4T 4° C.") to generate a TLR21-mediated immune response in HEK293-bsd-cTLR21 cells to that of pDNA-F combined with 5Chol-GCGT3-TG4T "pDNA-F/5-Chol-GCGT3-TG4T").
Figure 8B:
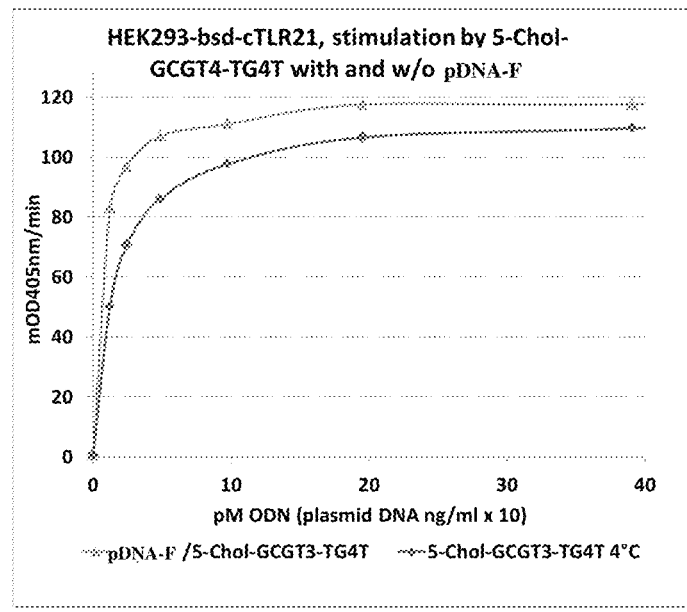

Both samples ("5-Chol-GCGT3-TG4T" and "pDNA-F/5-Chol-GCGT3-TG4T") showed potent TLR21 stimulatory activity, but the immunomodulator composition/5-Chol-GCGT3-TG4T combination ("pDNA-F/5-Chol-GCGT3-TG4T") showed strongly decreasing signals at higher concentrations (FIG. 8A), likely a consequence of immunomodulator composition cytotoxicity. The respective $V_{max}$ values were very similar when the stimulatory activity of immunomodulator composition-containing sample was considered at low toxicity concentrations (FIG. 8B, Table 5). However, the calculated $EC_{50}$ of the combination immunomodulator composition/5-Chol-GCGT3-TG4T was 2-fold lower than that of 5-Chol-GCGT3-TG4T ("5-Chol-GCGT3-TG4T") alone (FIG. 8B, Table 5).

TABLE 5

Half-maximum effective concentration ($EC_{50}$) and maximum signal velocity ($V_{max}$)

| Immunostimulant | $EC_{50}$ picomolar (pM) | Vmax milliOD 405 nm/min (mOD405/min) |
|---|---|---|
| 5-Chol-GCGT3-TG4T | 2.2 | 120 |
| 5-Chol-GCGT3-TG4T (centrifugation supernatant) | 2.7 | 153 |
| 5-Chol-GCGT3-TG4T (centrifugation pellet) | 530 | 139 |
| 5-Chol-GCGT3-TG4T-pDNA-F combination | 0.94 | 113 |
| 5-Chol-GCGT3-TG4T-pDNA-F combination (centrifugation supernatant) | 14983 | 224 |
| 5-Chol-GCGT3-TG4T-pDNA-F combination (centrifugation pellet) | 8.96 | 116 |

Figure 9A:
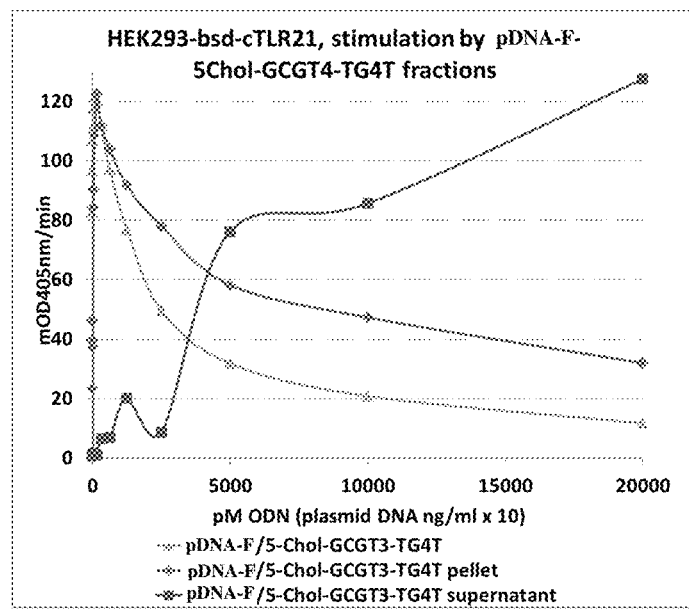
FIGS. 9A and 9B compare the ability of high and low concentrations, respectively, of pDNA-F combined with 5Chol-GCGT3-TG4T ("pDNA-F/5-Chol-GCGT3-TG4T") to generate a TLR21-mediated immune response in HEK293-bsd-cTLR21 cells to that of pDNA-F combined with 5Chol-GCGT3-TG4T obtained in the pellet ("pDNA-F/5-Chol-GCGT3-TG4T pellet") and supernatant ("pDNA-F/5-Chol-GCGT3-TG4T supernatant") of a centrifuged pDNA-F sample.
Figure 9B:
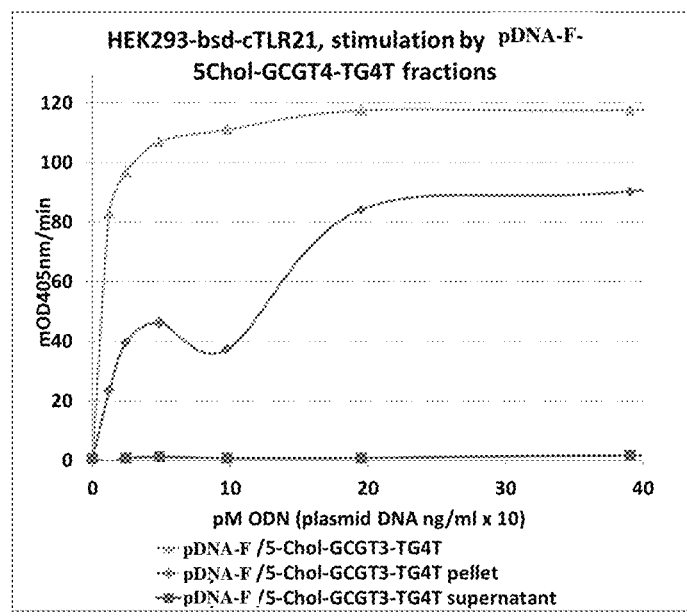

Example 7: Centrifugation of Immunomodulator Composition/5-Chol-GCGT3-TG4T and 5-Chol-GCGT3-TG4T Centrifugation of the immunomodulator composition/5-Chol-GCGT3-TG4T combination led to a clearly visible pellet, while no visible pellet was observed for 5-Chol-GCGT3-TG4T. The immunomodulator composition/5-Chol-GCGT3-TG4T combination pellet was difficult to resuspend, but in a TLR21 assay as described in Example 1, it ("pDNA-F/5-Chol-GCGT3-TG4T pellet") contained virtually all of the stimulating activity (FIG. 9B), albeit with higher $EC_{50}$ than the original sample (Table 5)), with only traces being detected in the supernatant ("pDNA-F/5-Chol-GCGT3-TG4T supernatant") (FIG. 9B, Table 5). This result suggests that after mixing with immunomodulator composition, the 5-Chol-GCGT3-TG4T is physically associated with the liposomal fraction. Both fractions were compared to non-centrifuged immunomodulator composition/5-Chol-GCGT3-TG4T ("pDNA-F/5-Chol-GCGT3-TG4T")

Example 8: Combination of 5-Chol-GCGT3-TG4T with Immunomodulator Composition An immunomodulator composition solution of 200 µg/ml plasmid concentration and 2 µM 5-Chol-GCGT3-TG4T was prepared. A 2 µM 5-Chol-GCGT3-TG4T sample also was prepared. Both samples were incubated for 2 hours at 4° C. 100 µl aliquots of these solutions were centrifuged in an Eppendorf tabletop centrifuge at 14,000 rpm at 4° C. for 2 hours for use in Example 9, while the remainder of the incubations were stored at 4° C. for analysis according to this Example 8. The supernatants were removed and stored, while the pellets were resuspended in 100 µl. Subsequently, from these solutions, serial 1:2 dilutions were prepared and administered to HEK293-bsd-cTLR21 cells according to the protocol of Example 1, starting at 20 nM plasmid concentration (and 2 µg/ml plasmid concentration) and compared to a sample containing only 5-Chol-GCGT3-TG4T.

Figure 10A:
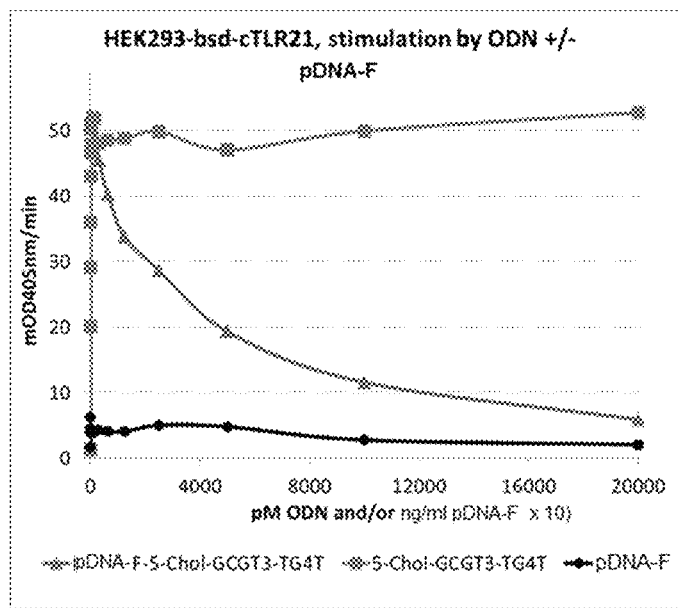
FIGS. 10A and 10B compare the ability of high and low concentrations, respectively, of pDNA-F combined with 5Chol-GCGT3-TG4T ("pDNA-F-5-Chol-GCGT3-TG4T") to generate a TLR21-mediated immune response in HEK293-bsd-cTLR21 cells to that of pDNA-F and immunostimulatory oligonucleotide 5-Chol-GCGT3-TG4T.
Figure 10B:
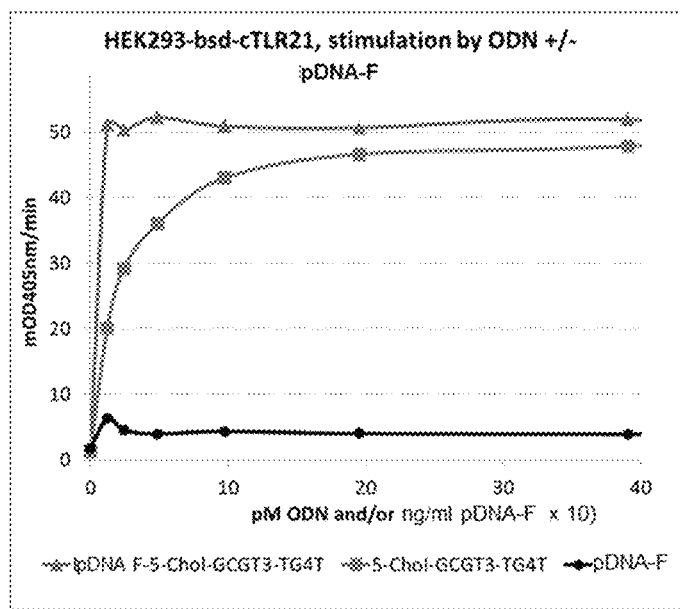

Both samples showed potent TLR21 stimulatory activity, but the 5-Chol-GCGT3-TG4T/immunomodulator composition combination ("pDNA-F/5-Chol-GCGT3-TG4T") showed strongly decreasing signals at higher concentrations (FIG. 10A), similar to that of the immunomodulator by itself ("pDNA-F") and likely a consequence of immunomodulator composition cytotoxicity. The immunostimulatory oligonucleotide ("5-Chol-GCGT3-TG4T") exhibited greater stimulatory activity at higher concentrations than did either sample containing the immunomodulator composition. The respective $V_{max}$ values were very similar when the stimulatory activity of immunomodulator composition component of the sample was considered at low toxicity concentrations (FIG. 10B, Table 6). However, the calculated $EC_{50}$ of the combination immunomodulator composition/5-Chol- GCGT3-TG4T ("pDNA-F/5-Chol-GCGT3-TG4T") was 4-fold lower than that of 5-Chol-GCGT3-TG4T alone ("5-Chol-GCGT3-TG4T") (FIG. 10B, Table 6). The immunomodulator composition alone ("Bay 98-F") showed only minimal activity whose additive effect could not explain the increased activity of immunomodulator composition/5-Chol-GCGT3-TG4T versus 5-Chol-GCGT3-TG4T alone.

TABLE 6

Half-maximum effective concentration
($EC_{50}$) and maximum signal velocity ($V_{max}$):

| Immunostimulant | $EC_{50}$ picomolar (pM) | Vmax milliOD 405 nm/min (mOD405/min) |
|---|---|---|
| 5-Chol-GCGT3-TG4T | 2.47 | 53 |
| 5-Chol-GCGT3-TG4T-pDNA-F combination | 0.59 | 51 |
| 5-Chol-GCGT3-TG4T-pDNA-F combination (centrifugation supernatant) | 22.0 | 47 |
| 5-Chol-GCGT3-TG4T-pDNA-F combination (centrifugation pellet) | 1.06 | 47 |

Example 9: Centrifugation of Immunomodulator Composition

Figure 11A:
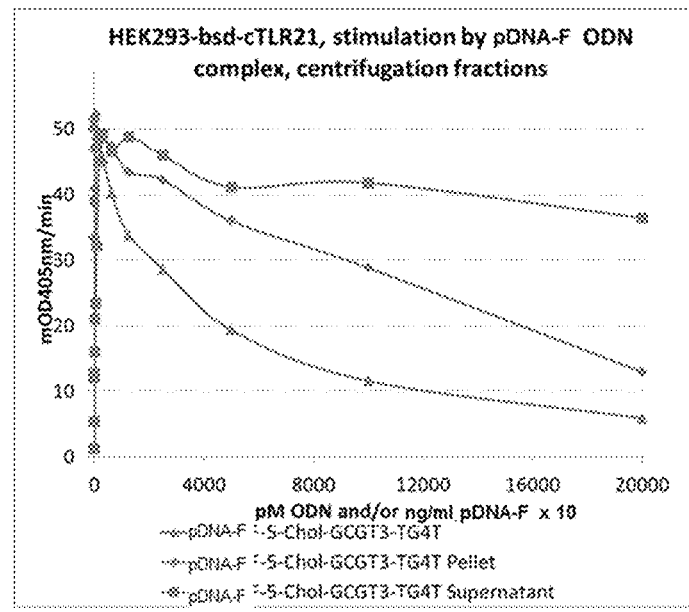
FIGS. 11A and 11B compare the ability of high and low concentrations, respectively, of pDNA-F combined with 5Chol-GCGT3-TG4T ("pDNA-F-5-Chol-GCGT3-TG4T") to generate a TLR21-mediated immune response in HEK293-bsd-cTLR21 cells to that of pDNA-F combined with 5Chol-GCGT3-TG4T obtained in the pellet ("pDNA-F-5-Chol-GCGT3-TG4T pellet") and supernatant ("pDNA-F-5-Chol-GCGT3-TG4T") of a centrifuged pDNA-F sample.
Figure 11B:
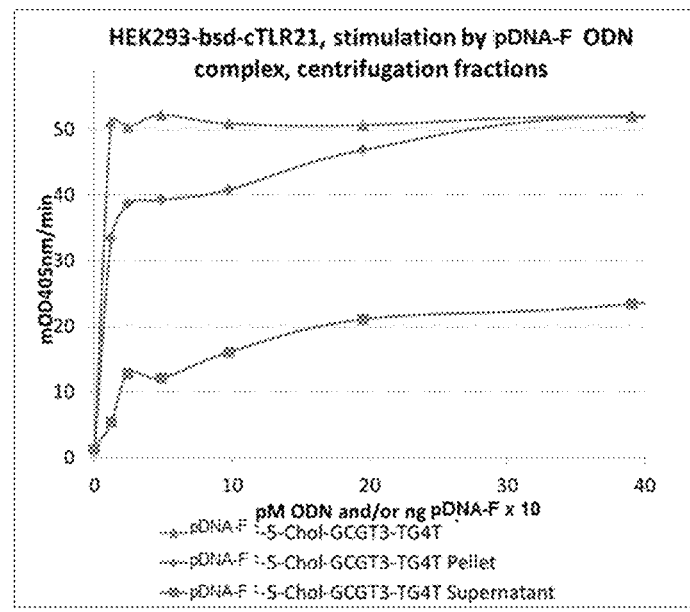

Centrifugation of immunomodulator composition/5-Chol-GCGT3-TG4T combination led to a clearly visible pellet, while for 5-Chol-GCGT3-TG4T, no visible pellet was observed. The immunomodulator composition/5-Chol-GCGT3-TG4T combination pellet ("pDNA-F/5-Chol-GCGT3-TG4T Pellet") was difficult to resuspend, but in a TLR21 assay as described in Example 1, it contained >95% of the stimulating activity (FIG. 11B), albeit with higher $EC_{50}$ than the original sample, with only a small fraction (<5%) being detected in the supernatant ("pDNA-F/5-Chol-GCGT3-TG4T Supernatant") (FIG. 11B, Table 6) and only slightly less than the non-centrifuged sample at low immunomodulator composition concentrations ("pDNA-F/5-Chol-GCGT3-TG4T"). This result suggests that after mixing with immunomodulator composition, 5-Chol-GCGT3-TG4T is quantitatively physically associated with the liposomal fraction.

Example 10: Combination of GCGT3-TG4T with Immunomodulator Composition

An immunomodulator composition solution of 200 µg/ml plasmid concentration and 2 µM GCGT3-TG4T (SEQ ID NO:252; the same oligonucleotide sequence as 5-Chol-GCGT3-TG4T (SEQ ID NO:1) but without the cholesteryl modification) was prepared. Also, a 2 µM GCGT3-TG4T sample was prepared, and both samples were incubated for 2 hours at 4° C. 100 µl aliquots of these solutions were centrifuged in an Eppendorf tabletop centrifuge at 14,000 rpm at 4° C. for 2 hours for use in Example 11, while the remainder of the incubations were stored at 4° C. for analysis according to this Example 10. The supernatants were removed and stored, while the pellets were resuspended in 100 µl. Subsequently, from these solutions, serial 1:2 dilutions were prepared and administered to HEK293-bsd-cTLR21 cells according to the protocol in Example 1, starting at 20 nM plasmid concentration (and 2 µg/ml plasmid concentration) and compared to a sample containing only GCGT3-TG4T.

Figure 12A:
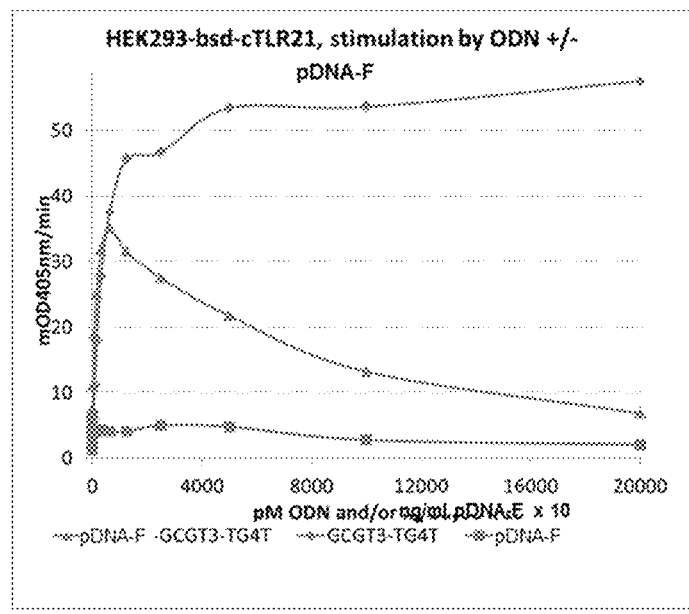
FIGS. 12A and 12B compare the ability of high and low concentrations, respectively, of pDNA-F, immunostimulatory oligonucleotide GCGT3-TG4T, and pDNA-F complexed with GCGT3-TG4T ("pDNA-F-GCGT3-TG4T") to generate TLR21-mediated immune responses in HEK293-bsd-cTLR21 cells.
Figure 12B:
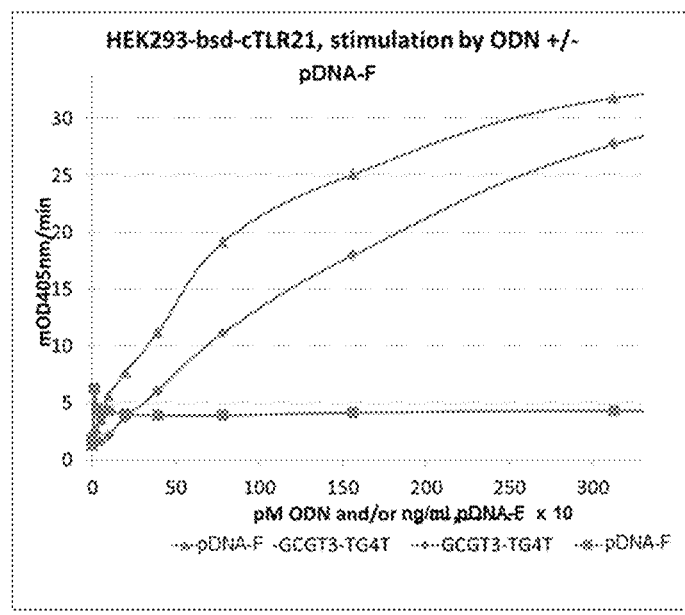

Both samples showed potent TLR21 stimulatory activity, but the GCGT3-TG4T/immunomodulator composition combination ("pDNA-F/5-Chol-GCGT3-TG4T") showed strongly decreasing signals at higher concentrations (FIG. 12A), likely a consequence of immunomodulator composition cytotoxicity. The respective $V_{max}$ values were very similar, when the stimulatory activity of immunomodulator composition component of the sample was considered at low toxicity concentrations (FIG. 12B, Table 7). However, the calculated $EC_{50}$ of the combination immunomodulator composition/GCGT3-TG4T was more than 4-fold lower than that of GCGT3-TG4T alone (Table 7). The immunomodulator composition alone ("pDNA-F") showed only minimal activity whose additive effect could not explain the increased activity of immunomodulator composition/GCGT3-TG4T versus GCGT3-TG4T alone.

TABLE 7

Half-maximum effective concentration
($EC_{50}$) and maximum signal velocity ($V_{max}$)

| Immunostimulant | $EC_{50}$ picomolar (pM) | Vmax milliOD 405 nm/min (mOD405/min) |
|---|---|---|
| GCGT3-TG4T | 324 | 56 |
| GCGT3-TG4T-pDNA-F combination | 69.4 | 51 |
| GCGT3-TG4T-pDNA-F combination (centrifugation supernatant) | 860 | 43 |
| GCGT3-TG4T-pDNA-F combination (centrifugation pellet) | 252 | 36 |

Example 11: Centrifugation of Immunomodulator Composition/GCGT3-TG4T

Figure 13A:
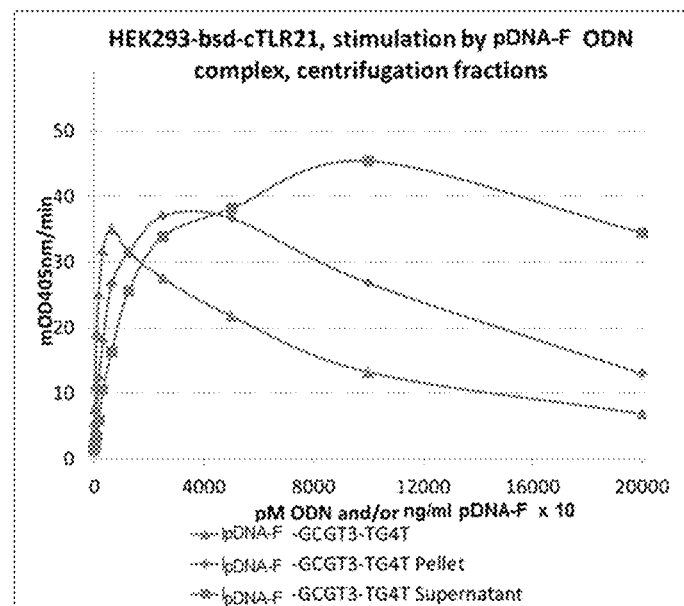
FIGS. 13A and 13B compare the ability of high and low concentrations, respectively, of pDNA-F combined with immunostimulatory oligonucleotide GCGT3-TG4T ("pDNA-F-GCGT3-TG4T") to generate a TLR21-mediated immune response in HEK293-bsd-cTLR21 cells to that of pDNA-F combined with immunostimulatory oligonucleotide GCGT3-TG4T obtained in the pellet ("pDNA-F-GCGT3-TG4T pellet") and supernatant ("pDNA-F-GCGT3-TG4T supernatant") of a centrifuged pDNA-F sample.
Figure 13B:
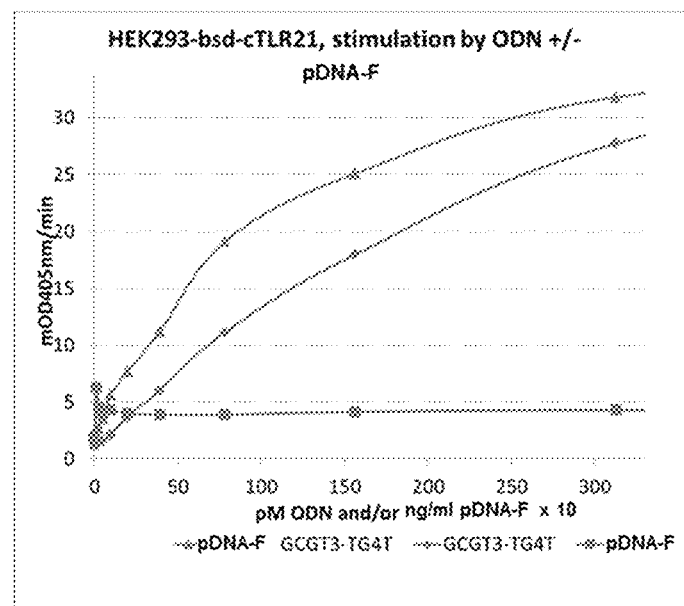

Centrifugation of the immunomodulator composition/GCGT3-TG4T combination led to a clearly visible pellet. The immunomodulator composition/GCGT3-TG4T combination pellet was difficult to resuspend, but in a TLR21 assay as described in Example 1 it ("pDNA-F/GCGT3-TG4T Pellet") contained >3× more stimulating activity (FIG. 13B), albeit with higher $EC_{50}$ than the original sample ("pDNA-F/GCGT3-TG4T") than the supernatant ("pDNA-F/GCGT3-TG4T Supernatant") (FIG. 13B, Table 7). This result suggests that after mixing with immunomodulator composition, the GCGT3-TG4T is quantitatively physically associated with the liposomal fraction, although perhaps not as efficiently as the cholesteryl-derivatized 5-Chol-GCGT3-TG4T.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

Example 12: In Vivo Study of Efficacy of Immune Stimulants in a Newcastle Disease Vaccination Model in Chickens To determine the suitability and efficacy of ODN1, ODN2, and ODN3 as immune stimulants, each was tested in three different concentrations.

The following immune stimulants were investigated:

ODN1:
(SEQ ID NO: 1)
[CholTEG]-TGGGGTTTTTTTGCGTTTTTGCGTTTTTGCGTTTT ("5Chol-GCGT3-TG4T")
([CholTEG]= 5'-triethyleneglycol-linked
cholesteryl modification),

ODN2:
(SEQ ID NO: 252)
TGGGGTTTTTTTGCGTTTTTGCGTTTTTGCGTTTT ("GCGT3-TG4T"),

ODN3:
(SEQ ID NO: 3)
tcgtcgttttgtcgttttgtcgtt ("2006-PTO").

Each immune stimulant was added to an oil emulsion containing a suboptimal concentration of an inactivated Newcastle disease virus (NDV) according to Table 9. For the preparaton of the suboptimal NDV vaccine, the NDV antigen batch was diluted 50 times in NDV-negative allantoic fluid (AF). The efficacies of ODN1, ODN2, and ODN3 in combination with a suboptimal dosage of a Newcastle disease vaccine were tested in SPF layer chickens (Leghorn). The serological response was measured and compared to the similar suboptimal NDV vaccine without the immune stimulant. The antibody titre was determined at different time points after vaccination to investigate whether the addition of the immune stimulants leads to an earlier immune response. To determine the most optimal dosage of the three ODNs, each was supplemented in three different doses of 100 ng, 1000 ng and 5000 ng to the suboptimal NDV vaccine, resulting in nine immune stimulant groups. Besides these nine immune stimulant groups, five control groups were incorporated in this study, consisting of a suboptimal NDV vaccine without immune stimulant group, the non-diluted NDV vaccine group, a negative control group (immune stimulants in combination with adjuvant) and two positive control groups with polyinosinic:polycytidylic acid (poly I:C) at two different concentrations (Table 8).

The following parameters were tested: health of the chickens (data not shown) and serology by the Haemagglutination inhibition (HI) assay.

TABLE 8

| Study Design | | |
|---|---|---|
| Test Article/Control Item | Test Group | Number (n) |
| Subootimal NDV + ODN1 100 ng | T01 | 10 |
| Suboptimal NDV + ODN1 1000 ng | T02 | 10 |
| Suboptimal NDV + ODN1 5000 ng | T03 | 10 |
| Suboptimal NDV + ODN2 100 ng | T04 | 10 |
| Suboptimal NDV + ODN2 1000 ng | T05 | 10 |
| Suboptimal NDV + ODN2 5000 ng | T06 | 10 |
| Suboptimal NDV + ODN3 100 ng | T07 | 10 |
| Suboptimal NDV + ODN3 1000 ng | T08 | 10 |
| Suboptimal NDV + ODN3 5000 ng | T09 | 10 |
| Suboptimal NDV | T10 | 10 |
| Optimal NDV (non-diluted vaccine) | T11 | 10 |
| ODN1 5000 ng + Adjuvant* | T12a | 3 |
| ODN2 5000 ng + Adjuvant* | T12b | 3 |
| ODN3 5000 ng + Adjuvant* | T12c | 3 |
| Adjuvant alone (Stimune)* | T12d | 1 |
| Suboptimal NDV + 10 µg Poly I:C | T13 | 9 |
| Suboptimal NDV + 100 µg Poly I:C | T14 | 9 |

*3 animals were allocated as control for each immune stimulant in combination with the adjuvant (Stimune). One animal received the adjuvant only.
All animals arrived at 3 weeks old.
All animals were vaccinated at 5 weeks old. All vaccinations were performed at day 0 by intramuscular injection.
Blood sampling/serology was performed on days 0 (before vaccination), 7, 14, and 21.
Clinical scoring of all animals was performed daily.

Chickens enrolled in treatment groups T01-T14 received the Test Article or Control Item according to the study design. In groups T13 and T14, nine instead of ten chickens per group were vaccinated due to the loss of two animals before the start of the study.

Chickens allocated to treatment groups T01, T02, T03, T04, T05, T06, T07, T08 and T09 were vaccinated with a suboptimal NDV suspension containing 1 of 3 different immune stimulants (ODNs), each in 3 different concentrations (100, 1000, 5000 ng/dose). For the preparation of the water in oil emulsions, the NDV antigen suspension and immune stimulant (water phase) were formulated together with the adjuvant Stimune (oil phase) at a ratio of 4:5 (Table 9).

TABLE 9

| Preparation of Test Articles and Control Items | | | | | | | | |
|---|---|---|---|---|---|---|---|---|
| | | Water Phase | | | | Oil Phase | | |
| | | | | | Total | | | |
| | | | | | volume | Add volume | | |
| | | NDV | Neg. | Stimune | water | water phase | | |
| | | batch | AF | 600 ng/µl | phase | to Stimune | Stimune | Total |
| Group | Name | (µl) | (µl) | (µl) | (ml) | (ml) | (ml) | (ml) |
| T01 | ODN1 100 ng | 100 | 4896 | 4 | 5 | 4 | 5 | 9 |
| T02 | ODN1 1000 ng | 100 | 4862 | 38 | 5 | 4 | 5 | 9 |
| T03 | ODN1 5000 ng | 100 | 4712 | 188 | 5 | 4 | 5 | 9 |
| T04 | ODN2 100 ng | 100 | 4896 | 4 | 5 | 4 | 5 | 9 |
| T05 | ODN2 1000 ng | 100 | 4862 | 38 | 5 | 4 | 5 | 9 |
| T06 | ODN2 5000 ng | 100 | 4712 | 188 | 5 | 4 | 5 | 9 |

TABLE 9-continued

Preparation of Test Articles and Control Items

| | | | | | | | | |
|---|---|---|---|---|---|---|---|---|
| T07 | ODN3 100 ng | 100 | 4896 | 4 | 5 | 4 | 5 | 9 |
| T08 | ODN3 1000 ng | 100 | 4862 | 38 | 5 | 4 | 5 | 9 |
| T09 | ODN3 5000 ng | 100 | 4712 | 188 | 5 | 4 | 5 | 9 |
| T10 | Suboptimal vaccine | 100 | 4900 | 0 | 5 | 4 | 5 | 9 |
| T11 | Non diluted vaccine | 5000 | 0 | 0 | 5 | 4 | 5 | 9 |
| T12a | ODN1 5000 ng in Stimune | — | 2887 | 113 | 3 | 2 | 2.5 | 4.5 |
| T12b | ODN2 5000 ng in Stimune | — | 2887 | 113 | 3 | 2 | 2.5 | 4.5 |
| T12c | ODN3 5000 ng in Stimune | — | 2887 | 113 | 3 | 2 | 2.5 | 4.5 |
| T12d | Dilution buffer (PBS) in Stimune | — | 2887 | 113 | 3 | 0.8 | 1 | 1.8 |
| T13 | PolyI:C 10 µg | 100 | 4877 | 23 | 5 | 4 | 5 | 9 |
| T14 | PolyI:C 100 µg | 100 | 4675 | 225 | 5 | 4 | 5 | 9 |

ODN Preparation to 600 ng/µl

| | | 100 µM ODN (µl) | Dilution Buffer (µl) | Volume Stock 600 ng/µl (µl) |
|---|---|---|---|---|
| ODN1 | GCGT3-TG4T-5Chol (SEQ ID NO: 1, see Table 1) | 204 | 196 | 400 |
| ODN2 | GCGT3-TG4T (SEQ ID NO: 252, see Table 1) | 216 | 184 | 400 |
| ODN3 | 2006-PTO (SEQ ID NO: 3, see Table 1) | 312 | 88 | 400 |

Poly I:C 10 µg/µl

| | | Lyophilized Powder (mg) | Physiological Salt Solution (ml) | Volume Stock 10 µg/µl (µl) |
|---|---|---|---|---|
| Control Lot #s: | Poly I:C (P0913) 116M4118V | 10 | 1 #16TK5011 | 1000 10 min 50□, 60 min RT (re-annealing) storage at −20□ |

Chickens allocated to control group of T10 were vaccinated with a suboptimal NDV suspension without immune stimulant in adjuvant (Stimune) at a ratio of 4:5.

Chickens allocated to control group of T11 were vaccinated with a non-diluted NDV suspension without immune stimulant in adjuvant (Stimune) at a ratio of 4:5.

Chickens allocated to group T12 were vaccinated with immune stimulant 1 (3 chickens), immune stimulant 2 (3 chickens) and immune stimulant 3 (3 chickens) in adjuvant (Stimune) at a ratio of 4:5. One chicken was vaccinated with dilution buffer (proprietary) in adjuvant (Stimune).

Chickens allocated to control groups of T13 (n=9) and T14 (n=9) were vaccinated with a suboptimal NDV suspension of NDV in combination with Poly I:C in two concentrations (10,000 ng and 100 µg) in adjuvant (Stimune) at a ratio of 4:5.

Test Article or Control Item Administration

The inactivated NDV strain Ulster suspension stored at −70° C. was thawed and diluted 50 times in negative allantoic fluid to create the suboptimal vaccine dose. Immune stimulants were added according to the study design. The resulting water phases were mixed with Stimune in a ratio of 4:5 according to the vaccination preparation scheme shown in Table 9. During preparation, all vaccine ingredients with the exception of the Stimune adjuvant were placed in melting ice. The formulated vaccines were injected (0.5 ml, intramuscular) directly after preparation.

General health was monitored by an experienced biotechnician daily from day of arrival until the end of the study.

Serum Blood Sampling

Blood samples for serology were collected from all chickens on study days 0 (prior to vaccination), 7, 14 and 21. Blood samples were labelled with the study number, a unique sample identification and the date of collection. Depending on the amount of the drawn blood volume, sera were aliquoted in two aliquots of approximately 0.5 ml and stored at −20±5° C.

Haemagglutination Inhibition (HI) Assay

In brief, dilution series of sera were incubated with 8 HAU (haemagglutinating units) of NDV strain Ulster at room temperature for 60 minutes. The HAU were titrated before each assay. Thereafter, chicken erythrocytes were added and agglutination was scored after incubation at 4° C. for 45 minutes. A negative control serum and three positive control sera, with low, intermediate and high antibody titres were included in each assay.

The HI titre results were expressed as the reciprocal of the highest serum dilution completely inhibiting agglutination, which were logarithmically transformed to the final Log 2 titres.

Statistics

Figure 14:
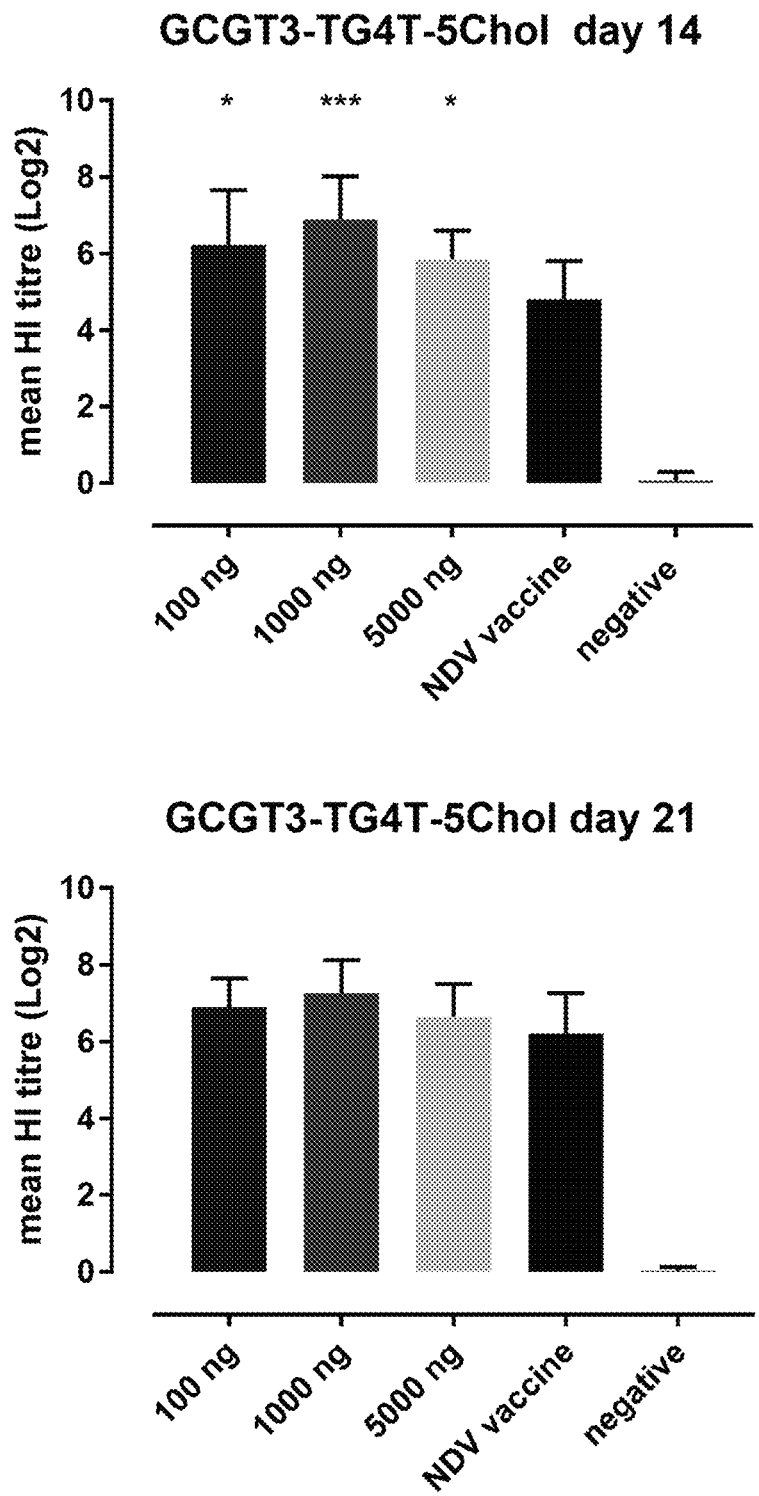
FIG. 14 depicts mean Haemagglutination inhibition (HI) titres (Log 2) (with standard deviation) results for ODN1 (GCGT3-TG4T-5Chol) at days 14 (top panel) and 21 (bottom panel) post vaccination (pv). Asterisks indicate the level of significance (*=significant to ****=highly significant).
Figure 15:
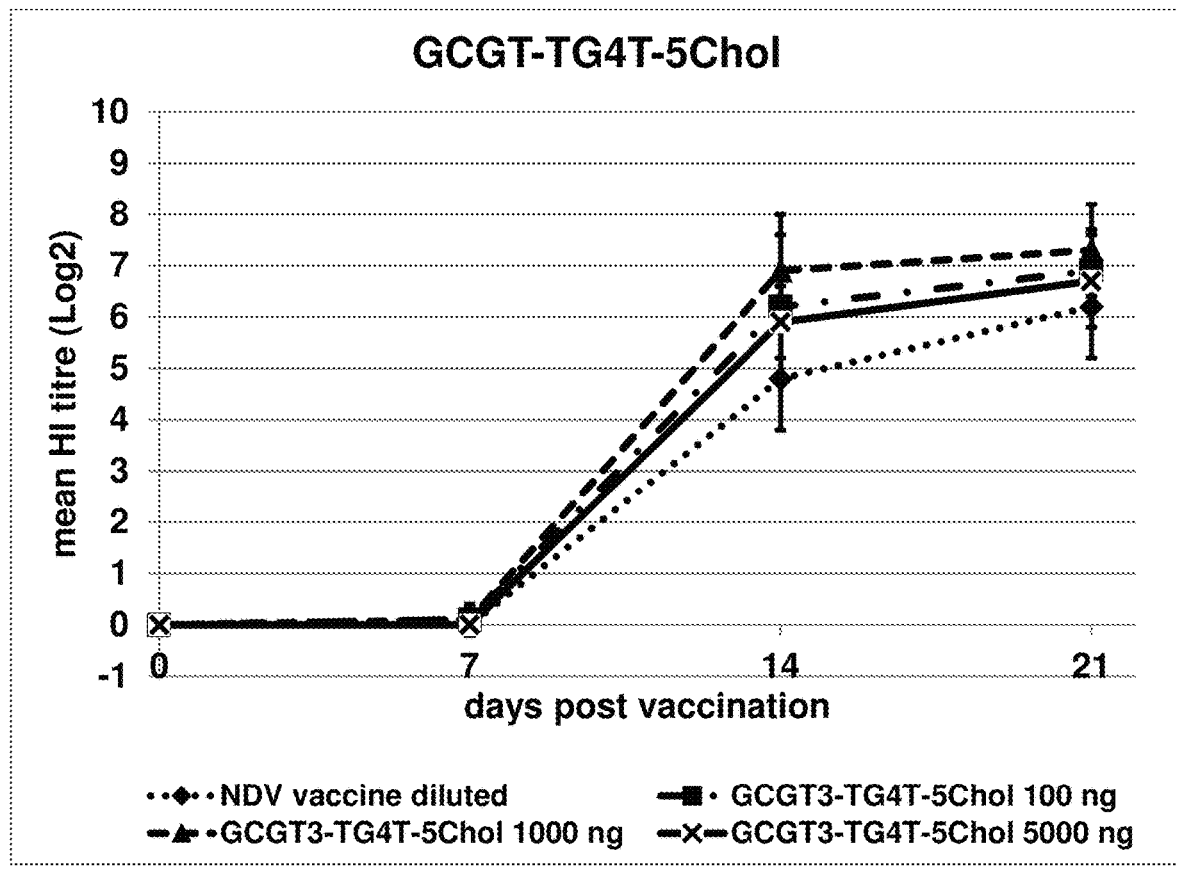
FIG. 15 depicts mean HI titres (Log 2) (with standard deviation) results for ODN1 (GCGT3-TG4T-5Chol) during the entire study.

Logarithmically transformed HI results were summarized per animal (see Tables 62-65). Per treatment group, the mean and standard deviation of the antibody titres were calculated. The statistical analysis was performed with the non-parametric Mann-Whitney t-test.

deviation of these groups are indicated in FIG. 14 (days 14 and 21 post vaccination (pv)) and FIG. 15 (all data) compared to the mean titres of the diluted NDV vaccine group.

The GCGT3-TG4T-5Chol groups showed significantly higher HI titres compared to the diluted NDV vaccine (mean HI titre: 4.8 Log 2/SD 1.0). At day 14 pv this was the case for all three doses; 100 ng: mean HI titre 6.2 Log 2/SD 1.4 (p=0.0214), 1000 ng: mean HI titre 6.9 Log 2/SD 1.1 (p=0.0003) and 5000 ng: mean HI 5.9 Log 2/SD 0.7 (p=0.0243).

At day 21 pv, however, no significant differences were observed for all concentrations; 100 ng: mean HI titre 6.9 Log 2/SD 0.8 (p=0.1995); 1000 ng: mean HI titre 7.3 Log 2/SD 0.9 (p=0.0527); and 5000 ng: mean HI 6.7 Log 2/SD 0.9 (p=0.4523) when comparing to the NDV vaccine; HI titre 6.2 Log 2/SD1.0. (FIG. 14), although the 1000 ng concentration is very close to significance.

TABLE 10

| Results group | duplo HI Treatment | animal | HI 1 d0 | HI 2 d0 | mean | HI 1 d7 | HI 2 d7 | mean | HI 1 d14 | HI 2 d14 | HI 3 d14 | mean | HI 1 d21 | HI 2 d21 | HI 3 d21 | mean |
|---|---|---|---|---|---|---|---|---|---|---|---|---|---|---|---|---|
| T01 | GCGT3-TG4T-5Chol | 11402 | 0 | 0 | 0 | 1 | 1 | 1 | 7 | 7 | 7 | 7.0 | 7 | 7 | 7 | 7.0 |
|  | 100 ng | 11404 | 0 | 0 | 0 | 0 | 0 | 0 | 7 | 7 | 7 | 7.0 | 7 | 7 | 7 | 7.0 |
|  |  | 11406 | 0 | 0 | 0 | 0 | 0 | 0 | 3 | 4 | 4 | 3.7 | 6 | 6 | 6 | 6.0 |
|  |  | 11408 | 0 | 0 | 0 | 0 | 0 | 0 | 7 | 8 | 8 | 7.7 | 8 | 9 | 7 | 8.0 |
|  |  | 11410 | 0 | 0 | 0 | 0 | 0 | 0 | 5 | 6 | 6 | 5.7 | 7 | 7 | 7 | 7.0 |
|  |  | 11412 | 0 | 0 | 0 | 0 | 0 | 0 | 6 | 6 | 8 | 6.7 | 6 | 6 | 6 | 6.0 |
|  |  | 11414 | 0 | 0 | 0 | 0 | 0 | 0 | 5 | 5 | 6 | 5.3 | 7 | 7 | 6 | 6.7 |
|  |  | 11416 | 0 | 0 | 0 | 0 | 0 | 0 | 8 | 7 | 8 | 7.7 | 8 | 8 | 8 | 8.0 |
|  |  | 11418 | 0 | 0 | 0 | 0 | 0 | 0 | 5 | 4 | 4 | 4.3 | 6 | 6 | 6 | 6.0 |
|  |  | 11420 | 0 | 0 | 0 | 0 | 0 | 0 | 8 | 7 | 7 | 7.3 | 7 | 7 | 8 | 7.3 |
|  |  | mean |  |  | 0.0 |  |  | 0.1 |  |  |  | 6.2 |  |  |  | 6.9 |
|  |  | SD |  |  | 0.0 |  |  | 0.3 |  |  |  | 1.4 |  |  |  | 0.8 |
| T02 | GCGT3-TG4T-5Chol | 11422 | 0 | 0 | 0 | 0 | 0 | 0 | 7 | 6 | 7 | 6.7 | 6 | 6 | 6 | 6.0 |
|  | 1000 ng | 11424 | 0 | 0 | 0 | 0 | 0 | 0 | 8 | 7 | 7 | 7.3 | 9 | 7 | 8 | 8.0 |
|  |  | 11426 | 0 | 0 | 0 | 0 | 0 | 0 | 6 | 5 | 5 | 5.3 | 6 | 6 | 6 | 6.0 |
|  |  | 11428 | 0 | 0 | 0 | 0 | 0 | 0 | 7 | 7 | 7 | 7.0 | 7 | 7 | 7 | 7.0 |
|  |  | 11430 | 0 | 0 | 0 | 1 | 1 | 1 | 10 | 9 | 10 | 9.7 | 8 | 8 | 9 | 8.3 |
|  |  | 11432 | 0 | 0 | 0 | 0 | 0 | 0 | 7 | 6 | 7 | 6.7 | 7 | 7 | 7 | 7.0 |
|  |  | 11434 | 0 | 0 | 0 | 0 | 0 | 0 | 7 | 6 | 6 | 6.3 | 7 | 7 | 7 | 7.0 |
|  |  | 11436 | 0 | 0 | 0 | 0 | 0 | 0 | 7 | 6 | 7 | 6.7 | 8 | 7 | 9 | 8.0 |
|  |  | 11438 | 0 | 0 | 0 | 0 | 0 | 0 | 7 | 6 | 6 | 6.3 | 7 | 7 | 7 | 7.0 |
|  |  | 11440 | 0 | 0 | 0 | 0 | 0 | 0 | 7 | 7 | 7 | 7.0 | 8 | 8 | 9 | 8.3 |
|  |  | mean |  |  | 0.0 |  |  | 0.1 |  |  |  | 6.9 |  |  |  | 7.3 |
|  |  | SD |  |  | 0.0 |  |  | 0.3 |  |  |  | 1.1 |  |  |  | 0.9 |
| T03 | GCGT3-TG4T-5Chol | 11442 | 0 | 0 | 0 | 0 | 0 | 0 | 6 | 6 | 7 | 6.3 | 7 | 7 | 8 | 7.3 |
|  | 5000 ng | 11444 | 0 | 0 | 0 | 0 | 0 | 0 | 5 | 5 | 5 | 5.0 | 6 | 6 | 6 | 6.0 |
|  |  | 11446 | 0 | 0 | 0 | 0 | 0 | 0 | 5 | 4 | 5 | 4.7 | 5 | 5 | 6 | 5.3 |
|  |  | 11448 | 0 | 0 | 0 | 0 | 0 | 0 | 7 | 7 | 7 | 7.0 | 8 | 8 | 9 | 8.3 |
|  |  | 11450 | 0 | 0 | 0 | 0 | 0 | 0 | 6 | 5 | 5 | 5.3 | 6 | 6 | 7 | 6.3 |
|  |  | 11452 | 0 | 0 | 0 | 0 | 0 | 0 | 6 | 5 | 6 | 5.7 | 7 | 7 | 7 | 7.0 |
|  |  | 11454 | 0 | 0 | 0 | 0 | 0 | 0 | 7 | 6 | 6 | 6.3 | 7 | 6 | 7 | 6.7 |
|  |  | 11456 | 0 | 0 | 0 | 0 | 0 | 0 | 6 | 6 | 6 | 6.0 | 6 | 6 | 6 | 6.0 |
|  |  | 11458 | 0 | 0 | 0 | 0 | 0 | 0 | 6 | 5 | 6 | 5.7 | 6 | 6 | 7 | 6.3 |
|  |  | 11460 | 0 | 0 | 0 | 0 | 0 | 0 | 7 | 6 | 7 | 6.7 | 7 | 7 | 8 | 7.3 |
|  |  | mean |  |  | 0.0 |  |  | 0.0 |  |  |  | 5.9 |  |  |  | 6.7 |
|  |  | SD |  |  | 0.0 |  |  | 0.0 |  |  |  | 0.7 |  |  |  | 0.9 |

Results

No clinical symptoms or adverse events related to the vaccination were observed in all groups, all chickens appeared healthy during the entire study period.

Two chickens, however were scored with minor injuries due to pecking behaviour, which started 6 days before the start of the study. On the day of vaccination these chickens were allocated to the Poly I:C groups T13 (#11658) and T14 (#11676). Recovery took place within one week after vaccination.

ODN1, GCGT3-TG4T-5Chol

The individual HI results expressed as Log 2 titres of the 100 ng, 1000 ng and 5000 ng ODN1 dose groups are indicated in Table 10. The mean HI titres and standard

ODN2, GCGT3-TG4T

Figure 16:
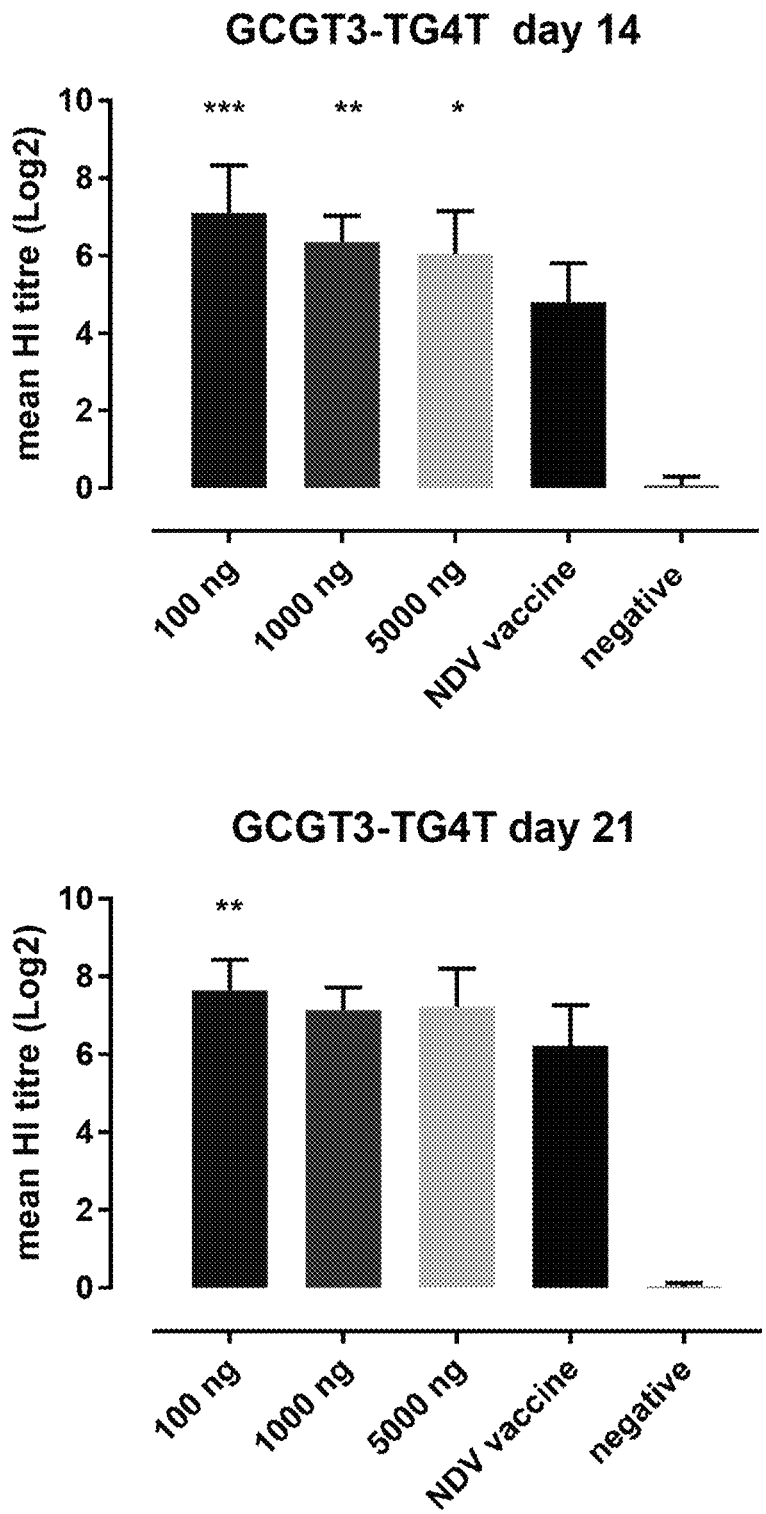
FIG. 16 depicts mean HI titres (Log 2) (with standard deviation) results for ODN2 (GCGT3-TG4T) at days 14 (top panel) and 21 (bottom panel) post vaccination. Asterisks indicate the level of significance (*=significant to ****=highly significant).
Figure 17:
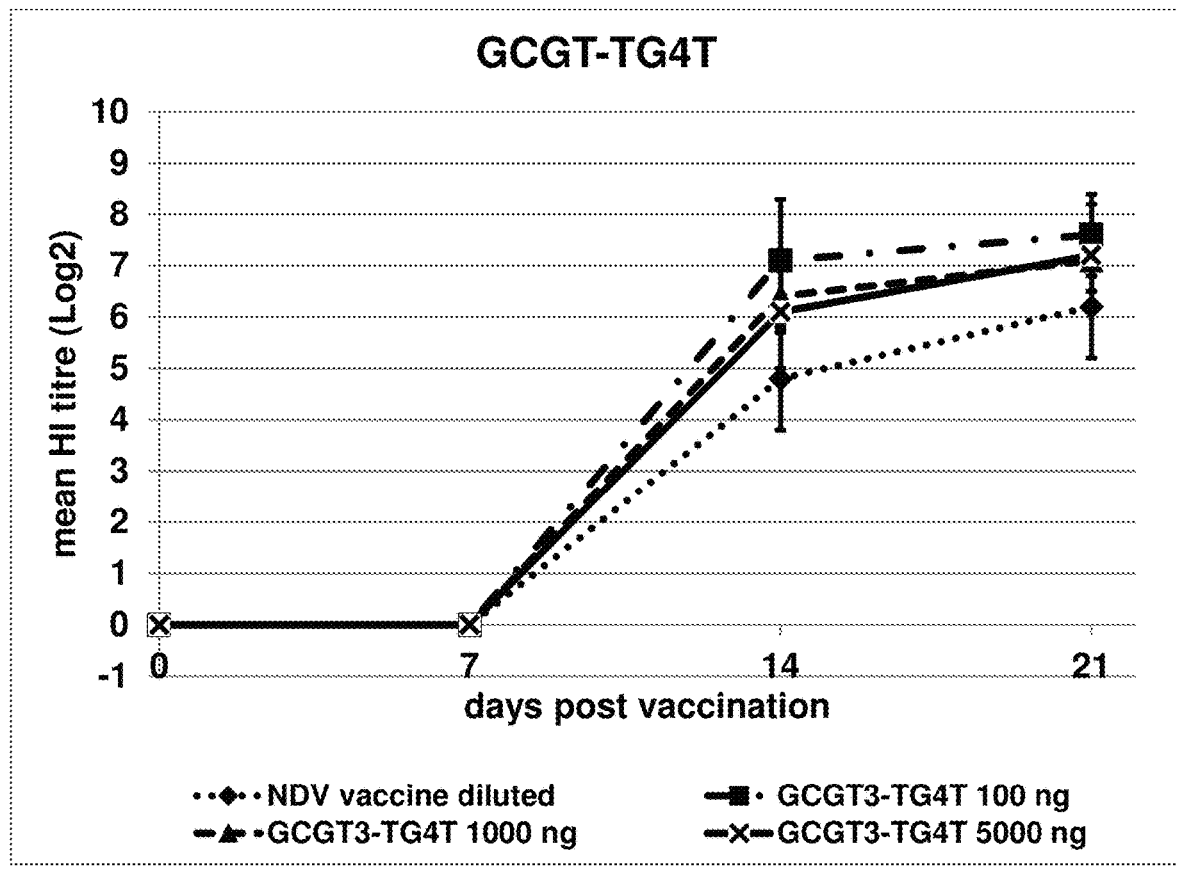
FIG. 17 depicts mean HI titres (Log 2) (with standard deviation) results for ODN2 (GCGT3-TG4T) during the entire study.

The individual HI results expressed as Log 2 titres of the 100 ng, 1000 ng and 5000 ng ODN1 dose groups are indicated in Table 11. The mean HI titres and standard deviation of these groups are indicated in FIG. 16 (days 14 and 21 pv) and FIG. 17 (all data) compared to the mean titres of the diluted NDV vaccine group.

The ODN2, GCGT3-TG4T groups showed significantly higher HI titres compared to the diluted NDV vaccine (mean HI titre: 4.8 Log 2/SD 1.0). This was the case at day 14 post vaccination for all three doses; 100 ng: mean HI titre 7.1 Log 2/SD 1.2 (p=0.0003), 1000 ng: mean HI titre 6.4 Log 2/SD 0.7 (p=0.0027) and 5000 ng: mean HI titre 6.1 Log 2/SD 1.1

(p=0.0236). At day 21 significant differences were only observed at the 100 ng dose with a mean HI titre of 7.6 Log 2/SD 0.8 (p=0.0083) when compared to the NDV vaccine (HI titre 6.2 Log 2/SD 1.0). The mean HI titres for the 1000 ng and 5000 ng were 7.1 Log$_2$/0.6 (p=0.0696) and 7.2 Log 2/SD 1.0 (p=0.0956) respectively (FIG. 16).

TABLE 11

| | | | | | | | | | | | | | | | | | | |
|---|---|---|---|---|---|---|---|---|---|---|---|---|---|---|---|---|---|---|
| T04 | GCGT3-TG4T | 11462 | 0 | 0 | 0 | 0 | 0 | 0 | 7 | 6 | 7 | 6.7 | 7 | 7 | 7 | 7.3 | | |
| | 100 ng | 11464 | 0 | 0 | 0 | 0 | 0 | 0 | 8 | 7 | 8 | 7.7 | 7 | 8 | 8 | 7.7 | | |
| | | 11466 | 0 | 0 | 0 | 0 | 0 | 0 | 7 | 6 | 6 | 6.3 | 8 | 8 | 7 | 7.7 | | |
| | | 11468 | 0 | 0 | 0 | 0 | 0 | 0 | 8 | 7 | 8 | 7.7 | 8 | 9 | 8 | 8.3 | | |
| | | 11710 | 0 | 0 | 0 | 0 | 0 | 0 | 7 | 6 | 7 | 6.7 | 7 | 7 | 7 | 7.0 | | |
| | | 11472 | 0 | 0 | 0 | 0 | 0 | 0 | 10 | 10 | 9 | 9.7 | 10 | 9 | 8 | 9.0 | | |
| | | 11474 | 0 | 0 | 0 | 0 | 0 | 0 | 7 | 6 | 6 | 6.3 | 7 | 7 | 7 | 7.0 | | |
| | | 11476 | 0 | 0 | 0 | 0 | 0 | 0 | 6 | 5 | 5 | 5.3 | 7 | 7 | 6 | 6.7 | | |
| | | 11478 | 0 | 0 | 0 | 0 | 0 | 0 | 8 | 6 | 6 | 6.7 | 7 | 7 | 7 | 7.0 | | |
| | | 11480 | 0 | 0 | 0 | 0 | 0 | 0 | 9 | 8 | 7 | 8.0 | 9 | 9 | 8 | 8.7 | | |
| | | mean | | | 0.0 | | | 0.0 | | | | 7.1 | | | | 7.6 | | |
| | | SD | | | 0.0 | | | 0.0 | | | | 1.2 | | | | 0.8 | | |
| T05 | GCGT3-TG4T | 11482 | 0 | 0 | 0 | 0 | 0 | 0 | 6 | 6 | 6 | 6.0 | 7 | 7 | 7 | 7.0 | | |
| | 1000 ng | 11484 | 0 | 0 | 0 | 0 | 0 | 0 | 6 | 6 | 7 | 6.3 | 7 | 7 | 7 | 7.0 | | |
| | | 11486 | 0 | 0 | 0 | 0 | 0 | 0 | 6 | 6 | 6 | 6.0 | 7 | 7 | 7 | 7.0 | | |
| | | 11488 | 0 | 0 | 0 | 0 | 0 | 0 | 6 | 8 | 6 | 6.7 | 8 | 8 | 8 | 8.0 | | |
| | | 11490 | 0 | 0 | 0 | 0 | 0 | 0 | 5 | 5 | 5 | 5.0 | 6 | 6 | 6 | 6.0 | | |
| | | 11492 | 0 | 0 | 0 | 0 | 0 | 0 | 7 | 7 | 7 | 7.0 | 7 | 7 | 8 | 7.3 | | |
| | | 11494 | 0 | 0 | 0 | 0 | 0 | 0 | 7 | 7 | 7 | 7.0 | 7 | 7 | 7 | 7.0 | | |
| | | 11496 | 0 | 0 | 0 | 0 | 0 | 0 | 6 | 6 | 6 | 6.0 | 7 | 8 | 7 | 7.3 | | |
| | | 11498 | 0 | 0 | 0 | 0 | 0 | 0 | 8 | 7 | 7 | 7.3 | 9 | 7 | 8 | 8.0 | | |
| | | 11500 | 0 | 0 | 0 | 0 | 0 | 0 | 7 | 6 | 6 | 6.3 | 7 | 6 | 7 | 6.7 | | |
| | | mean | | | 0.0 | | | 0.0 | | | | 6.4 | | | | 7.1 | | |
| | | SD | | | 0.0 | | | 0.0 | | | | 0.7 | | | | 0.6 | | |
| T06 | GCGT3-TG4T | 11502 | 0 | 0 | 0 | 0 | 0 | 0 | 8 | 7 | 7 | 7.3 | 10 | 8 | 9 | 9.0 | | |
| | 5000 ng | 11504 | 0 | 0 | 0 | 0 | 0 | 0 | 7 | 7 | 6 | 6.7 | 8 | 7 | 7 | 7.3 | | |
| | | 11506 | 0 | 0 | 0 | 0 | 0 | 0 | 7 | 6 | 6 | 6.3 | 7 | 6 | 7 | 6.7 | | |
| | | 11508 | 0 | 0 | 0 | 0 | 0 | 0 | 6 | 5 | 5 | 5.3 | 8 | 6 | 7 | 7.0 | | |
| | | 11510 | 0 | 0 | 0 | 0 | 0 | 0 | 8 | 7 | 7 | 7.3 | 9 | 8 | 8 | 8.3 | | |
| | | 11512 | 0 | 0 | 0 | 0 | 0 | 0 | 8 | 6 | 7 | 7.0 | 9 | 7 | 8 | 8.0 | | |
| | | 11514 | 0 | 0 | 0 | 0 | 0 | 0 | 5 | 5 | 5 | 5.0 | 6 | 6 | 7 | 6.3 | | |
| | | 11516 | 0 | 0 | 0 | 0 | 0 | 0 | 7 | 6 | 6 | 6.3 | 7 | 7 | 7 | 7.0 | | |
| | | 11518 | 0 | 0 | 0 | 0 | 0 | 0 | 6 | 5 | 5 | 5.3 | 7 | 6 | 8 | 7.0 | | |
| | | 11520 | 0 | 0 | 0 | 0 | 0 | 0 | 4 | 4 | 4 | 4.0 | 6 | 5 | 6 | 5.7 | | |
| | | mean | | | 0.0 | | | 0.0 | | | | 6.1 | | | | 7.2 | | |
| | | SD | | | 0.0 | | | 0.0 | | | | 1.1 | | | | 1.0 | | |

ODN3, 2006-PTO

The individual HI results expressed as Log 2 titres of the 100 ng, 1000 ng and 5000 ng ODN1 dose groups measured are indicated in Table 12. During the triplicate HI assay performance on day 21, an outlier result was observed for animal 11570 on day 21, this was most likely caused by a pipetting error (not enough AF added) and therefore this result was omitted from the final analysis (highlighted in Table 12). Thus, for this animal and date the mean HI titre was based on the duplicate measurement.

Figure 18:
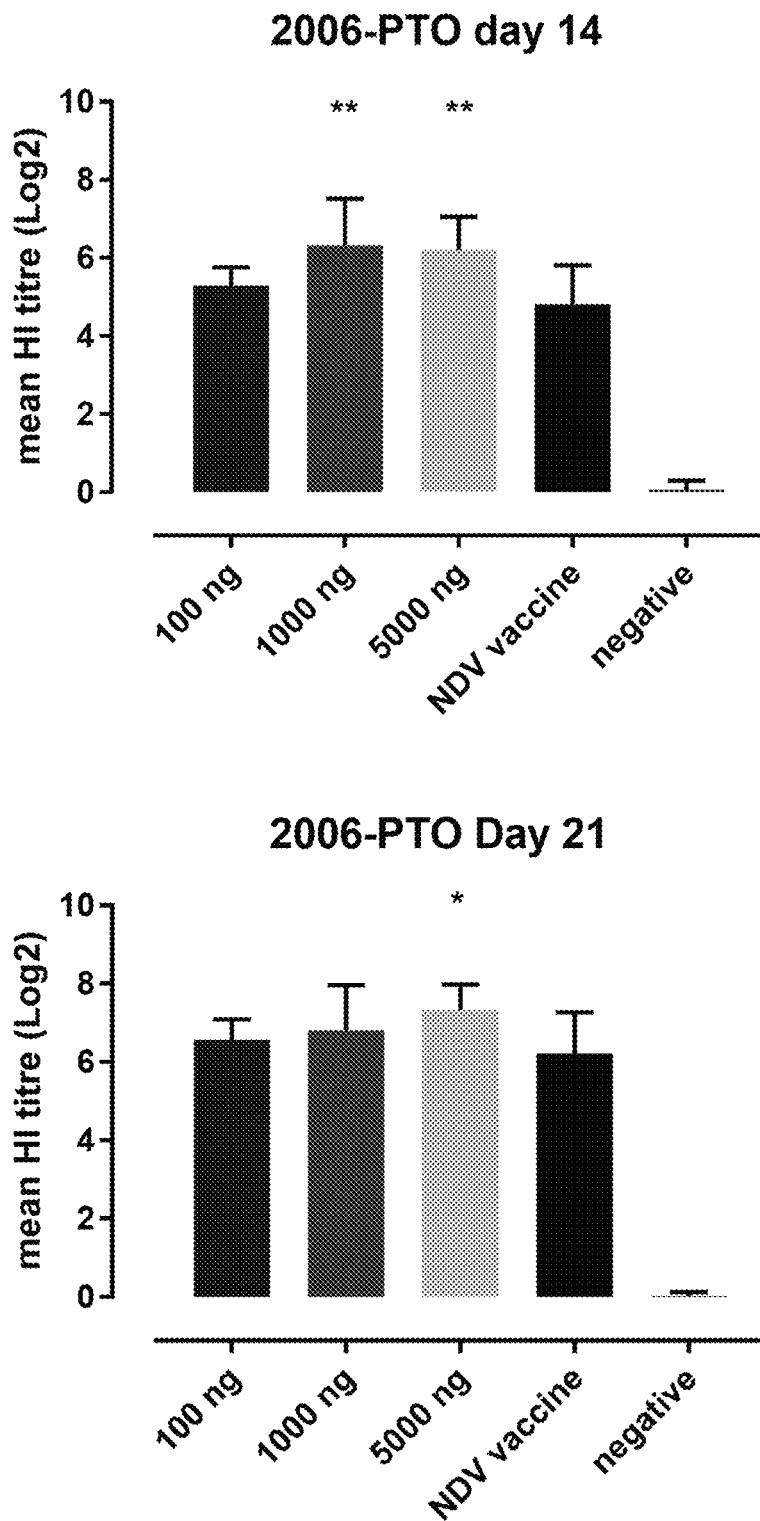
FIG. 18 depicts mean HI titres (Log 2) (with standard deviation) results for ODN3 (2006-PTO) at days 14 (top panel) and 21 (bottom panel) post vaccination. Asterisks indicate the level of significance (*=significant to ****=highly significant).
Figure 19:
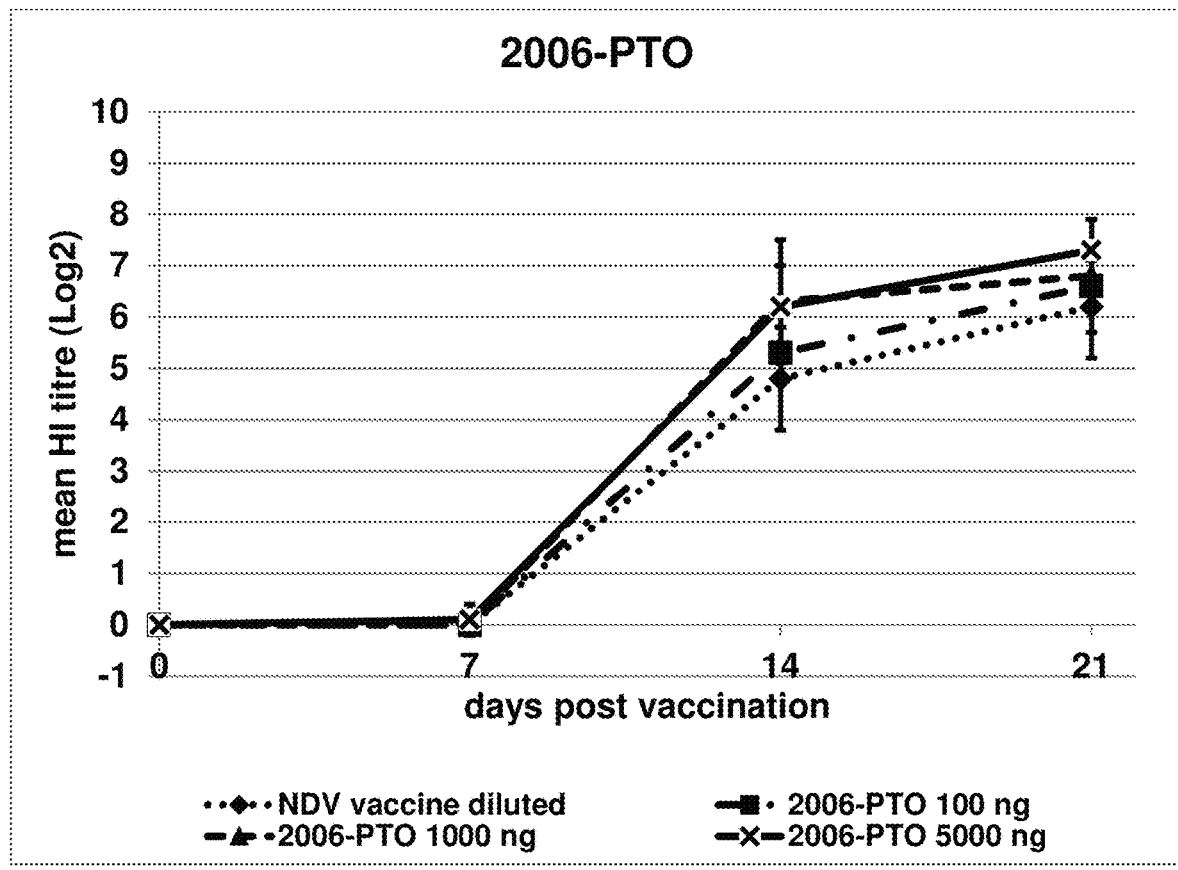
FIG. 19 depicts mean HI titres (Log 2) (with standard deviation) results for ODN3 (2006-PTO) during the entire study.

The mean HI titres and standard deviation of these groups are indicated in FIG. 18 (days 14 and 21 pv) and FIG. 19 (all data) compared to the mean titres of the diluted NDV vaccine group.

The ODN3, 2006-PTO groups showed significantly higher HI titres compared to the diluted NDV vaccine (mean HI titre: 4.8 Log 2/SD 1.0). This was the case at day 14 post vaccination for two doses; 1000 ng: mean HI titre: 6.3 Log 2/SD 1.2 (p=0.0081) and 5000 ng: mean HI titre: 6.2 Log 2/SD 0.8 (p=0.0059). The mean HI titre of the 100 ng dose was 5.3 Log 2/SD 0.5 (p=0.2090). At day 21 pv significant differences were only measured at the 5000 ng: mean HI titre 7.3 Log 2/SD 0.6 (p=0.0296). No significant differences were observed at the 100 ng and 1000 ng doses, with mean HI titres of 6.6 Log 2/SD 0.5 (p=0.7183) and 6.8 Log 2/SD 1.1 (p=0.1685) respectively, when comparing to the NDV vaccine; HI titre 6.2 Log 2/SD 1.0 (FIG. 18).

TABLE 12

| | | | | | | | | | | | | | | | | | |
|---|---|---|---|---|---|---|---|---|---|---|---|---|---|---|---|---|---|
| T07 | 2006-PTO | 11522 | 0 | 0 | 0 | 0 | 0 | 0 | 6 | 5 | 5 | 5.3 | 6 | 6 | 6 | 6.0 |
| | 100 ng | 11524 | 0 | 0 | 0 | 0 | 0 | 0 | 5 | 5 | 6 | 5.3 | 6 | 6 | 6 | 6.0 |
| | | 11526 | 0 | 0 | 0 | 0 | 0 | 0 | 6 | 5 | 6 | 5.7 | 7 | 7 | 7 | 7.0 |
| | | 11528 | 0 | 0 | 0 | 0 | 0 | 0 | 5 | 5 | 5 | 5.0 | 6 | 7 | 6 | 6.3 |
| | | 11530 | 0 | 0 | 0 | 0 | 0 | 0 | 6 | 5 | 7 | 6.0 | 7 | 7 | 7 | 7.0 |
| | | 11532 | 0 | 0 | 0 | 0 | 0 | 0 | 5 | 5 | 5 | 5.0 | 5 | 6 | 6 | 5.7 |
| | | 11534 | 0 | 0 | 0 | 0 | 0 | 0 | 5 | 5 | 6 | 5.3 | 7 | 7 | 7 | 7.0 |
| | | 11536 | 0 | 0 | 0 | 0 | 0 | 0 | 5 | 5 | 6 | 5.3 | 7 | 7 | 7 | 7.0 |
| | | 11538 | 0 | 0 | 0 | 0 | 0 | 0 | 4 | 4 | 5 | 4.3 | 7 | 6 | 7 | 6.7 |
| | | 11540 | 0 | 0 | 0 | 0 | 0 | 0 | 6 | 5 | 6 | 5.7 | 7 | 7 | 7 | 7.0 |
| | | mean | | | 0.0 | | | 0.0 | | | | 5.3 | | | | 6.6 |
| | | SD | | | 0.0 | | | 0.0 | | | | 0.5 | | | | 0.5 |

TABLE 12-continued

| | | | | | | | | | | | | | | | | | |
|---|---|---|---|---|---|---|---|---|---|---|---|---|---|---|---|---|---|
| T08 | 2006-PTO | 11542 | 0 | 0 | 0 | 0 | 0 | 0 | 6 | 5 | 6 | 5.7 | 6 | 6 | 7 | 6.3 |
| | 1000 ng | 11544 | 0 | 0 | 0 | 0 | 0 | 0 | 6 | 4 | 6 | 5.3 | 7 | 7 | 7 | 7.0 |
| | | 11546 | 0 | 0 | 0 | 0 | 0 | 0 | 4 | 4 | 5 | 4.3 | 4 | 5 | 4 | 4.3 |
| | | 11548 | 0 | 0 | 0 | 0 | 0 | 0 | 5 | 5 | 6 | 5.3 | 6 | 6 | 7 | 6.3 |
| | | 11550 | 0 | 0 | 0 | 0 | 0 | 0 | 7 | 7 | 7 | 7.0 | 7 | 7 | 8 | 7.3 |
| | | 11552 | 0 | 0 | 0 | 0 | 0 | 0 | 7 | 7 | 8 | 7.3 | 7 | 7 | 8 | 7.3 |
| | | 11554 | 0 | 0 | 0 | 0 | 0 | 0 | 8 | 8 | 9 | 8.3 | 8 | 8 | 9 | 8.3 |
| | | 11556 | 0 | 0 | 0 | 0 | 0 | 0 | 6 | 6 | 6 | 6.0 | 6 | 6 | 6 | 6.0 |
| | | 11558 | 0 | 0 | 0 | 0 | 0 | 0 | 7 | 7 | 7 | 7.0 | 7 | 7 | 8 | 7.3 |
| | | 11560 | 0 | 0 | 0 | 0 | 0 | 0 | 7 | 7 | 7 | 7.0 | 8 | 8 | 8 | 8.0 |
| | | mean | | | 0.0 | | | 0.0 | | | | 6.3 | | | | 6.8 |
| | | SD | | | 0.0 | | | 0.0 | | | | 1.2 | | | | 1.1 |
| T09 | 2006-PTO | 11562 | 0 | 0 | 0 | 0 | 0 | 0 | 6 | 6 | 6 | 6.0 | 7 | 7 | 8 | 7.3 |
| | 5000 ng | 11564 | 0 | 0 | 0 | 0 | 0 | 0 | 6 | 6 | 7 | 6.3 | 7 | 7 | 8 | 7.3 |
| | | 11566 | 0 | 0 | 0 | 0 | 0 | 0 | 6 | 6 | 7 | 6.3 | 7 | 7 | 7 | 7.0 |
| | | 11568 | 0 | 0 | 0 | 0 | 0 | 0 | 6 | 6 | 7 | 6.3 | 7 | 7 | 7 | 7.0 |
| | | 11570 | 0 | 0 | 0 | 0 | 0 | 0 | 5 | 5 | 6 | 5.3 | 7 | 11 | 7 | 7.0 |
| | | 11572 | 0 | 0 | 0 | 0 | 0 | 0 | 6 | 6 | 7 | 6.3 | 7 | 8 | 8 | 7.7 |
| | | 11574 | 0 | 0 | 0 | 0 | 0 | 0 | 5 | 5 | 6 | 5.3 | 6 | 7 | 7 | 6.7 |
| | | 11576 | 0 | 0 | 0 | 0 | 0 | 0 | 8 | 8 | 9 | 8.3 | 8 | 10 | 9 | 9.0 |
| | | 11578 | 0 | 0 | 0 | 0 | 0 | 0 | 6 | 6 | 7 | 6.3 | 7 | 7 | 7 | 7.0 |
| | | 11580 | 0 | 0 | 0 | 1 | 1 | 1 | 5 | 5 | 7 | 5.7 | 7 | 7 | 8 | 7.3 |
| | | mean | | | 0.0 | | | 0.1 | | | | 6.2 | | | | 7.3 |
| | | SD | | | 0.0 | | | 0.3 | | | | 0.8 | | | | 0.6 |

Control Groups

Figure 20:
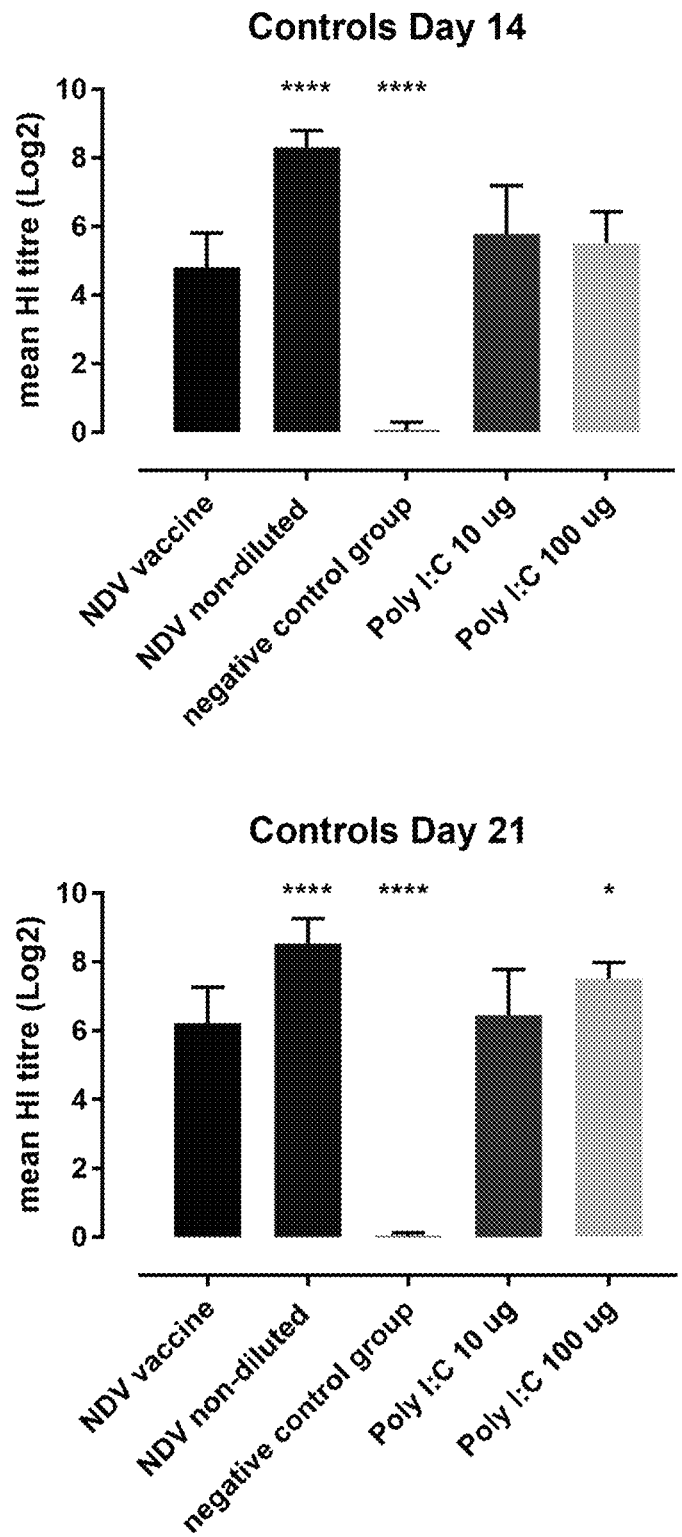
FIG. 20 depicts mean HI titres (Log 2) (with standard deviation) results for positive and negative control Test Articles at days 14 (top panel) and 21 (bottom panel) post vaccination. Asterisks indicate the level of significance (*=significant to ****=highly significant).
Figure 21:
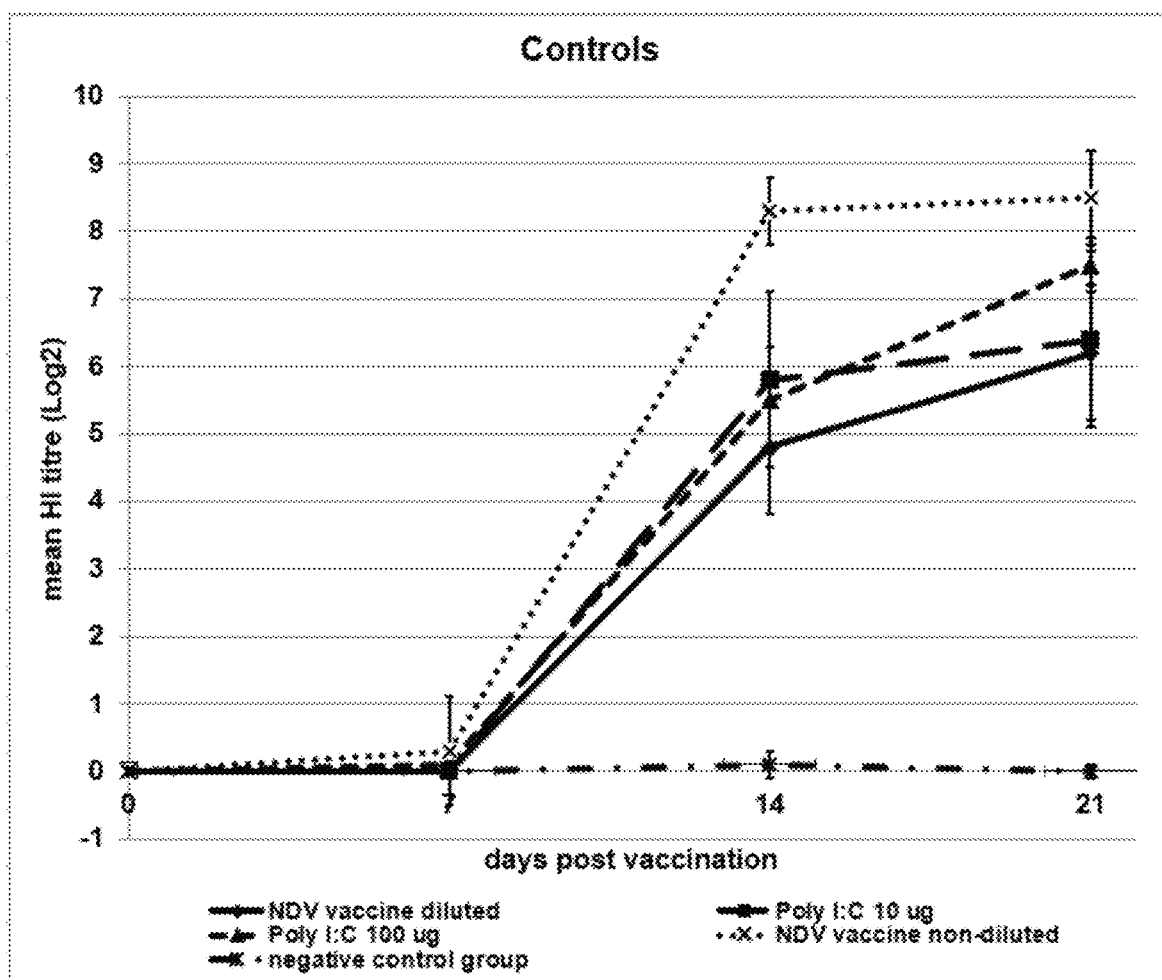
FIG. 21 depicts mean HI titres (Log 2) (with standard deviation) results for positive and negative control Test Articles during the entire study.

The individual HI results expressed as Log 2 titres of the 10 μg and 100 μg Poly I:C dose groups, the diluted and non-diluted NDV vaccines and the negative control groups are indicated in Table 13. The mean HI titres and standard deviation of these groups are indicated in FIG. 20 (days 14 and 21 pv) and FIG. 21 (all data) compared to the mean titres of the diluted NDV vaccine group.

For Poly I:C, the positive control groups, significantly higher HI titres were only observed at the 100 μg dose: HI titre 7.5 Log 2/SD 0.4 at day 21 (p=0.0053) when compared with the NDV vaccine (6.2 Log 2/SD 1.0). The mean HI titres at day 14 pv of the 10 μg and 100 μg dose groups were 5.8 Log 2/SD 1.3 (p=0.1859) and 5.5 Log 2/SD 0.8 (p=0.1609) respectively. The mean HI titre of the 10 μg dose group at day 21 pv was 6.4 Log 2/SD 1.3 (p=0.7273). Significant differences (p<0.0001) were observed between the non-diluted NDV vaccine (8.3/SD 0.5 and 8.5 Log 2/SD 0.7) and the negative control group compared to the diluted NDV group at days 14 and 21 post vaccination (4.8/SD 1.0 and 6.2 Log 2/SD 1.0, respectively) (FIG. 20).

TABLE 13

| | | | | | | | | | | | | | | | | | |
|---|---|---|---|---|---|---|---|---|---|---|---|---|---|---|---|---|---|
| T10 | Suboptimal vaccine | 11582 | 0 | 0 | 0 | 0 | 0 | 0 | 4 | 4 | 4 | 4.0 | 6 | 5 | 6 | 5.7 |
| | (1:50) | 11584 | 0 | 0 | 0 | 0 | 0 | 0 | 5 | 6 | 5 | 5.3 | 7 | 7 | 7 | 7.0 |
| | | 11586 | 0 | 0 | 0 | 0 | 0 | 0 | 5 | 5 | 6 | 5.3 | 5 | 5 | 6 | 5.3 |
| | | 11588 | 0 | 0 | 0 | 0 | 0 | 0 | 6 | 6 | 7 | 6.3 | 7 | 6 | 8 | 7.0 |
| | | 11590 | 0 | 0 | 0 | 0 | 0 | 0 | 4 | 4 | 5 | 4.3 | 6 | 6 | 6 | 6.0 |
| | | 11592 | 0 | 0 | 0 | 0 | 0 | 0 | 5 | 5 | 5 | 5.0 | 7 | 7 | 8 | 7.3 |
| | | 11594 | 0 | 0 | 0 | 0 | 0 | 0 | 4 | 4 | 5 | 4.3 | 6 | 7 | 8 | 7.0 |
| | | 11596 | 0 | 0 | 0 | 0 | 0 | 0 | 6 | 6 | 7 | 6.3 | 7 | 7 | 8 | 7.3 |
| | | 11598 | 0 | 0 | 0 | 0 | 0 | 0 | 4 | 4 | 4 | 4.0 | 4 | 4 | 5 | 4.3 |
| | | 11600 | 0 | 0 | 0 | 0 | 0 | 0 | 3 | 3 | 4 | 3.3 | 5 | 5 | 6 | 5.3 |
| | | mean | | | 0.0 | | | 0.0 | | | | 4.8 | | | | 6.2 |
| | | SD | | | 0.0 | | | 0.0 | | | | 1.0 | | | | 1.0 |
| T11 | Non diluted vaccine | 11602 | 0 | 0 | 0 | 0 | 0 | 0 | 8 | 8 | 8 | 8.0 | 9 | 9 | 10 | 9.3 |
| | | 11604 | 0 | 0 | 0 | 0 | 0 | 0 | 9 | 9 | 8 | 8.7 | 8 | 9 | 10 | 9.0 |
| | | 11606 | 0 | 0 | 0 | 0 | 0 | 0 | 7 | 7 | 8 | 7.3 | 8 | 8 | 9 | 8.3 |
| | | 11608 | 0 | 0 | 0 | 0 | 0 | 0 | 8 | 9 | 9 | 8.7 | 9 | 9 | 10 | 9.3 |
| | | 11610 | 0 | 0 | 0 | 0 | 0 | 0 | 9 | 9 | 9 | 9.0 | 10 | 9 | 10 | 9.7 |
| | | 11612 | 0 | 0 | 0 | 0 | 0 | 0 | 8 | 8 | 9 | 8.3 | 8 | 8 | 8 | 8.0 |
| | | 11614 | 0 | 0 | 0 | 0 | 0 | 0 | 9 | 8 | 9 | 8.7 | 8 | 7 | 8 | 7.7 |
| | | 11616 | 0 | 0 | 0 | 0 | 0 | 0 | 8 | 8 | 8 | 8.0 | 7 | 8 | 8 | 7.7 |
| | | 11618 | 0 | 0 | 0 | 2 | 3 | 2.5 | 9 | 8 | 8 | 8.3 | 8 | 8 | 9 | 8.3 |
| | | 11620 | 0 | 0 | 0 | 0 | 0 | 0 | 8 | 8 | 8 | 8.0 | 8 | 8 | 8 | 8.0 |
| | | mean | | | 0.0 | | | 0.3 | | | | 8.3 | | | | 8.5 |
| | | SD | | | 0.0 | | | 0.8 | | | | 0.5 | | | | 0.7 |
| T12 | negative controles | 11622 | 0 | 0 | 0 | 0 | 0 | 0 | 0 | 1 | 1 | 0.7 | 0 | 0 | 1 | 0.3 |
| | | 11624 | 0 | 0 | 0 | 0 | 0 | 0 | 0 | 0 | 0 | 0.0 | 0 | 0 | 0 | 0.0 |
| | | 11626 | 0 | 0 | 0 | 0 | 0 | 0 | 0 | 0 | 0 | 0.0 | 0 | 0 | 0 | 0.0 |
| | | 11628 | 0 | 0 | 0 | 0 | 0 | 0 | 0 | 0 | 0 | 0.0 | 0 | 0 | 0 | 0.0 |
| | | 11630 | 0 | 0 | 0 | 0 | 0 | 0 | 0 | 0 | 0 | 0.0 | 0 | 0 | 0 | 0.0 |
| | | 11632 | 0 | 0 | 0 | 0 | 0 | 0 | 0 | 0 | 0 | 0.0 | 0 | 0 | 0 | 0.0 |
| | | 11634 | 0 | 0 | 0 | 0 | 0 | 0 | 0 | 0 | 0 | 0.0 | 0 | 0 | 0 | 0.0 |
| | | 11636 | 0 | 0 | 0 | 0 | 0 | 0 | 0 | 0 | 0 | 0.0 | 0 | 0 | 0 | 0.0 |
| | | 11638 | 0 | 0 | 0 | 0 | 0 | 0 | 0 | 0 | 0 | 0.0 | 0 | 0 | 0 | 0.0 |
| | | 11640 | 0 | 0 | 0 | 0 | 0 | 0 | 0 | 0 | 0 | 0.0 | 0 | 0 | 0 | 0.0 |
| | | mean | | | 0.0 | | | 0.0 | | | | 0.1 | | | | 0.0 |
| | | SD | | | 0.0 | | | 0.0 | | | | 0.2 | | | | 0.1 |

TABLE 13-continued

| | | | | | | | | | | | | | | | | | |
|---|---|---|---|---|---|---|---|---|---|---|---|---|---|---|---|---|---|
| T13 | Poly I:C 10 µg | 11642 | 0 | 0 | 0 | 0 | 0 | 0 | 4 | 4 | 4 | 4.0 | 4 | 4 | 4 | 4.0 |
| | | 11644 | 0 | 0 | 0 | 0 | 0 | 0 | 6 | 6 | 6 | 6.0 | 7 | 7 | 7 | 7.0 |
| | | 11646 | 0 | 0 | 0 | 0 | 0 | 0 | 7 | 7 | 8 | 7.3 | 8 | 8 | 8 | 8.0 |
| | | 11648 | 0 | 0 | 0 | 0 | 0 | 0 | 5 | 4 | 5 | 4.7 | 6 | 6 | 6 | 6.0 |
| | | 11650 | 0 | 0 | 0 | 0 | 0 | 0 | 5 | 5 | 5 | 5.0 | 6 | 6 | 6 | 6.0 |
| | | 11652 | 0 | 0 | 0 | 0 | 0 | 0 | 7 | 7 | 7 | 7.0 | 7 | 7 | 7 | 7.0 |
| | | 11654 | 0 | 0 | 0 | 0 | 0 | 0 | 6 | 6 | 7 | 6.3 | 7 | 7 | 7 | 7.0 |
| | | 11656 | 0 | 0 | 0 | 0 | 0 | 0 | 4 | 4 | 4 | 4.0 | 5 | 5 | 5 | 5.0 |
| | | 11658 | 0 | 0 | 0 | 0 | 0 | 0 | 8 | 7 | 8 | 7.7 | 8 | 8 | 8 | 8.0 |
| | | mean | | | 0.0 | | | 0.1 | | | | 5.8 | | | | 6.4 |
| | | SD | | | 0.0 | | | 0.2 | | | | 1.3 | | | | 1.3 |
| T14 | Poly I:C 100 µg | 11660 | 0 | 0 | 0 | 0 | 0 | 0 | 4 | 4 | 4 | 4.0 | 7 | 7 | 7 | 7.0 |
| | | 11662 | 0 | 0 | 0 | 0 | 0 | 0 | 4 | 4 | 5 | 4.3 | 7 | 7 | 7 | 7.0 |
| | | 11664 | 0 | 0 | 0 | 0 | 0 | 0 | 5 | 5 | 5 | 5.0 | 7 | 7 | 7 | 7.0 |
| | | 11666 | 0 | 0 | 0 | 0 | 0 | 0 | 6 | 6 | 6 | 6.0 | 7 | 7 | 8 | 7.3 |
| | | 11668 | 0 | 0 | 0 | 0 | 0 | 0 | 6 | 6 | 7 | 6.3 | 8 | 8 | 8 | 8.0 |
| | | 11670 | 0 | 0 | 0 | 0 | 0 | 0 | 6 | 6 | 6 | 6.0 | 7 | 8 | 8 | 7.3 |
| | | 11672 | 0 | 0 | 0 | 0 | 0 | 0 | 6 | 6 | 5 | 5.7 | 7 | 8 | 9 | 8.0 |
| | | 11674 | 0 | 0 | 0 | 0 | 0 | 0 | 6 | 6 | 5 | 5.7 | 8 | 8 | 8 | 8.0 |
| | | 11676 | 0 | 0 | 0 | 1 | 0 | 0.5 | 7 | 7 | 6 | 6.7 | 8 | 8 | 8 | 8.0 |
| | | mean | | | 0.0 | | | 0.1 | | | | 5.5 | | | | 7.5 |
| | | SD | | | 0.0 | | | 0.2 | | | | 0.8 | | | | 0.4 |

CONCLUSIONS

The goal was to study adjuvant activity of three different immune stimulants. This was tested by measuring the serological response after vaccination with oil emulsion vaccines containing a suboptimal concentration of inactivated NDV and different concentrations of one of three different immune stimulants.

The following immune stimulants were investigated:

```
ODN1:
                                    (SEQ ID NO: 1)
[CholTEG]-TGGGGTTTTTTTGCGTTTTTGCGTTTTTGCGTTTT ("GCGT3-TG4T-5Chol")
([CholTEG] = 5'-triethyleneglycol-linked
cholesteryl modification), ODN2:
                                    (SEQ ID NO: 252)
TGGGGTTTTTTTGCGTTTTTGCGTTTTTGCGTTTT ("GCGT3-TG4T"), ODN3:
                                    (SEQ ID NO: 3)
tcgtcgttttgtcgttttgtcgtt("2006-PTO").
```

The backbones of ODN1 and ODN2 immune were phosphodiester-linked, while the backbone of ODN3 was phosphorothioate-linked. The efficacy of each ODN was determined at three different doses; 100 ng, 1000 ng and 5000 ng, supplemented to the suboptimal NDV vaccine.

The serological response was determined at days 0 (prior to vaccination), 7, 14 and 21 after vaccination to investigate whether the addition of these immune stimulants may also lead to an earlier immune response. On days 0 and 7 post vaccination (pv) no antibody levels against NDV were detected, with the exception of one animal (#11618) in the non-diluted NDV vaccine group at day 7.

The serological response expressed as Log 2 HI titres showed significant differences (p<0.0001) between the non-diluted and the suboptimal NDV vaccines at days 14 and 21 pv, indicating that the dilution factor of 50 times was sufficient to create the suboptimal vaccine dose.

The negative control group remained negative during the entire study, indicating that the immune stimulants without NDV vaccine did not result in a non-specific immune response.

The positive control Poly I:C 100 µg dose group showed significantly higher HI titres compared to the naïve NDV vaccine at day 21 (p=0.0053), indicating that this dose group served as a valid positive control group.

The GCGT3-TG4T-5Chol (ODN1) group showed significantly higher HI titres when compared to the diluted NDV vaccine at day 14 pv for all three doses; 100 ng (p=0.0214), 1000 ng (p=0.0003) and 5000 ng (p=0.0243). At day 21 pv, however, no significant differences were observed.

The GCGT3-TG4T (ODN2) group showed significantly higher HI titres when compared to the diluted NDV vaccine at day 14 pv for all three doses; 100 ng (p=0.0003), 1000 ng (p=0.0027) and 5000 ng (p=0.0236). At day 21 significant differences (p=0.0083) were only measured at the 100 ng dose group.

The 2006-PTO (ODN3) group showed significantly higher HI titres compared to the diluted NDV vaccine at day 14 pv for two doses; 1000 ng (p=0.0081) and 5000 ng (p=0.0059). At day 21 pv significant differences (p=0.0296) were only measured at the 5000 ng dose group.

In conclusion, the highest mean HI titres were observed with the 100 ng GCGT3-TG4T (ODN2) dose group, 7.1 Log 2 (14 days pv) and 7.6 Log 2 (21 days pv), indicating an increase in titres when compared to the naïve NDV vaccine of 2.3 Log 2 and 1.4 Log 2 at day 14 and 21 pv, respectively.

The titres of the 1000 ng GCGT3-TG4T-5Chol (ODN1) dose group, 6.9 Log 2 and 7.3 Log 2, at day 14 and 21 pv respectively were almost similar to the ODN2 group. At day 14 pv no significant difference (p=0.7513) between ODN1 and ODN2 groups was observed.

Figure 22:
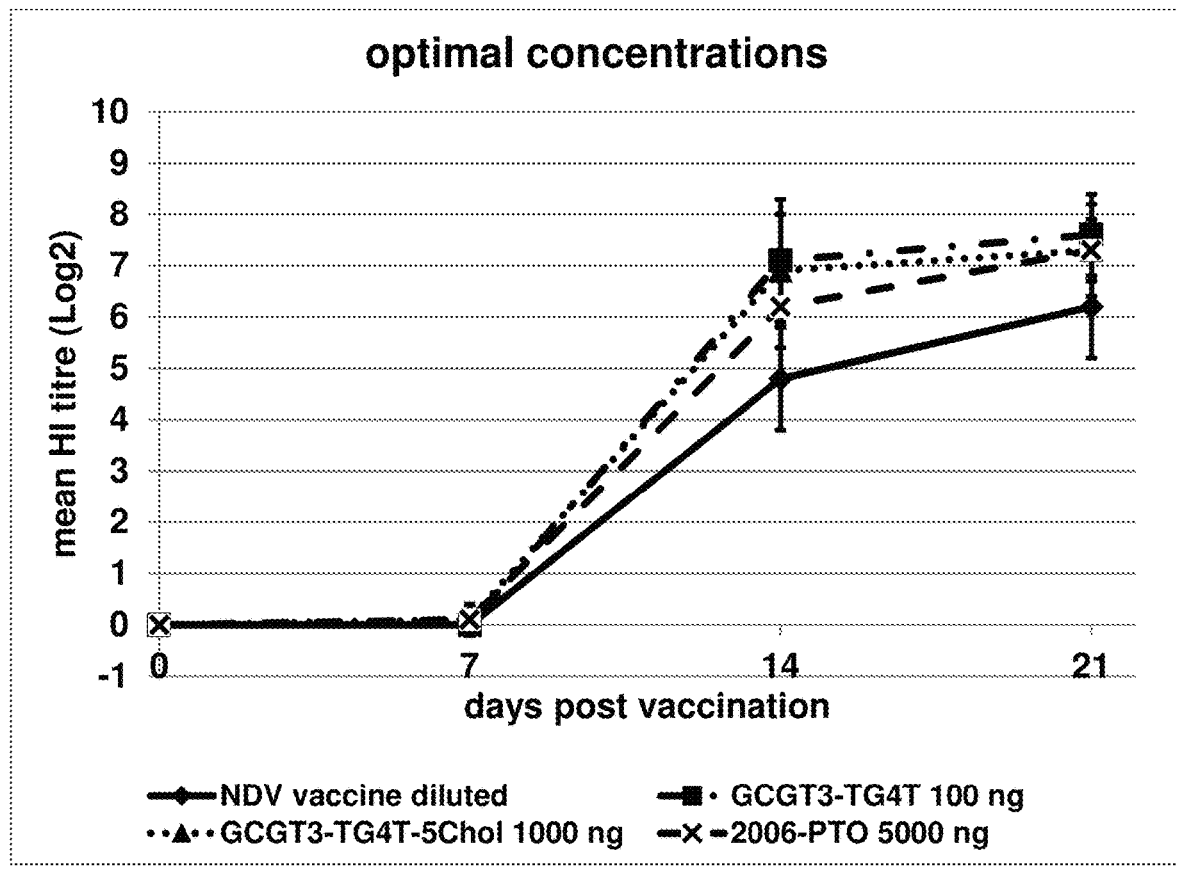
FIG. 22 depicts mean HI titres (Log 2) (with standard deviation) results at the most optimal concentrations of ODNs during the entire study compared to NDV vaccine alone.
Figure 23:
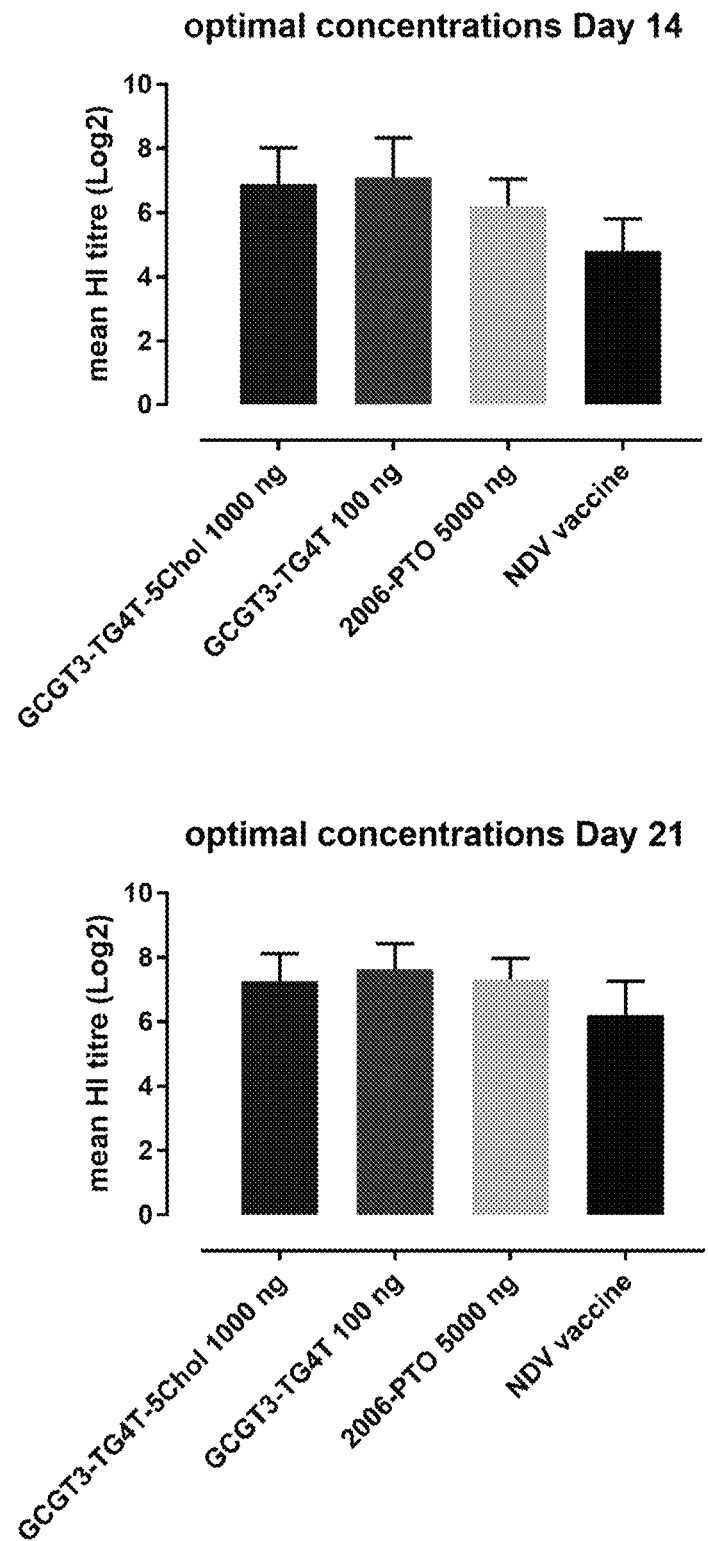
FIG. 23 depicts mean HI titres (Log 2) (with standard deviation) results at the most optimal concentrations of ODNs at day 14 (top panel) and 21 (bottom panel) pv compared to NDV vaccine alone.

The titres of the 5000 ng 2006-PTO (ODN3) dose group were 6.2 Log 2 and 7.3 Log 2 at day 14 and 21 pv, respectively. At day 14 pv, the ODN3 group significantly differed (p=0.0300) from both the ODN1 and ODN2 groups (FIG. 22 and FIG. 23).

At day 21 pv no significant differences between all ODN groups were shown.

These results therefore indicate that all ODNs were capable of significantly increasing the serological response, especially on day 14 after vaccination, also indicating an earlier onset of immunity.

What is claimed:
1. An immunostimulatory composition comprising:
   a) an immunomodulator composition comprising a nucleic acid plasmid and a liposomal delivery vehicle; and
   b) an immunostimulatory oligonucleotide having at least one CpG motif and a guanine nucleotide enriched sequence at or near the 5' terminus of the immunostimulatory oligonucleotide.

2. The immunostimulatory composition of claim 1, wherein the immunomodulator composition and the immunostimulatory oligonucleotide are present in synergistically effective amounts.

3. The immunostimulatory composition of claim 1, wherein the immunostimulatory oligonucleotide comprises a ligand for a cytosolic nucleic acid surveillance molecule.

4. The immunostimulatory composition of claim 3, wherein the immune cytosolic nucleic acid surveillance molecule is a toll-like receptor (TLR).

5. The immunostimulatory composition of claim 3, wherein the cytosolic nucleic acid surveillance molecule is TLR21.

6. The immunostimulatory composition of claim 1, wherein the nucleic acid plasmid concentration of the immunomodulator composition is greater than the concentration of the immunostimulatory oligonucleotide.

7. The immunostimulatory composition of claim 1 further comprising a pharmaceutical carrier.

8. The immunostimulatory composition of claim 1, wherein the liposomal delivery vehicle comprises multilamellar vesicle lipids, extruded lipids, or both.

9. The immunostimulatory composition of claim 1, wherein the liposomal delivery vehicle is cationic.

10. The immunostimulatory composition of claim 8, wherein the cationic liposomal delivery vehicle comprises pairs of lipids selected from the group consisting of N-[1-(2,3-dioleyloxy)propyl]-N,N,N-trimethylammonium chloride (DOTMA) and cholesterol; N-[1-(2,3-dioleoyloxy)propyl]-N,N,N-trimethylammonium chloride (DOTAP) and cholesterol; 1-[2-(oleoyloxy)ethyl]-2-oleyl-3-(2-hydroxyethyl)imidazolinium chloride (DOTIM) and cholesterol; and dimethyldioctadecylammonium bromide (DDAB) and cholesterol.

11. The immunostimulatory composition of claim 1, wherein the nucleic acid plasmid is non-coding.

12. The immunostimulatory composition of claim 1, wherein the nucleic acid plasmid has at least 75% sequence identity with SEQ ID NO. 265.

13. The immunostimulatory composition of claim 1, wherein the nucleic acid plasmid has at least 75% sequence identity with SEQ ID NO.:266.

14. The immunostimulatory composition of claim 1, wherein the nucleic acid plasmid has at least 75% sequence identity with SEQ ID NO:268.

15. The immunostimulatory composition of claim 1, wherein the guanine nucleotide enriched sequence comprises a first plurality of guanine nucleotides.

16. The immunostimulatory composition of claim 15, wherein the first plurality of guanine nucleotides comprises three to eight guanine nucleotides.

17. The immunostimulatory composition of claim 15, wherein the immunostimulatory oligonucleotide comprises SEQ ID NO:16, 17, 18, 19, 20, 21, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 77, 78, 81, 82, 85, 86, 89, 90, 92, 93, 96, 97, 100, 102, 104, 106, 108, 143, or 1.

18. The immunostimulatory composition of claim 15 further comprising a second plurality of guanine nucleotides downstream from the first plurality of guanine nucleotides.

19. The immunostimulatory composition of claim 18, wherein the immunostimulatory oligonucleotide comprises SEQ ID NO:141, 142, 176, 177, 178, 179, 180, 181, 182, 183, 184, 185, 186, 187, 188, 189, 192, 193, 194, 195, 196, 197, 198, 199, 200, 201, 202, 203, or GCGT-Gwire3.

20. The immunostimulatory compositions of claim 18 wherein the first plurality of guanine nucleotides and the second plurality of guanine nucleotides are separated by at least two nucleotides.

21. The immunostimulatory compositions of claim 15, wherein the first plurality of guanine nucleotides and the at least one CpG motif is separated by at least 3 nucleotides.

22. The immunostimulatory compositions of claim 15, wherein the first plurality of guanine nucleotides and the at least one CpG motif is separated by a hexaethyleneglycol, tetraethyleneglycol, propanediol, or derivatives thereof.

23. The immunostimulatory composition of claim 22, wherein the structure of the hexaethyleneglycol is:

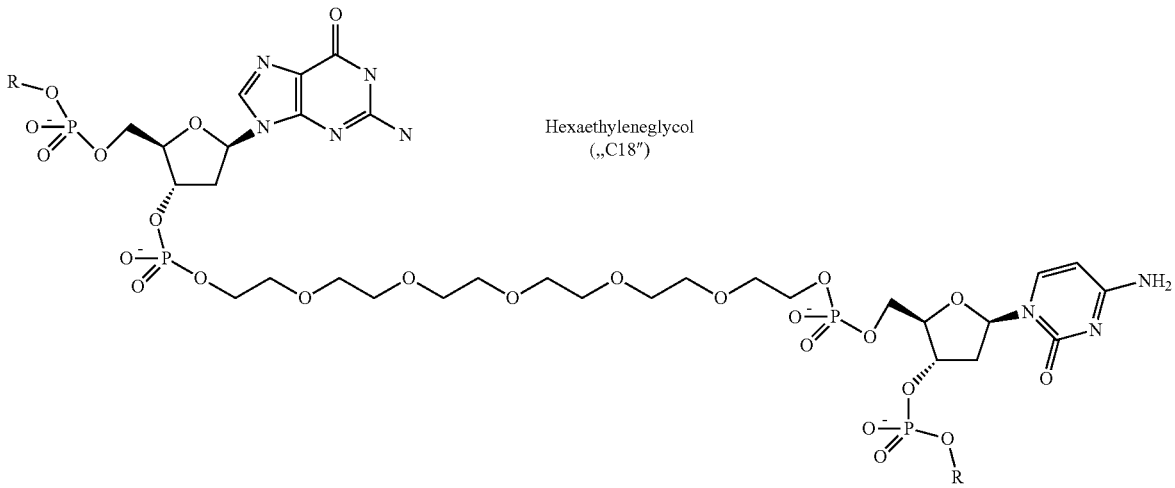

Hexaethyleneglycol („C18")

24. The immunostimulatory composition of claim 1, wherein the immunostimulatory oligonucleotide further comprises a plurality of CpG motifs, each CpG motif of the plurality of CpG motifs being separated from the others of the plurality of CpG motifs by a spacer.

25. The immunostimulatory composition of claim 24, wherein the spacer comprises at least one nucleotide or nucleotide analog.

26. The immunostimulatory composition of claim 25, wherein the spacer comprises a deoxyribosephosphate bridge.

27. The immunostimulatory composition of claim 26, wherein the deoxyribosephosphate bridge is abasic.

28. The immunostimulatory composition of claim 25, wherein the spacer comprises a carbon chain.

29. The immunostimulatory composition of claim 28, wherein the carbon chain is derived from 1,3-propanediol.

30. The immunostimulatory composition of claim 25, wherein the spacer comprises a repeated chemical unit.

31. The immunostimulatory composition of claim 30, wherein the repeated chemical unit is an ethylene glycol.

32. The immunostimulatory composition of claim 1, wherein the immunostimulatory oligonucleotide further comprises a phosphorothioate backbone.

33. The immunostimulatory composition of claim 1, wherein the immunostimulatory oligonucleotide comprises a lipid moiety.

34. The immunostimulatory composition of claim 33, wherein the lipid moiety is cholesteryl.

35. The immunostimulatory composition of claim 33, wherein the lipid moiety is at or near the 5' terminus of the immunostimulatory oligonucleotide.

36. The immunostimulatory composition of claim 1, comprising a CpG sequence element at a 5' terminus, a 3' terminus, or both.

37. The immunostimulatory composition of claim 36 having at least two CpG sequence elements.

38. The immunostimulatory composition of claim 36, wherein the CpG sequence elements are GCGA, GCGG, ACGC, CCGC, GCGT, or TCGC.

39. A method of preparing the immunostimulatory composition of claim 1 comprising:

combining the immunomodulator composition and the immunostimulatory oligonucleotide, to form an immunostimulatory composition;

centrifuging the immunostimulatory composition to generate a supernatant and a pellet; and isolating the pellet.

40. A method for stimulating toll-like receptor 21 (TLR21) comprising:

administering an immunostimulatory oligonucleotide and an immunomodulator composition, wherein the immunostimulatory oligonucleotide has at least one CpG motif and a guanine nucleotide enriched sequence at or near the 5' terminus of the immunostimulatory oligonucleotide, and wherein the immunomodulator composition comprises a noncoding nucleic acid plasmid and a lipid delivery vehicle.

41. The method of claim 40, wherein the immunomodulator composition and the immunostimulatory oligonucleotide are present in synergistically effective amounts.

42. The method of claim 40, wherein the immunostimulatory oligonucleotide comprises a ligand for TLR21.

43. A method of eliciting an immune response in a subject comprising administering to the subject the immunostimulatory composition of claim 1.

44. An immunostimulatory composition comprising:

a. a nucleic acid plasmid and a liposomal delivery vehicle; and b. an immunostimulatory oligonucleotide comprising SEQ ID NO:1.

45. The immunostimulatory composition of claim 44, wherein the nucleic acid plasmid has at least 75% sequence identity with a sequence selected from the group consisting of SEQ ID NO:265, SEQ ID NO:266, SEQ ID NO:268.

46. The immunostimulatory composition of claim 44, wherein the immunostimulatory oligonucleotide further comprises a 5' cholesteryl modification.

47. The immunostimulatory composition of claim 46, wherein the 5' cholesteryl modification comprises a triethyleneglycol linker.

* * * * *